(12) United States Patent
Balazs et al.

(10) Patent No.: US 9,943,611 B2
(45) Date of Patent: Apr. 17, 2018

(54) REVERSIBLE GENE EXPRESSION

(71) Applicant: California Institute of Technology, Pasadena, CA (US)

(72) Inventors: Alejandro Benjamin Balazs, Berkeley, CA (US); David Baltimore, Pasadena, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 335 days.

(21) Appl. No.: 14/067,786

(22) Filed: Oct. 30, 2013

(65) Prior Publication Data

US 2014/0127162 A1  May 8, 2014

Related U.S. Application Data

(60) Provisional application No. 61/721,365, filed on Nov. 1, 2012, provisional application No. 61/779,987, filed on Mar. 13, 2013.

(51) Int. Cl.
*A61K 48/00* (2006.01)
*C12N 15/86* (2006.01)

(52) U.S. Cl.
CPC ......... *A61K 48/0066* (2013.01); *C12N 15/86* (2013.01); *C12N 2750/14143* (2013.01); *C12N 2800/30* (2013.01); *C12N 2800/40* (2013.01); *C12N 2830/001* (2013.01); *C12N 2830/42* (2013.01); *C12N 2840/44* (2013.01)

(58) Field of Classification Search
CPC ............... A61K 48/0066; C12N 15/86; C12N 2800/40; C12N 2830/001; C12N 2830/42; C12N 2840/44; C12N 2750/14143; C12N 2800/30
See application file for complete search history.

(56) References Cited

U.S. PATENT DOCUMENTS

| 5,801,030 | A  | * | 9/1998  | McVey ............... C12N 15/90 435/320.1 |
|-----------|----|---|---------|-----------------------|
| 7,378,273 | B2 |   | 5/2008  | Bleck |
| 7,943,374 | B2 |   | 5/2011  | Hildinger |
| 2002/0022018 | A1 | * | 2/2002 | Curiel ............... A61K 48/0066 424/93.21 |
| 2002/0098572 | A1 |   | 7/2002 | Einerhand et al. |
| 2002/0173477 | A1 |   | 11/2002 | Liou et al. |
| 2007/0116690 | A1 |   | 5/2007  | Yang et al. |
| 2012/0232133 | A1 |   | 9/2012  | Balazs et al. |
| 2012/0315670 | A1 | * | 12/2012 | Jacobson ............... C12N 15/63 435/69.1 |
| 2013/0316366 | A1 |   | 11/2013 | Yu et al. |
| 2017/0000904 | A1 |   | 1/2017  | Wilson et al. |

FOREIGN PATENT DOCUMENTS

| EP | 2 108 706        | 10/2009 |            |
|----|------------------|---------|------------|
| WO | WO 92/15694      | 9/1992  |            |
| WO | WO 2003076561 A2 * | 9/2003 |            |
| WO | WO 2005/007877   | 1/2005  |            |
| WO | WO 2007/126798   | 11/2007 |            |
| WO | WO 2009120978 A2 * | 10/2009 | ........... A61K 48/005 |
| WO | WO 2012/115980   | 8/2012  |            |

OTHER PUBLICATIONS

Furler et al. "Recombinant AAV vectors containing the foot and mouth disease virus 2A sequence confer efficient bicistronic gene expression in cultured cells and rat substantia nigra neurons." Gene Ther. Jun. 2001;8(11):864-73.*
Abremski et al., 1984, "Bacteriophage P1 Site-specific Recombination—Purification and Properties of the Cre Recombinase Protein", J. Biol. Chem., vol. 259, No. 3, pp. 1509-1514, Feb. 10, 1984.
Alam et al., "Lung surfactant protein B promoter function is dependent on the helical phasing, orientation and combinatorial actions of cis-DNA elements", Gene, vol. 282, pp. 103-111, 2002.
Alexopoulou et al., "The CMV early enhancer/chicken β actin (CAG) promoter can be used to drive transgene expression during the differentiation of murine embryonic stem cells into vascular progenitors", BMC Cell Biology, 2008, vol. 9, No. 2, 11 pages.
Brisson et al., "Expression of a bacterial gene in plants by using a viral vector", Nature, Aug. 9, 1984, vol. 310, pp. 511-514.
De Felipe, "Skipping the co-expression problem: the new 2A "CHYSEL" technology", Genetic Vaccines and Therapy, 2004, vol. 2, No. 13, 6 pages.
De Felipe et al., "Targeting of Proteins Derived from Self-Processing Polyproteins Containing Multiple Signal Sequences", Traffic, 2004, vol. 5, pp. 616-626.
File History of U.S. Appl. No. 13/400,945, filed Feb. 21, 2012.
Final Office Action dated Mar. 10, 2014 in U.S. Appl. No. 13/400,945.
Goverdhana et al., "Regulatable gene expression systems for gene therapy applications: progress and future challenges", Molecular Therapy, Aug. 2005, vol. 12, No. 2, pp. 189-211.
Gurley et al., "Upstream Sequences Required for Efficient Expression of a Soybean Heat Shock Gene", Mol. Cell. Biol., Feb. 1986, vol. 6, No. 2, pp. 559-565.
Haberman et al., "Regulation of gene expression in adeno-associated virus vectors in the brain", Methods, 2002, vol. 28, No. 2, pp. 219-226.
International Search Report and Written Opinion dated Jan. 28, 2014 in Application No. PCT/US2013/067608.
Lakso et al., "Targeted oncogene activation by site-specific recombination in transgenic mice", Proc. Natl. Acad. Sci. USA, Jul. 1992, vol. 89, pp. 6232-6236.

(Continued)

*Primary Examiner* — Titilayo Moloye
(74) *Attorney, Agent, or Firm* — Knobbe, Martens, Olson & Bear, LLP

(57) ABSTRACT

According to some embodiments herein, expression systems and methods for reversible gene expression are provided. In some embodiments, adeno-associated viral vectors encoding a gene product of interest and comprising a plurality of recombinase target sites are provided. In some embodiments, a source of recombinase is provided. In some embodiments, the gene product of interest is expressed, and the recombinase then induces recombination events between the recombinase target sites, thus reducing or eliminating expression of the gene product of interest.

25 Claims, 34 Drawing Sheets

(56) References Cited

OTHER PUBLICATIONS

Livet et al., "Transgenic strategies for combinatorial expression of fluorescent proteins in the nervous system", Nature, Nov. 1, 2007, vol. 450, pp. 56-63.
Lundberg et al., "A brief introduction to cell-penetrating peptides", J. Mol. Recognit., 2003, vol. 16, pp. 227-233.
Muller et al., "Repression of lac Promoter as a Function of Distance, Phase and Quality of an Auxiliary lac Operator", J. Mol. Biol., vol. 257, pp. 21-29, 1996.
O'Gorman et al., "Recombinase-Mediated Gene Activation and Site Specific Integration in Mammalian Cells", Science, Mar. 15, 1991, vol. 251, pp. 1351-1355.
Office Action dated Jul. 3, 2013 in U.S. Appl. No. 13/400,945.
Orban et al., "Tissue- and site-specific DNA recombination in transgenic mice", Proc. Natl. Acad. Sci. USA, Aug. 1992, vol. 89, pp. 6861-6865.
Xie et al., "Domains of the Rat rDNA Promoter Must Be Aligned Stereospecifically", Molecular and Cellular Biology, vol. 12, No. 3, pp. 1266-1275, Mar. 1992.
Xu et al., "CMV-β-Actin Promoter Directs Higher Expression from an Adeno-Associated Viral Vector in the Liver than the Cytomegalovirus or Elongation Factor 1a Promoter and Results in Therapeutic Levels of Human Factor X in Mice", Human Gene Therapy, vol. 12, pp. 563-573, Mar. 20, 2001.
Extended European Search Report dated Jun. 9, 2016 in Application No. 13851143.1.

* cited by examiner

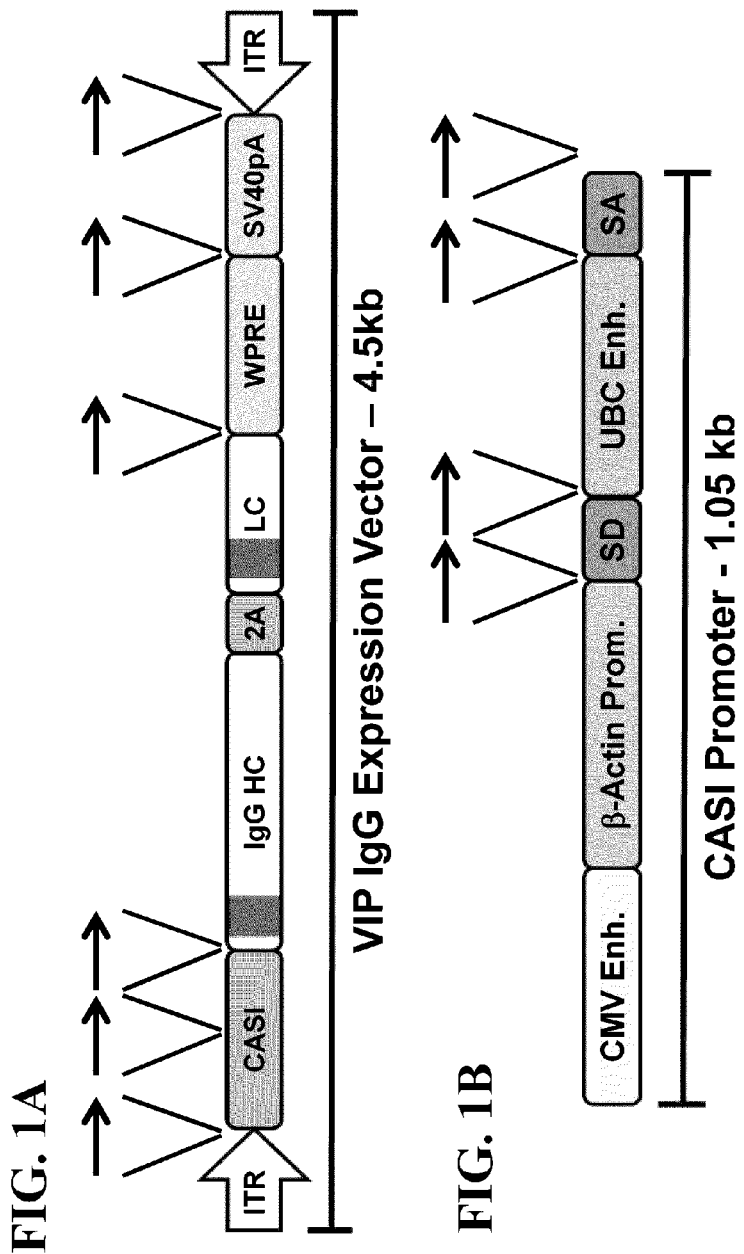

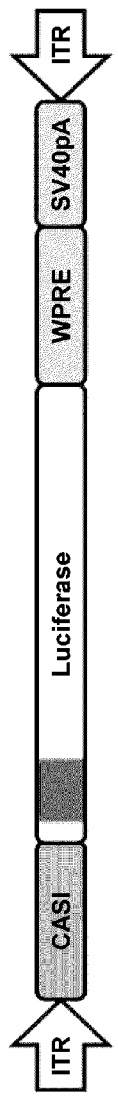
FIG. 2A
FIG. 2B
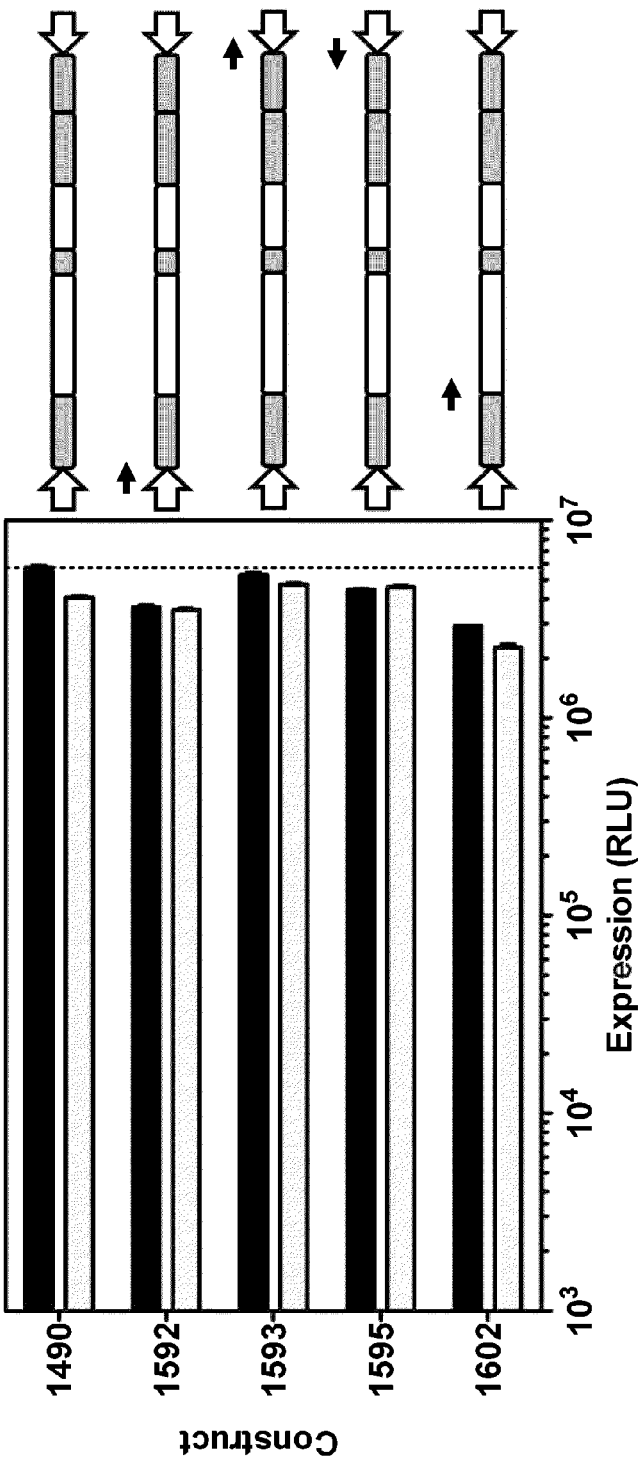
FIG. 2C

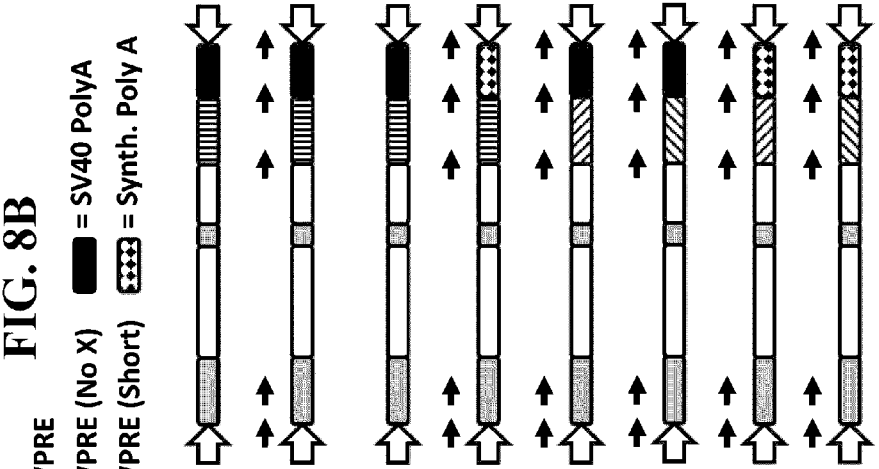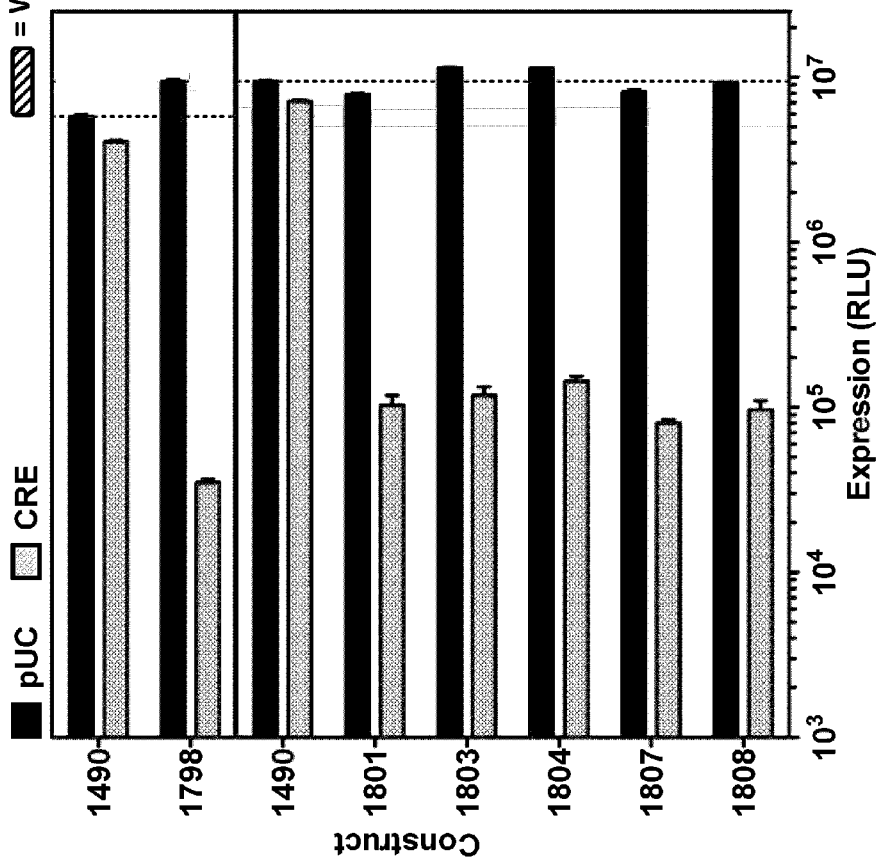

1 Week Post AAV Administration
Mouse #1-2:ZsGreen
Mouse #3-4:Cre

4 Weeks Post AAV Administration
Mouse #1-2:ZsGreen
Mouse #3-4:Cre

20 Weeks Post 1st Transduction

21 Days After 2nd Vector Administration

28 Days After 2nd Vector Administration

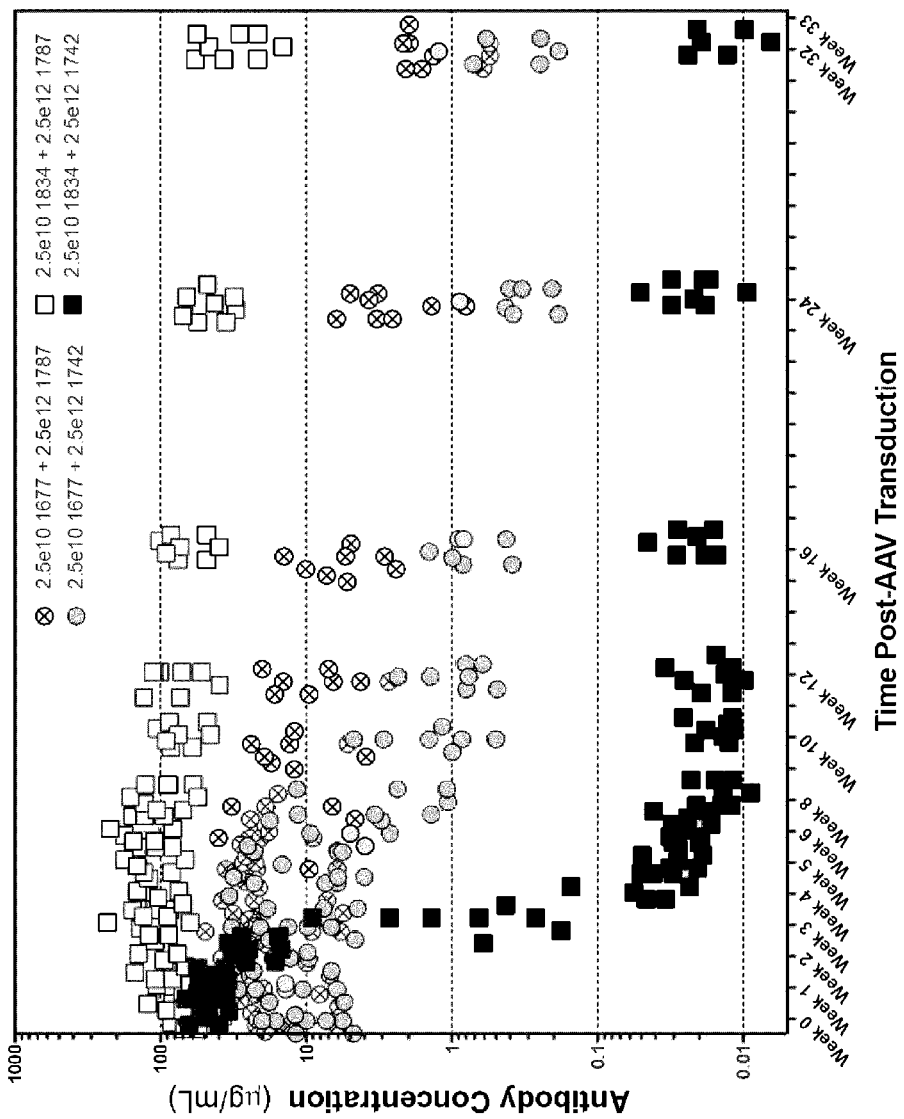

```
                              SEQUENCE LISTING

<160> NUMBER OF SEQ ID NOS: 43

<210> SEQ ID NO 1
<211> LENGTH: 5874
<212> TYPE: DNA
<213> ORGANISM: Artificial Sequence
<220> FEATURE:
<223> OTHER INFORMATION: Vector 1806

<400> SEQUENCE: 1
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctactag ataacttcgt atagcataca ttatacgaag     180
ttatactagt ggagttccgc gttacataac ttacggtaaa tggcccgcct ggctgaccgc     240
ccaacgaccc ccgcccattg acgtcaataa tgacgtatgt tcccatagta acgccaatag     300
ggactttcca ttgacgtcaa tgggtggagt atttacggta aactgcccac ttggcagtac     360
atcaagtgta tcatatgcca agtacgcccc ctattgacgt caatgacggt aaatggcccg     420
cctggcatta tgcccagtac atgaccttat gggactttcc tacttggcag tacatctacg     480
tattagtcat cgctattacc atggtcgagg tgagccccac gttctgcttc actctcccca     540
tctccccccc ctccccaccc ccaatttgt atttatttat tttttaatta ttttgtgcag     600 cgatggggggc gggggggggg ggggggcgcg cgccaggcgg ggcggggcgg ggcgagggggc    660 ggggcggggc gaggcggaga ggtgcggcgg cagccaatca gagcggcgcg ctccgaaagt     720 ttcctttat ggcgaggcgg cggcggcggc ggccctataa aaagcgaagc gcgcggcggg     780
cgggagtcgc tgcgcgctgc cttcgccccg tgccccgctc cgccgccgcc tcgcgccgcc     840
cgccccggct ctgactgacc gcgttactaa acaggtaag tccataactt cgtatagcat      900
acattatacg aagttatggc ctccgcgccg ggttttggcg cctcccgcgg gcgcccccct     960
cctcacggcg agcgctgcca cgtcagacga agggcgcagc gagcgtcctg atccttccgc    1020
ccggacgctc aggacagcgg cccgctgctc ataagactcg gccttagaac cccagtatca    1080
gcagaaggac attttaggac gggacttggg tgactctagg gcactggttt tctttccaga    1140
gagcggaaca ggcgaggaaa agtagtccct tctcggcgat tctgcggagg gatctccgtg    1200
gggcggtgaa cgccgatgat ataacttcgt atagcataca ttatacgaag ttatgcctct    1260
actaaccatg ttcatgtttt ctttttttt ctacaggtcc tgggtgacga acaggcggcc    1320
gccatggaag atgccaaaaa cattaagaag ggcccagcgc cattctaccc actcgaagac    1380
gggaccgccg gcgagcagct gcacaaagcc atgaagcgct acgccctggt gcccggcacc    1440
atcgccttta ccgacgcaca tatcgaggtg gacattacct acgccgagta cttcgagatg    1500
agcgttcggc tggcagaagc tatgaagcgc tatgggctga atacaaacca tcggatcgtg    1560
gtgtgcagcg agaatagctt gcagttcttc atgcccgtgt tgggtgccct gttcatcggt    1620
gtggctgtgg ccccagctaa cgacatctac aacgagcgcg agctgctgaa cagcatgggc    1680
atcagccagc ccaccgtcgt attcgtgagc aagaaagggc tgcaaaagat cctcaacgtg    1740
caaaagaagc taccgatcat acaaaagatc atcatcatg atagcaagac cgactaccag    1800
ggcttccaaa gcatgtacac cttcgtgact tcccatttgc cacccggctt caacgagtac    1860
```

```
gacttcgtgc ccgagagctt cgaccgggac aaaaccatcg ccctgatcat gaacagtagt    1920
ggcagtaccg gattgcccaa gggcgtagcc ctaccgcacc gcaccgcttg tgtccgattc    1980
agtcatgccc gcgaccccat cttcggcaac cagatcatcc ccgacaccgc tatcctcagc    2040
gtggtgccat ttcaccacgg cttcggcatg ttcaccacgc tgggctactt gatctgcggc    2100
tttcgggtcg tgctcatgta ccgcttcgag gaggagctat tcttgcgcag cttgcaagac    2160
tataagattc aatctgccct gctggtgccc acactattta gcttcttcgc taagagcact    2220
ctcatcgaca agtacgacct aagcaacttg cacgagatcg ccagcggcgg ggcgccgctc    2280
agcaaggagg taggtgaggc cgtggccaaa cgcttccacc taccaggcat ccgccagggc    2340
tacggcctga cagaaacaac cagcgccatt ctgatcaccc ccgaagggga cgacaagcct    2400
ggcgcagtag gcaaggtggt gcccttcttc gaggctaagg tggtggactt ggacaccggt    2460
aagacactgg gtgtgaacca gcgcggcgag ctgtgcgtcc gtggcccat gatcatgagc    2520 ggctacgtta acaaccccga ggctacaaac gctctcatcg acaaggacgg ctggctgcac    2580
agcggcgaca tcgcctactg ggacgaggac gagcacttct tcatcgtgga ccggctgaag    2640
agcctgatca atacaaggg ctaccaggta gccccagccg aactggagag catcctgctg    2700
caacacccca acatcttcga cgccggggtc gccggcctgc ccgacgacga tgccggcgag    2760
ctgcccgccg cagtcgtcgt gctggaacac ggtaaaacca tgaccgagaa ggagatcgtg    2820
gactatgtgg ccagccaggt tacaaccgcc aagaagctgc gcgtggtgt tgtgttcgtg    2880 gacgaggtgc ctaaaggact gaccggcaag ttggacgccc gcaagatccg cgagattctc    2940
attaaggcca gaagggcgg caagatcgcc gtgtaaagga tccataactt cgtatagcat    3000
acattatacg aagttatgat cctaatcaac ctctggatta caaaatttgt gaaagattga    3060
ctggtattct taactatgtt gctccttta cgctatgtgg atacgctgct ttaatgcctt    3120
tgtatcatgc tattgcttcc cgtatggctt tcattttctc ctccttgtat aaatcctggt    3180
tgctgtctct ttatgaggag ttgtggcccg ttgtcaggca acgtggcgtg gtgtgcactg    3240
tgtttgctga cgcaacccc actggttggg gcattgccac cacctgtcag ctccttttccg    3300 ggactttcgc tttcccccctc cctattgcca cggcggaact catcgccgcc tgccttgccc    3360
gctgctggac aggggctcgg ctgttgggca ctgacaattc cgtggtgttg tcggggaaat    3420
catcgtcctt tccggtacca taacttcgta tagcatacat tatacgaagt tatttcgagc    3480
agacatgata agatacattg atgagtttgg acaaaccaca actagaatgc agtgaaaaaa    3540
atgctttatt tgtgaaattt gtgatgctat tgctttattt gtaaccatta taagctgcaa    3600
taaacaagtt aacaacaaca attgcattca ttttatgttt caggttcagg gggagatgtg    3660
ggaggttttt taaagcaagt aaaacctcta caaatgtggt aaaatcaagc ttataacttc    3720
gtatagcata cattatacga agttatagct taggaacccc tagtgatgga gttggccact    3780
ccctctctgc gcgctcgctc gctcactgag gccgggcgac caaggtcgc ccgacgcccg    3840 ggcttttgccc gggcggcctc agtgagcgag cgagcgcgca gagagggagt ggccaagcta    3900
gcgggcgatt aaggaaaggg ctagatcatt cttgaagacg aaagggcctc gtgatacgcc    3960
tatttttata ggttaatgtc atgataataa tggtttctta cgtcaggt ggcactttc    4020 ggggaaatgt gcgcggaacc cctatttgtt tatttttcta aatacattca aatatgtatc    4080
cgctcatgag acaataaccc tgataaatgc ttcaataata ttgaaaaagg aagagtatga    4140
gtattcaaca tttccgtgtc gcccttattc cctttttttgc ggcattttgc cttcctgttt    4200
ttgctcaccc agaaacgctg gtgaaagtaa aagatgctga agatcagttg ggtgcacgag    4260
```

-continued

```
tgggttacat cgaactggat ctcaacagcg gtaagatcct tgagagtttt cgccccgaag    4320
aacgttttcc aatgatgagc acttttaaag ttctgctatg tggcgcggta ttatcccgtg    4380
ttgacgccgg gcaagagcaa ctcggtcgcc gcatacacta ttctcagaat gacttggttg    4440
agtactcacc agtcacagaa aagcatctta cggatggcat gacagtaaga gaattatgca    4500
gtgctgccat aaccatgagt gataacactg cggccaactt acttctgaca acgatcggag    4560
gaccgaagga gctaaccgct tttttgcaca acatggggga tcatgtaact cgccttgatc    4620
gttgggaacc ggagctgaat gaagccatac caaacgacga gcgtgacacc acgatgcctg    4680
tagcaatggc aacaacgttg cgcaaactat taactggcga actacttact ctagcttccc    4740
ggcaacaatt aatagactgg atggaggcgg ataaagttgc aggaccactt ctgcgctcgg    4800
cccttccggc tggctggttt attgctgata aatctggagc cggtgagcgt gggtctcgcg    4860
gtatcattgc agcactgggg ccagatggta agccctcccg tatcgtagtt atctacacga    4920
cggggagtca ggcaactatg gatgaacgaa atagacagat cgctgagata ggtgcctcac    4980
tgattaagca ttggtaactg tcagaccaag tttactcata tatactttag attgatttaa    5040
aacttcattt ttaatttaaa aggatctagg tgaagatcct tttgataat ctcatgacca    5100 aaatccctta acgtgagttt tcgttccact gagcgtcaga ccccgtagaa aagatcaaag    5160
gatcttcttg agatcctttt tttctgcgcg taatctgctg cttgcaaaca aaaaaaccac    5220
cgctaccagc ggtggtttgt ttgccggatc aagagctacc aactcttttt ccgaaggtaa    5280
ctggcttcag cagagcgcag ataccaaata ctgttcttct agtgtagccg tagttaggcc    5340
accacttcaa gaactctgta gcaccgccta catacctcgc tctgctaatc ctgttaccag    5400
tggctgctgc cagtggcgat aagtcgtgtc ttaccgggtt ggactcaaga cgatagttac    5460
cggataaggc gcagcggtcg ggctgaacgg ggggttcgtg cacacagccc agcttggagc    5520
gaacgaccta caccgaactg agatacctac agcgtgagct atgagaaagc gccacgcttc    5580
ccgaagggag aaaggcggac aggtatccgg taagcggcag gtcggaaca ggagagcgca    5640 cgagggagct ccaggggga aacgcctggt atctttatag tcctgtcggg tttcgccacc    5700
tctgacttga gcgtcgattt ttgtgatgct cgtcaggggg gcggagccta tggaaaaacg    5760
ccagcaacgc ggcctttta cggttcctgg ccttttgctg ccttttgct cacatgtaat    5820 aaacacacac acaccaacaa ccgtggttgg ttgttgtgtt ggtttattct cgag          5874
```

<210> SEQ ID NO 2
<211> LENGTH: 6489
<212> TYPE: DNA
<213> ORGANISM: Artificial Sequence
<220> FEATURE:
<223> OTHER INFORMATION: Vector 1833

<400> SEQUENCE: 2

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctactag ataacttcgt atagcataca ttatacgaag    180
ttatactagt ggagttccgc gttacataac ttacggtaaa tggcccgcct ggctgaccgc    240
ccaacgaccc ccgcccattg acgtcaataa tgacgtatgt tcccatagta acgccaatag    300
ggactttcca ttgacgtcaa tgggtggagt atttacggta aactgcccac ttggcagtac    360
atcaagtgta tcatatgcca agtacgcccc ctattgacgt caatgacggt aaatggcccg    420
```

```
cctggcatta tgcccagtac atgaccttat gggactttcc tacttggcag tacatctacg    480
tattagtcat cgctattacc atggtcgagg tgagccccac gttctgcttc actctcccca    540
tctccccccc ctccccaccc ccaatttgt atttatttat tttttaatta ttttgtgcag    600 cgatggggc ggggggggg ggggggcgcg cgccaggcgg ggcggggcgg ggcgaggggc    660 ggggcgggc gaggcggaga ggtgcggcgg cagccaatca gagcggcgcg ctccgaaagt    720 ttcctttat ggcgaggcgg cggcggcggc ggccctataa aaagcgaagc gcgcggcggg    780
cgggagtcgc tgcgcgctgc cttcgccccg tgccccgctc cgccgccgcc tcgcgccgcc    840
cgccccggct ctgactgacc gcgttactaa aacaggtaag tccataactt cgtatagcat    900
acattatacg aagttatggc ctccgcgccg ggttttggcg cctcccgcgg gcgccccct    960 cctcacggcg agcgctgcca cgtcagacga agggcgcagc gagcgtcctg atccttccgc    1020
ccggacgctc aggacagcgg cccgctgctc ataagactcg gccttagaac cccagtatca    1080
gcagaaggac attttaggac gggacttggg tgactctagg gcactggttt tctttccaga    1140
gagcggaaca ggcgaggaaa agtagtccct tctcggcgat tctgcggagg gatctccgtg    1200
gggcggtgaa cgccgatgat ataacttcgt atagcataca ttatacgaag ttatgcctct    1260
actaaccatg ttcatgtttt cttttttttt ctacaggtcc tgggtgacga acaggcggcc    1320
gccatggcga cgggttcaag aacttcccta cttcttgcat ttggcctgct ttgtttgccg    1380
tggttacagg agggctcggc acaggttcag ctggttcagt ccggggctga ggtgaagaag    1440
cctggggcct cagtgaaggt ttcttgtcag gcttctggat acagattcag taactttgtt    1500
attcattggg tgcgccaggc ccccggacag aggtttgagt ggatgggatg gatcaatcct    1560
tacaacggaa acaaagaatt ttcagcgaag ttccaggaca gagtcacctt taccgcggac    1620
acatccgcga acacagccta catggagttg aggagcctca ggtctgcaga cacggctgtt    1680
tattattgtg cgagagtggg gccatatagt tgggatgatt ctccccagga caattattat    1740
atggacgtct ggggcaaagg gaccacggtc atcgtgagct cagccagcac caagggccca    1800
tcggtcttcc ccctggcacc ctcctccaag agcacctctg ggggcacagc ggccctgggc    1860
tgcctggtca aggactactt ccccgaaccg gtgacggtgt cgtggaactc aggcgccctg    1920
accagcggcg tgcacacctt cccggctgtc ctacagtcct caggactcta ctccctcagc    1980
agcgtggtga ccgtgccctc cagcagcttg ggcacccaga cctacatctg caacgtgaat    2040
cacaagccca gcaacaccaa ggtggacaag aaagttgagc ccaaatcttg tgacaaaact    2100
cacacatgcc caccgtgccc agcacctgaa ctcctggggg gaccgtcagt cttcctcttc    2160
cccccaaaac ccaaggacac cctcatgatc tcccggaccc ctgaggtcac atgcgtggtg    2220
gtggacgtga gccacgaaga ccctgaggtc aagttcaact ggtatgttga cggcgtggag    2280
gtgcataatg ccaagacaaa gccgcgggag gagcagtaca acagcacgta ccgtgtggtc    2340
agcgtcctca ccgtcctgca ccaggactgg ctgaatggca aggagtacaa gtgcaaggtc    2400
tccaacaaag ccctcccagc ccccatcgag aaaaccatct ccaaagccaa agggcagccc    2460
cgagaaccac aggtgtacac cctgccccca tcccgggatg agctgaccaa gaatcaagtc    2520
agcctgacct gcctggtcaa aggcttctat cccagcgaca tcgccgtgga gtgggagagc    2580
aatgggcagc cggagaacaa ctacaagacc acgcctcccg tgctggactc cgacggctcc    2640
ttcttcctct actcaaaact caccgtggac aagagcaggt ggcagcaggg gaacgtcttc    2700
tcatgctccg tgatgcatga ggctctgcac aaccactaca cgcagaagag cctctccctg    2760 tctccggggtc gaaaaagaag atcaggttcg ggtgcgccag taaagcagac attaaacttt    2820
```

```
gatttgctga aacttgcagg tgatgtagag tcaaatccag gtccaatggc aacagggagc    2880
cgaacctctc tgctccttgc tttcgggctc ctttgcctac cgtggctcca agagggctcg    2940
gcagagatcg ttctcacgca gtctccaggc accctgtctc tgtctccagg ggaaagagcc    3000
accttctcct gtaggtccag tcacagcatt cgcagccgcc gcgtagcctg gtaccagcac    3060
aaacctggcc aggctccaag gctggtcata catggtgttt ccaatagggc ctctggcatc    3120
tcagacaggt tcagcggcag tgggtctggg acagacttca ctctcaccat caccagagtg    3180
gagcctgaag actttgcact gtactactgt caggtctatg gtgcctcctc gtacactttt    3240
ggccagggga ccaaactgga gaggaaacgt acggtggccg ctcccagcgt gttcatcttc    3300
cctccctctg atgaacagct gaaaagcgga acagccagcg tggtgtgtct gctgaacaac    3360
ttctacccca gagaagccaa agtgcagtgg aaggtggaca cgccctgcca gagcggaaac    3420
agccaggaaa gcgtgacaga gcaggattcc aaggattcca catacagcct gagcagcaca    3480
ctgacactgt ccaaggccga ctacgagaag cacaaggtgt acgcctgcga agtgacacac    3540
cagggactgt cctcccctgt gacaaagagc ttcaacagag agaatgctaa aaggatccat    3600
aacttcgtat agcatacatt atacgaagtt atgatcctaa tcaacctctg gattacaaaa    3660
tttgtgaaag attgactggt attcttaact atgttgctcc ttttacgcta tgtggatacg    3720
ctgctttaat gcctttgtat catgctattg cttcccgtat ggctttcatt ttctcctcct    3780
tgtataaatc ctggttgctg tctctttatg aggagttgtg gcccgttgtc aggcaacgtg    3840
gcgtggtgtg cactgtgttt gctgacgcaa ccccactgg ttgggcatt gccaccacct    3900 gtcagctcct ttccgggact ttcgctttcc ccctccctat tgccacggcg gaactcatcg    3960
ccgcctgcct tgcccgctgc tggacagggg ctcggctgtt gggcactgac aattccgtgg    4020
tgttgtcggg gaaatcatcg tccttccgg taccataact tcgtatagca tacattatac    4080
gaagttattt cgagcagaca tgataagata cattgatgag tttggacaaa ccacaactag    4140
aatgcagtga aaaaaatgct ttatttgtga atttgtgat gctattgctt tatttgtaac    4200
cattataagc tgcaataaac aagttaacaa caacaattgc attcatttta tgtttcaggt    4260 tcaggggag atgtgggagg ttttttaaag caagtaaaac ctctacaaat gtggtaaaat    4320
caagcttata acttcgtata gcatacatta tacgaagtta tagcttagga acccctagtg    4380
atggagttgg ccactccctc tctgcgcgct cgctcgctca ctgaggccgg gcgaccaaag    4440
gtcgcccgac gcccgggctt tgcccgggcg gcctcagtga gcgagcgagc gcgcagagag    4500
ggagtggcca agctagcggg cgattaagga aagggctaga tcattcttga agacgaaagg    4560
gcctcgtgat acgcctattt ttataggtta atgtcatgat aataatggtt tcttagacgt    4620
caggtggcac ttttcgggga atgtgcgcg gaacccctat ttgtttattt ttctaaatac    4680
attcaaatat gtatccgctc atgagacaat aaccctgata aatgcttcaa taatattgaa    4740
aaaggaagag tatgagtatt caacatttcc gtgtcgccct tattccctt tttgcggcat    4800 tttgccttcc tgtttttgct cacccagaaa cgctggtgaa agtaaaagat gctgaagatc    4860
agttgggtgc acgagtgggt tacatcgaac tggatctcaa cagcggtaag atccttgaga    4920
gttttcgccc cgaagaacgt tttccaatga tgagcacttt taaagttctg ctatgtggcg    4980
cggtattatc ccgtgttgac gccgggcaag agcaactcgg tcgccgcata cactattctc    5040
agaatgactt ggttgagtac tcaccagtca cagaaaagca tcttacggat ggcatgacag    5100
taagagaatt atgcagtgct gccataacca tgagtgataa cactgcggcc aacttacttc    5160
```

| | |
|---|---|
| tgacaacgat cggaggaccg aaggagctaa ccgcttttt gcacaacatg ggggatcatg | 5220 |
| taactcgcct tgatcgttgg gaaccggagc tgaatgaagc cataccaaac gacgagcgtg | 5280 |
| acaccacgat gcctgtagca atggcaacaa cgttgcgcaa actattaact ggcgaactac | 5340 |
| ttactctagc ttcccggcaa caattaatag actggatgga ggcggataaa gttgcaggac | 5400 |
| cacttctgcg ctcggccctt ccggctggct ggtttattgc tgataaatct ggagccggtg | 5460 |
| agcgtgggtc tcgcggtatc attgcagcac tggggccaga tggtaagccc tcccgtatcg | 5520 |
| tagttatcta cacgacgggg agtcaggcaa ctatggatga acgaaataga cagatcgctg | 5580 |
| agataggtgc ctcactgatt aagcattggt aactgtcaga ccaagtttac tcatatatac | 5640 |
| tttagattga tttaaaactt catttttaat ttaaaaggat ctaggtgaag atccttttg | 5700 |
| ataatctcat gaccaaaatc ccttaacgtg agttttcgtt ccactgagcg tcagaccccg | 5760 |
| tagaaaagat caaaggatct tcttgagatc cttttttct gcgcgtaatc tgctgcttgc | 5820 |
| aaacaaaaaa accaccgcta ccagcggtgg tttgtttgcc ggatcaagag ctaccaactc | 5880 |
| tttttccgaa ggtaactggc ttcagcagag cgcagatacc aaatactgtt cttctagtgt | 5940 |
| agccgtagtt aggccaccac ttcaagaact ctgtagcacc gcctacatac ctcgctctgc | 6000 |
| taatcctgtt accagtggct gctgccagtg gcgataagtc gtgtcttacc gggttggact | 6060 |
| caagacgata gttaccggat aaggcgcagc ggtcgggctg aacggggggt tcgtgcacac | 6120 |
| agcccagctt ggagcgaacg acctacaccg aactgagata cctacagcgt gagctatgag | 6180 |
| aaagcgccac gcttcccgaa gggagaaagg cggacaggta tccggtaagc ggcagggtcg | 6240 |
| gaacaggaga gcgcacgagg gagcttccag ggggaaacgc ctggtatctt tatagtcctg | 6300 |
| tcgggtttcg ccacctctga cttgagcgtc gatttttgtg atgctcgtca gggggggcgga | 6360 |
| gcctatggaa aaacgccagc aacgcggcct ttttacggtt cctggccttt tgctggcctt | 6420 |
| ttgctcacat gtaataaaca cacacacc aacaaccgtg gttggttgtt gtgttggttt | 6480 |
| attctcgag | 6489 |

<210> SEQ ID NO 3
<211> LENGTH: 6456
<212> TYPE: DNA
<213> ORGANISM: Artificial Sequence
<220> FEATURE:
<223> OTHER INFORMATION: Vector 1834

<400> SEQUENCE: 3

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctactag ataacttcgt atagcataca ttatacgaag | 180 |
| ttatactagt ggagttccgc gttacataac ttacggtaaa tggcccgcct ggctgaccgc | 240 |
| ccaacgaccc ccgcccattg acgtcaataa tgacgtatgt tcccatagta acgccaatag | 300 |
| ggactttcca ttgacgtcaa tgggtggagt atttacggta aactgcccac ttggcagtac | 360 |
| atcaagtgta tcatatgcca agtacgcccc ctattgacgt caatgacggt aaatggcccg | 420 |
| cctggcatta tgcccagtac atgaccttat gggactttcc tacttggcag tacatctacg | 480 |
| tattagtcat cgctattacc atggtcgagg tgagccccac gttctgcttc actctcccca | 540 |
| tctcccccc ctccccaccc ccaattttgt atttatttat ttttaatta ttttgtgcag | 600 |
| cgatggggc gggggggggg ggggggcgcg cgccaggcgg ggcggggcgg ggcgagggc | 660 |
| ggggcgggc gaggcggaga ggtgcggcgg cagccaatca gagcggcgcg ctccgaaagt | 720 |

```
ttccttttat ggcgaggcgg cggcggcggc ggccctataa aaagcgaagc gcgcggcggg    780
cgggagtcgc tgcgcgctgc cttcgccccg tgccccgctc cgccgccgcc tcgcgccgcc    840
cgccccggct ctgactgacc gcgttactaa acaggtaagt ccataactt cgtatagcat     900 acattatacg aagttatggc ctccgcgccg ggttttggcg cctcccgcgg gcgcccccct    960
cctcacggcg agcgctgcca cgtcagacga agggcgcagc gagcgtcctg atccttccgc   1020
ccggacgctc aggacagcgg cccgctgctc ataagactcg gccttagaac cccagtatca   1080
gcagaaggac attttaggac gggacttggg tgactctagg cactggtttt ctttccaga   1140 gagcggaaca ggcgaggaaa agtagtccct tctcggcgat tctgcggagg gatctccgtg   1200
gggcggtgaa cgccgatgat ataacttcgt atagcataca ttatacgaag ttatgcctct   1260
actaaccatg ttcatgtttt cttttttttt ctacaggtcc tgggtgacga acaggcggcc   1320
gccatggcga cgggttcaag aacttcccta cttcttgcat ttggcctgct ttgtttgccg   1380
tggttacagg agggctcggc acaggtgcag ctggtgcagt ctggaggtca gatgaagaag   1440
cctggcgagt cgatgagaat tcttgtcgg gcttctggat atgaatttat tgattgtacg    1500
ctaaattgga ttcgtctggc ccccggaaaa aggcctgagt ggatgggatg ctgaagcct   1560 cgggggggg ccgtcaacta cgcacgtcca cttcagggca gagtgaccat gactcgagac   1620
gtttattccg acacagcctt tttggagctg cgctcgttga cagtagacga cacggccgtc   1680
tacttttgta ctaggggaaa aaactgtgat tacaattggg acttcgaaca ctggggccgg   1740
ggcaccccgg tcatcgtctc atcaccgagc accaagggcc catcggtctt cccctggca   1800 ccctcctcca agagcacctc tgggggcaca gcggccctgg gctgcctggt caaggactac   1860
ttccccgaac cggtgacggt gtcgtggaac tcaggcgccc tgaccagcgg cgtgcacacc   1920
ttcccggctg tcctacagtc ctcaggactc tactccctca gcagcgtggt gaccgtgccc   1980
tccagcagct gggcaccca gacctacatc tgcaacgtga atcacaagcc cagcaacacc   2040
aaggtggaca agaaagttga gcccaaatct tgtgacaaaa ctcacacatg cccaccgtgc   2100
ccagcacctg aactcctggg gggaccgtca gtcttcctct tccccccaaa acccaaggac   2160
accctcatga tctcccggac ccctgaggtc acatgcgtgg tggtggacgt gagccacgaa   2220
gaccctgagg tcaagttcaa ctggtatgtt gacggcgtgg aggtgcataa tgccaagaca   2280
aagccgcggg aggagcagta caacagcacg taccgtgtgg tcagcgtcct caccgtcctg   2340
caccaggact ggctgaatgg caaggagtac aagtgcaagg tctccaacaa agccctccca   2400
gcccccatcg agaaaaccat ctccaaagcc aaagggcagc ccgagaaacc acaggtgtac   2460
accctgcccc catcccggga tgagctgacc aagaatcaag tcagcctgac ctgcctggtc   2520
aaaggcttct atcccagcga catcgccgtg gagtgggaga gcaatgggca gccggagaac   2580
aactacaaga ccacgcctcc cgtgctggac tccgacggct ccttcttcct ctactcaaaa   2640
ctcaccgtgg acaagagcag gtggcagcag gggaacgtct tctcatgctc cgtgatgcat   2700
gaggctctgc acaaccacta cacgcagaag agcctctccc tgtctccggg tcgaaaaaga   2760
agatcaggtt cgggtgcgcc agtaaagcag acattaaact tgatttgct gaaacttgca    2820 ggtgatgtag agtcaaatcc aggtccaatg caacaggga gccgaacctc tctgctcctt   2880
gctttcgggc tcctttgcct accgtggctc caagagggct cggcagaaat tgtgttgaca   2940
cagtctccag gcaccctgtc tttgtctcca ggggaaacag ccatcatctc ttgtcggacc   3000
agtcagtatg gttccttagc ctggtatcaa cagaggcccg gccaggcccc caggctcgtc   3060
```

```
atctattcgg gctctactcg ggccgctggc atcccagaca ggttcagcgg cagtcggtgg      3120
gggccagact acaatctcac catcagcaac ctggagtcgg gagattttgg tgtttattat      3180
tgccagcagt atgaattttt tggccagggg accaaggtcc aggtcgacat taaacgtacg      3240
gtggccgctc ccagcgtgtt catcttccct ccctctgatg aacagctgaa aagcggaaca      3300
gccagcgtgg tgtgtctgct gaacaacttc taccccagag aagccaaagt gcagtggaag      3360
gtggacaacg ccctgcagag cggaaacagc caggaaagcg tgacagagca ggattccaag      3420
gattccacat acagcctgag cagcacactg acactgtcca aggccgacta cgagaagcac      3480
aaggtgtacg cctgcgaagt gacacaccag ggactgtcct cccctgtgac aaagagcttc      3540
aacagaggag aatgctaaag gatccataac ttcgtatagc atacattata cgaagttatg      3600
atcctaatca acctctggat tacaaaattt gtgaaagatt gactggtatt cttaactatg      3660
ttgctccttt tacgctatgt ggatacgctg ctttaatgcc tttgtatcat gctattgctt      3720
cccgtatggc tttcattttc tcctccttgt ataaatcctg gttgctgtct ctttatgagg      3780
agttgtggcc cgttgtcagg caacgtggcg tggtgtgcac tgtgtttgct gacgcaaccc      3840
ccactggttg ggcattgcc accacctgtc agctcctttc cgggactttc gctttccccc      3900
tccctattgc cacggcggaa ctcatcgccg cctgccttgc ccgctgctgg acaggggctc      3960
ggctgttggg cactgacaat tccgtggtgt tgtcggggaa atcatcgtcc tttccggtac      4020
cataacttcg tatagcatac attatacgaa gttatttcga gcagacatga taagatacat      4080
tgatgagttt ggacaaacca caactagaat gcagtgaaaa aaatgcttta tttgtgaaat      4140
ttgtgatgct attgctttat tgtaaccat tataagctgc aataaacaag ttaacaacaa      4200
caattgcatt cattttatgt ttcaggttca gggggagatg tgggaggttt tttaaagcaa      4260
gtaaaacctc tacaaatgtg gtaaaatcaa gcttataact tcgtatagca tacattatac      4320
gaagttatag cttaggaacc cctagtgatg gagttggcca ctccctctct gcgcgctcgc      4380
tcgctcactg aggccgggcg accaaaggtc gcccgacgcc cgggctttgc ccgggcggcc      4440
tcagtgagcg agcgagcgcg cagagaggga gtggccaagc tagcgggcga ttaaggaaag      4500
ggctagatca ttcttgaaga cgaaagggcc tcgtgatacg cctattttta taggttaatg      4560
tcatgataat aatggtttct tagacgtcag gtggcacttt tcggggaaat gtgcgcggaa      4620
cccctatttg tttatttttc taaatacatt caaatatgta tccgctcatg agacaataac      4680
cctgataaat gcttcaataa tattgaaaaa ggaagagtat gagtattcaa catttccgtg      4740
tcgcccttat tcccttttt gcggcatttt gccttcctgt ttttgctcac ccagaaacgc      4800
tggtgaaagt aaaagatgct gaagatcagt tgggtgcacg agtgggttac atcgaactgg      4860
atctcaacag cggtaagatc cttgagagtt ttcgccccga agaacgtttt ccaatgatga      4920
gcacttttaa agttctgcta tgtggcgcgg tattatcccg tgttgacgcc gggcaagagc      4980
aactcggtcg ccgcatacac tattctcaga atgacttggt tgagtactca ccagtcacag      5040
aaaagcatct tacggatggc atgacagtaa agagaattatg cagtgctgcc ataaccatga      5100
gtgataacac tgcggccaac ttacttctga caacgatcgg aggaccgaag gagctaaccg      5160
cttttttgca caacatgggg gatcatgtaa ctcgccttga tcgttgggaa ccggagctga      5220
atgaagccat accaaacgac gagcgtgaca ccacgatgcc tgtagcaatg gcaacaacgt      5280
tgcgcaaact attaactggc gaactactta ctctagcttc ccggcaacaa ttaatagact      5340
ggatggaggc ggataaagtt gcaggaccac ttctgcgctc ggcccttccg gctggctggt      5400
ttattgctga taaatctgga gccggtgagc gtgggtctcg cggtatcatt gcagcactgg      5460
```

| | |
|---|---|
| ggccagatgg taagccctcc cgtatcgtag ttatctacac gacggggagt caggcaacta | 5520 |
| tggatgaacg aaatagacag atcgctgaga taggtgcctc actgattaag cattggtaac | 5580 |
| tgtcagacca agtttactca tatatacttt agattgattt aaaacttcat ttttaattta | 5640 |
| aaaggatcta ggtgaagatc cttttttgata atctcatgac caaaatccct aacgtgagt | 5700 |
| tttcgttcca ctgagcgtca gaccccgtag aaaagatcaa aggatcttct tgagatcctt | 5760 |
| ttttctgcg cgtaatctgc tgcttgcaaa caaaaaaacc accgctacca gcggtggttt | 5820 |
| gtttgccgga tcaagagcta ccaactcttt ttccgaaggt aactggcttc agcagagcgc | 5880 |
| agataccaaa tactgttctt ctagtgtagc cgtagttagg ccaccacttc aagaactctg | 5940 |
| tagcaccgcc tacatacctc gctctgctaa tcctgttacc agtggctgct gccagtggcg | 6000 |
| ataagtcgtg tcttaccggg ttggactcaa gacgatagtt accggataag cgcagcggt | 6060 |
| cgggctgaac ggggggttcg tgcacacagc ccagcttgga gcgaacgacc tacaccgaac | 6120 |
| tgagatacct acagcgtgag ctatgagaaa gcgccacgct cccgaaggg agaaaggcgg | 6180 |
| acaggtatcc ggtaagcggc agggtcggaa caggagagcg cacgagggag cttccagggg | 6240 |
| gaaacgcctg gtatctttat agtcctgtcg ggtttcgcca cctctgactt gagcgtcgat | 6300 |
| ttttgtgatg ctcgtcaggg gggcggagcc tatggaaaaa cgccagcaac gcggcctttt | 6360 |
| tacggttcct ggccttttgc tggccttttg ctcacatgta ataaacacac acaccaac | 6420 |
| aaccgtggtt ggttgttgtg ttggtttatt ctcgag | 6456 |

<210> SEQ ID NO 4
<211> LENGTH: 6468
<212> TYPE: DNA
<213> ORGANISM: Artificial Sequence
<220> FEATURE:
<223> OTHER INFORMATION: Vector 1835

<400> SEQUENCE: 4

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctactag ataacttcgt atagcataca ttatacgaag | 180 |
| ttatactagt ggagttccgc gttacataac ttacggtaaa tggcccgcct ggctgaccgc | 240 |
| ccaacgaccc ccgcccattg acgtcaataa tgacgtatgt tcccatagta acgccaatag | 300 |
| ggactttcca ttgacgtcaa tgggtggagt atttacggta aactgcccac ttggcagtac | 360 |
| atcaagtgta tcatatgcca agtacgcccc ctattgacgt caatgacggt aaatggcccg | 420 |
| cctggcatta tgcccagtac atgaccttat gggactttcc tacttggcag tacatctacg | 480 |
| tattagtcat cgctattacc atggtcgagg tgagccccac gttctgcttc actctcccca | 540 |
| tctccccccc ctccccaccc ccaattttgt atttatttat tttttaatta ttttgtgcag | 600 |
| cgatggggc gggggggggg ggggggcgcg cgccaggcgg ggcggggcgg ggcgagggc | 660 |
| ggggcgggc gaggcggaga ggtgcggcgg cagccaatca gagcggcgcg ctccgaaagt | 720 |
| ttccttttat ggcgaggcgg cggcggcggc ggccctataa aaagcgaagc gcgcggcggg | 780 |
| cgggagtcgc tgcgcgctgc cttcgccccg tgccccgctc cgccgccgcc tcgcgccgcc | 840 |
| cgccccggct ctgactgacc gcgttactaa acaggtaag tccataactt cgtatagcat | 900 |
| acattatacg aagttatggc ctccgcgccg gttttggcg cctcccgcgg gcgcccccct | 960 |
| cctcacggcg agcgctgcca cgtcagacga agggcgcagc gagcgtcctg atccttccgc | 1020 |

```
ccggacgctc aggacagcgg cccgctgctc ataagactcg gccttagaac cccagtatca    1080
gcagaaggac attttaggac gggacttggg tgactctagg cactggtttt tctttccaga    1140
gagcggaaca ggcgaggaaa agtagtccct tctcggcgat tctgcggagg gatctccgtg    1200
gggcggtgaa cgccgatgat ataacttcgt atagcataca ttatacgaag ttatgcctct    1260
actaaccatg ttcatgtttt cttttttttt ctacaggtcc tgggtgacga acaggcggcc    1320
gccatggcga cggttcaag aacttcccta cttcttgcat ttggcctgct ttgtttgccg    1380
tggttacagg agggctcggc acaggtgcga ctgtcgcagt ctggaggtca gatgaagaag    1440
cctggcgact cgatgagaat tcttgtcgg gcttcgggat acgaatttat taattgtcca    1500
ataaattgga ttcggctggc ccccggaaaa aggcctgagt ggatgggatg gatgaagcct    1560
agggggggggg ccgtcagtta cgcacgtcaa cttcagggca gagtgaccat gactcgagac    1620
atgtattccg agacagcctt tttggagctc cgttccttga catccgacga cacggccgtc    1680
tattttgta ctcggggaaa atattgcact gcgcgcgact attataattg ggacttcgaa    1740
cactggggcc agggcacccc ggtcaccgtc tcgtcagcga gcaccaaggg cccatcggtc    1800
ttccccctgg caccctcctc caagagcacc tctgggggca gcggccct gggctgcctg    1860
gtcaaggact acttccccga accggtgacg gtgtcgtgga actcaggcgc cctgaccagc    1920
ggcgtgcaca ccttcccggc tgtcctacag tcctcaggac tctactccct cagcagcgtg    1980
gtgaccgtgc cctccagcag cttgggcacc cagacctaca tctgcaacgt gaatcacaag    2040
cccagcaaca ccaaggtgga caagaaagtt gagcccaaat cttgtgacaa aactcacaca    2100
tgcccaccgt gcccagcacc tgaactcctg ggggaccgt cagtcttcct cttccccca    2160
aaacccaagg acaccctcat gatctcccgg acccctgagg tcacatgcgt ggtggtggac    2220
gtgagccacg aagaccctga ggtcaagttc aactggtatg ttgacggcgt ggaggtgcat    2280
aatgccaaga caaagccgcg ggaggagcag tacaacagca cgtaccgtgt ggtcagcgtc    2340
ctcaccgtcc tgcaccagga ctggctgaat ggcaaggagt acaagtgcaa ggtctccaac    2400
aaagccctcc cagcccccat cgagaaaacc atctccaaag ccaaagggca gccccgagaa    2460
ccacaggtgt acaccctgcc cccatcccgg gatgagctga ccaagaatca agtcagcctg    2520
acctgcctgg tcaaaggctt ctatcccagc gacatcgccg tggagtggga gagcaatggg    2580
cagccggaga caactacaa gaccacgcct cccgtgctgg actccgacgg ctccttcttc    2640
ctctactcaa aactcaccgt ggacaagagc aggtggcagc aggggaacgt cttctcatgc    2700
tccgtgatgc atgaggctct gcacaaccac tacacgcaga agagcctctc cctgtctccg    2760
ggtcgaaaaa gaagatcagg ttcgggtgcg ccagtaaagc agacattaaa ctttgatttg    2820
ctgaaacttg caggtgatgt agagtcaaat ccaggtccaa tggcaacagg agccgaacc    2880
tctctgctcc ttgctttcgg gctcctttgc ctaccgtggc tccaagaggg ctcggcagaa    2940
attgtgttga cacagtctcc aggcaccctg tctttgtctc caggggaaac agccatcatc    3000
tcttgtcgga ccagtcagta tggttcctta gcctggtatc aacagaggcc cggccaggcc    3060
cccaggctcg tcatctattc gggctctact cgggccgctg gcatcccaga caggttcagc    3120
ggcagtcggt gggggccaga ctacaatctc accatcagca acctggagtc gggagatttt    3180
ggtgtttatt attgccagca gtatgaattt tttggccagg ggaccaaggt ccaggtcgac    3240
attaaacgta cggtggccgc tcccagcgtg ttcatcttcc ctccctctga tgaacagctg    3300
aaaagcggaa cagccagcgt ggtgtgtctg ctgaacaact tctaccccag agaagccaaa    3360
gtgcagtgga aggtggacaa cgccctgcag agcggaaaca gccaggaaag cgtgacagag    3420
```

```
caggattcca aggattccac atacagcctg agcagcacac tgacactgtc caaggccgac    3480
tacgagaagc acaaggtgta cgcctgcgaa gtgacacacc agggactgtc ctcccctgtg    3540
acaaagagct tcaacagagg agaatgctaa aggatccata acttcgtata gcatacatta    3600
tacgaagtta tgatcctaat caacctctgg attacaaaat ttgtgaaaga ttgactggta    3660
ttcttaacta tgttgctcct tttacgctat gtggatacgc tgctttaatg cctttgtatc    3720
atgctattgc ttcccgtatg gctttcattt tctcctcctt gtataaatcc tggttgctgt    3780
ctctttatga ggagttgtgg cccgttgtca ggcaacgtgg cgtggtgtgc actgtgtttg    3840
ctgacgcaac ccccactggt tggggcattg ccaccacctg tcagctcctt ccgggactt    3900 tcgctttccc cctccctatt gccacggcgg aactcatcgc cgcctgcctt gcccgctgct    3960
ggacaggggc tcggctgttg ggcactgaca attccgtggt gttgtcgggg aaatcatcgt    4020
cctttccggt accataactt cgtatagcat acattatacg aagttatttc gagcagacat    4080
gataagatac attgatgagt ttggacaaac cacaactaga atgcagtgaa aaaaatgctt    4140
tatttgtgaa atttgtgatg ctattgcttt atttgtaacc attataagct gcaataaaca    4200
agttaacaac aacaattgca ttcattttat gtttcaggtt caggggagga gtgtgggaggt   4260 tttttaaagc aagtaaaacc tctacaaatg tggtaaaatc aagcttataa cttcgtatag    4320
catacattat acgaagttat agcttaggaa cccctagtga tggagttggc cactccctct    4380
ctgcgcgctc gctcgctcac tgaggccggg cgaccaaagg tcgcccgacg cccgggcttt    4440
gcccgggcgg cctcagtgag cgagcgagcg cgcagagagg gagtggccaa gctagcgggc    4500
gattaaggaa agggctagat cattcttgaa gacgaaaggg cctcgtgata cgcctatttt    4560
tataggttaa tgtcatgata taatggtttc ttagacgtc aggtggcact tttcggggaa     4620
atgtgcgcgg aacccctatt tgtttatttt tctaaataca ttcaaatatg tatccgctca    4680
tgagacaata accctgataa atgcttcaat aatattgaaa aaggaagagt atgagtattc    4740
aacatttccg tgtcgccctt attcccttt ttgcggcatt ttgccttcct gtttttgctc      4800
acccagaaac gctggtgaaa gtaaaagatg ctgaagatca gttgggtgca cgagtgggtt    4860
acatcgaact ggatctcaac agcggtaaga tccttgagag ttttcgcccc gaagaacgtt    4920
ttccaatgat gagcactttt aaagttctgc tatgtggcgc ggtattatcc cgtgttgacg    4980
ccgggcaaga gcaactcggt cgccgcatac actattctca gaatgacttg gttgagtact    5040
caccagtcac agaaaagcat cttacggatg gcatgacagt aagagaatta tgcagtgctg    5100
ccataaccat gagtgataac actgcggcca acttacttct gacaacgatc ggaggaccga    5160
aggagctaac cgcttttttg cacaacatgg gggatcatgt aactcgcctt gatcgttggg    5220
aaccggagct gaatgaagcc ataccaaacg acgagcgtga ccacgatg cctgtagcaa     5280 tggcaacaac gttgcgcaaa ctattaactg gcgaactact tactctagct tcccggcaac    5340
aattaataga ctggatggag gcggataaag ttgcaggacc acttctgcgc tcggcccttc    5400
cggctggctg gtttattgct gataaatctg gagccggtga gcgtgggtct cgcggtatca    5460
ttgcagcact ggggccagat ggtaagccct cccgtatcgt agttatctac acgacgggga    5520
gtcaggcaac tatggatgaa cgaaatagac agatcgctga gataggtgcc tcactgatta    5580
agcattggta actgtcagac caagtttact catatatact ttagattgat ttaaaacttc    5640
atttttaatt taaaaggatc taggtgaaga tcctttttga taatctcatg accaaaatcc    5700
cttaacgtga gttttcgttc cactgagcgt cagacccgt agaaaagatc aaaggatctt    5760
```

```
cttgagatcc ttttttttctg cgcgtaatct gctgcttgca acaaaaaaaa ccaccgctac    5820
cagcggtggt ttgtttgccg gatcaagagc taccaactct ttttccgaag gtaactggct    5880
tcagcagagc gcagatacca atactgttc ttctagtgta gccgtagtta ggccaccact     5940
tcaagaactc tgtagcaccg cctacatacc tcgctctgct aatcctgtta ccagtggctg    6000
ctgccagtgg cgataagtcg tgtcttaccg ggttggactc aagacgatag ttaccggata    6060
aggcgcagcg gtcgggctga acgggggggtt cgtgcacaca gcccagcttg gagcgaacga   6120
cctacaccga actgagatac ctacagcgtg agctatgaga aagcgccacg cttcccgaag    6180
ggagaaaggc ggacaggtat ccggtaagcg gcagggtcgg aacaggagag cgcacgaggg    6240
agcttccagg gggaaacgcc tggtatcttt atagtcctgt cgggtttcgc cacctctgac    6300
ttgagcgtcg atttttgtga tgctcgtcag gggggcggag cctatggaaa aacgccagca    6360
acgcggcctt tttacggttc ctggccttt gctggccttt tgctcacatg taataaacac     6420
acacacacca caaccgtgg ttggttgttg tgttggttta ttctcgag                   6468
```

<210> SEQ ID NO 5
<211> LENGTH: 86
<212> TYPE: PRT
<213> ORGANISM: Artificial Sequence
<220> FEATURE:
<223> OTHER INFORMATION: HIV-1 tat

<400> SEQUENCE: 5

```
Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
            85
```

<210> SEQ ID NO 6
<211> LENGTH: 11
<212> TYPE: PRT
<213> ORGANISM: Artificial Sequence
<220> FEATURE:
<223> OTHER INFORMATION: Residues 47-57 of TAT

<400> SEQUENCE: 6

```
Tyr Gly Arg Lys Lys Arg Arg Gln Arg Arg Arg
 1               5                  10
```

<210> SEQ ID NO 7
<211> LENGTH: 16
<212> TYPE: PRT
<213> ORGANISM: Artificial Sequence
<220> FEATURE:
<223> OTHER INFORMATION: Penetratin

<400> SEQUENCE: 7

```
Arg Gln Ile Lys Ile Trp Phe Gln Asn Arg Arg Met Lys Trp Lys Lys
 1               5                  10                  15
```

<210> SEQ ID NO 8
<211> LENGTH: 10
<212> TYPE: PRT
<213> ORGANISM: Artificial Sequence
<220> FEATURE:
<223> OTHER INFORMATION: Tat

<400> SEQUENCE: 8

Tyr Gly Arg Lys Lys Arg Arg Gln Arg Arg
1               5                   10

<210> SEQ ID NO 9
<211> LENGTH: 26
<212> TYPE: PRT
<213> ORGANISM: Artificial Sequence
<220> FEATURE:
<223> OTHER INFORMATION: VT5

<400> SEQUENCE: 9

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 10
<211> LENGTH: 18
<212> TYPE: PRT
<213> ORGANISM: Artificial Sequence
<220> FEATURE:
<223> OTHER INFORMATION: MAP

<400> SEQUENCE: 10

Lys Leu Ala Leu Lys Leu Ala Leu Lys Ala Leu Lys Ala Ala Leu Lys
1               5                   10                  15

Leu Ala

<210> SEQ ID NO 11
<211> LENGTH: 27
<212> TYPE: PRT
<213> ORGANISM: Artificial Sequence
<220> FEATURE:
<223> OTHER INFORMATION: Transportan

<400> SEQUENCE: 11

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 12
<211> LENGTH: 21
<212> TYPE: PRT
<213> ORGANISM: Artificial Sequence
<220> FEATURE:
<223> OTHER INFORMATION: Transportan-10

<400> SEQUENCE: 12

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 13
<211> LENGTH: 18
<212> TYPE: PRT

```
<213> ORGANISM: Artificial Sequence
<220> FEATURE:
<223> OTHER INFORMATION: pVEC

<400> SEQUENCE: 13

Leu Leu Ile Ile Leu Arg Arg Arg Ile Arg Lys Gln Ala His Ala His
1               5                   10                  15

Ser Lys

<210> SEQ ID NO 14
<211> LENGTH: 16
<212> TYPE: PRT
<213> ORGANISM: Artificial Sequence
<220> FEATURE:
<223> OTHER INFORMATION: pISL

<400> SEQUENCE: 14

Arg Val Ile Arg Val Trp Phe Gln Asn Lys Arg Cys Lys Asp Lys Lys
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: (R)7

<400> SEQUENCE: 15

Arg Arg Arg Arg Arg Arg Arg
1               5

<210> SEQ ID NO 16
<211> LENGTH: 21
<212> TYPE: PRT
<213> ORGANISM: Artificial Sequence
<220> FEATURE:
<223> OTHER INFORMATION: Pep-1

<400> SEQUENCE: 16

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 17
<211> LENGTH: 28
<212> TYPE: PRT
<213> ORGANISM: Artificial Sequence
<220> FEATURE:
<223> OTHER INFORMATION: Mouse PrP (1-28)

<400> SEQUENCE: 17

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 18
<211> LENGTH: 34
<212> TYPE: DNA
<213> ORGANISM: Artificial Sequence
<220> FEATURE:
<223> OTHER INFORMATION: loxP

<400> SEQUENCE: 18
```

```
ataacttcgt atagcataca ttatacgaag ttat                          34

<210> SEQ ID NO 19
<211> LENGTH: 34
<212> TYPE: DNA
<213> ORGANISM: Artificial Sequence
<220> FEATURE:
<223> OTHER INFORMATION: Lox2272

<400> SEQUENCE: 19
ataacttcgt ataaagtatc ctatacgaag ttat                          34

<210> SEQ ID NO 20
<211> LENGTH: 34
<212> TYPE: DNA
<213> ORGANISM: Artificial Sequence
<220> FEATURE:
<223> OTHER INFORMATION: LoxN

<400> SEQUENCE: 20
ataacttcgt atagtatacc ttatacgaag ttat                          34

<210> SEQ ID NO 21
<211> LENGTH: 34
<212> TYPE: DNA
<213> ORGANISM: Artificial Sequence
<220> FEATURE:
<223> OTHER INFORMATION: FLP recombinase target (FRT)

<400> SEQUENCE: 21
gaagttccta ttctctagaa agtataggaa cttc                          34

<210> SEQ ID NO 22
<211> LENGTH: 48
<212> TYPE: DNA
<213> ORGANISM: Artificial Sequence
<220> FEATURE:
<223> OTHER INFORMATION: variant FRT

<400> SEQUENCE: 22
gaagttccta ttccgaagtt cctattctct agaaagtata ggaacttc           48

<210> SEQ ID NO 23
<211> LENGTH: 367
<212> TYPE: DNA
<213> ORGANISM: Artificial Sequence
<220> FEATURE:
<223> OTHER INFORMATION: Chicken beta-actin promoter used in CASI
      promoter

<400> SEQUENCE: 23
tggtcgaggt gagccccacg ttctgcttca ctctccccat ctcccccccc tccccacccc    60
caattttgta tttatttatt ttttaattat tttgtgcagc gatgggggcg ggggggggg    120 ggggcgcgc gccaggcggg gcggggcggg gcgaggggcg gggcggggcg aggcggagag    180
gtgcggcggc agccaatcag agcggcgcgc tccgaaagtt ccttttatg gcgaggcggc    240 ggcggcggcg gccctataaa aagcgaagcg cgcggcgggc gggagtcgct gcgcgctgcc    300
ttcgccccgt gccccgctcc gccgccgcct cgcgccgccc gccccggctc tgactgaccg    360
cgttact                                                           367

<210> SEQ ID NO 24
<211> LENGTH: 300
<212> TYPE: DNA
```

<213> ORGANISM: Artificial Sequence
<220> FEATURE:
<223> OTHER INFORMATION: UBC enhancer used in CASI promoter

<400> SEQUENCE: 24

```
gcctccgcgc cgggttttgg cgcctcccgc gggcgccccc ctcctcacgg cgagcgctgc      60
cacgtcagac gaagggcgca gcgagcgtcc tgatccttcc gcccggacgc tcaggacagc     120
ggcccgctgc tcataagact cggccttaga accccagtat cagcagaagg acattttagg     180
acgggacttg ggtgactcta gggcactggt tttctttcca gagagcggaa caggcgagga     240
aaagtagtcc cttctcggcg attctgcgga gggatctccg tggggcggtg aacgccgatg     300
```

<210> SEQ ID NO 25
<211> LENGTH: 1124
<212> TYPE: DNA
<213> ORGANISM: Artificial Sequence
<220> FEATURE:
<223> OTHER INFORMATION: CASI promoter

<400> SEQUENCE: 25

```
ggagttccgc gttacataac ttacggtaaa tggcccgcct ggctgaccgc ccaacgaccc      60
ccgcccattg acgtcaataa tgacgtatgt tcccatagta acgccaatag ggactttcca     120
ttgacgtcaa tgggtggagt atttacggta aactgcccac ttggcagtac atcaagtgta     180
tcatatgcca agtacgcccc ctattgacgt caatgacggt aaatggcccg cctggcatta     240
tgcccagtac atgaccttat gggactttcc tacttggcag tacatctacg tattagtcat     300
cgctattacc atggtcgagg tgagcccac gttctgcttc actctcccca tctccccccc     360
ctccccaccc ccaattttgt atttatttat tttttaatta ttttgtgcag cgatgggggc     420
gggggggggg gggggcgcg cgccaggcgg ggcggggcgg ggcgagggc ggggcggggc     480
gaggcggaga ggtgcggcgg cagccaatca gagcggcgcg ctccgaaagt tcctttttat     540
ggcgaggcgg cggcggcggc ggccctataa aaagcgaagc gcgcggcggg cgggagtcgc     600
tgcgcgctgc cttcgccccg tgccccgctc cgccgccgcc tcgcgccgcc cgccccggct     660
ctgactgacc gcgttactaa aacaggtaag tccataactt cgtatagcat acattatacg     720
aagttatggc ctccgcgccg ggttttggcg cctcccgcgg gcgcccccct cctcacggcg     780
agcgctgcca cgtcagacga agggcgcagc gagcgtcctg atccttccgc ccggacgctc     840
aggacagcgg cccgctgctc ataagactcg gccttagaac cccagtatca gcagaaggac     900
attttaggac gggacttggg tgactctagg gcactggttt ctttccaga gagcggaaca     960
ggcgaggaaa agtagtccct tctcggcgat tctgcggagg gatctccgtg gggcggtgaa    1020
cgccgatgat ataacttcgt atagcataca ttatacgaag ttatgcctct actaaccatg    1080
ttcatgtttt ctttttttt ctacaggtcc tgggtgacga acag                     1124
```

<210> SEQ ID NO 26
<211> LENGTH: 233
<212> TYPE: DNA
<213> ORGANISM: Artificial Sequence
<220> FEATURE:
< 223> OTHER INFORMATION: SV40 late poly(A)

<400> SEQUENCE: 26

```
ttcgagcaga catgataaga tacattgatg agtttggaca aaccacaact agaatgcagt      60
gaaaaaaatg ctttatttgt gaaatttgtg atgctattgc tttatttgta accattataa     120
gctgcaataa acaagttaac aacaacaatt gcattcattt tatgtttcag gttcaggggg     180
```
agatgtggga ggttttttaa agcaagtaaa acctctacaa atgtggtaaa atc          233

<210> SEQ ID NO 27
<211> LENGTH: 592
<212> TYPE: DNA
<213> ORGANISM: Artificial Sequence
<220> FEATURE:
<223> OTHER INFORMATION: Woodchuck hepatitis virus posttranscriptional
      regulatory element

<400> SEQUENCE: 27
taatcaacct ctggattaca aaatttgtga aagattgact ggtattctta actatgttgc    60
tccttttacg ctatgtggat acgctgcttt aatgcctttg tatcatgcta ttgcttcccg   120
tatggctttc attttctcct ccttgtataa atcctggttg ctgtctcttt atgaggagtt   180
gtggcccgtt gtcaggcaac gtggcgtggt gtgcactgtg tttgctgacg caacccccac   240
tggttggggc attgccacca cctgtcagct cctttccggg actttcgctt tccccctccc   300
tattgccacg gcggaactca tcgccgcctg ccttgcccgc tgctggacag gggctcggct   360
gttgggcact gacaattccg tggtgttgtc ggggaaatca tcgtcctttc cttggctgct   420
cgcctgtgtt gccacctgga ttctgcgcgg gacgtccttc tgctacgtcc cttcggccct   480
caatccagcg gaccttcctt cccgcggcct gctgccggct ctgcggcctc ttccgcgtct   540
tcgccttcgc cctcagacga gtcggatctc cctttgggcc gcctccccgc ct          592

<210> SEQ ID NO 28
<211> LENGTH: 411
<212> TYPE: DNA
<213> ORGANISM: Artificial Sequence
<220> FEATURE:
<223> OTHER INFORMATION: "no X" WPRE

<400> SEQUENCE: 28
taatcaacct ctggattaca aaatttgtga aagattgact ggtattctta actatgttgc    60
tccttttacg ctatgtggat acgctgcttt aatgcctttg tatcatgcta ttgcttcccg   120
tatggctttc attttctcct ccttgtataa atcctggttg ctgtctcttt atgaggagtt   180
gtggcccgtt gtcaggcaac gtggcgtggt gtgcactgtg tttgctgacg caacccccac   240
tggttggggc attgccacca cctgtcagct cctttccggg actttcgctt tccccctccc   300
tattgccacg gcggaactca tcgccgcctg ccttgcccgc tgctggacag gggctcggct   360
gttgggcact gacaattccg tggtgttgtc ggggaaatca tcgtcctttc c            411

<210> SEQ ID NO 29
<211> LENGTH: 504
<212> TYPE: DNA
<213> ORGANISM: Artificial Sequence
<220> FEATURE:
<223> OTHER INFORMATION: short WPRE

<400> SEQUENCE: 29
taatcaacct ctggattaca aaatttgtga aagattgact ggtattctta actatgttgc    60
tccttttacg ctatgtggat acgctgcttt aatgcctttg tatcatgcta ttgcttcccg   120
tatggctttc attttctcct ccttgtataa atcctggttg ctgtctcttt atgaggagtt   180
gtggcccgtt gtcaggcaac gtggcgtggt gtgcactgtg tttgctgacg caacccccac   240
tggttggggc attgccacca cctgtcagct cctttccggg actttcgctt tccccctccc   300
tattgccacg gcggaactca tcgccgcctg ccttgcccgc tgctggacag gggctcggct   360

```
gttgggcact gacaattccg tggtgttgtc ggggaaatca tcgtcctttc cttggctgct      420
cgcctgtgtt gccacctgga ttctgcgcgg gacgtccttc tgctacgtcc cttcggccct      480
caatccagcg gaccttcctt cccg                                             504
```

<210> SEQ ID NO 30
<211> LENGTH: 84
<212> TYPE: DNA
<213> ORGANISM: Artificial Sequence
<220> FEATURE:
<223> OTHER INFORMATION: F2A sequence having a standard furin cleavage
      site

<400> SEQUENCE: 30

```
cgggctaaga gagcaccggt gaaacagact ttgaattttg accttctcaa gttggcggga      60
gacgtggagt ccaacccagg gccc                                             84
```

<210> SEQ ID NO 31
<211> LENGTH: 96
<212> TYPE: DNA
<213> ORGANISM: Artificial Sequence
<220> FEATURE:
<223> OTHER INFORMATION: F2A sequence having a modified furin cleavage
      site

<400> SEQUENCE: 31

```
cgaaaaagaa gatcaggttc gggtgcgcca gtaaagcaga cattaaactt tgatttgctg      60
aaacttgcag gtgatgtaga gtcaaatcca ggtcca                                96
```

<210> SEQ ID NO 32
<211> LENGTH: 4
<212> TYPE: PRT
<213> ORGANISM: Artificial Sequence
<220> FEATURE:
<223> OTHER INFORMATION: Protease target site comprising a furin
      cleavage site
<220> FEATURE:
<221> NAME/KEY: VARIANT
<222> LOCATION: 2
<223> OTHER INFORMATION: Xaa = any amino acid
<220> FEATURE:
<221> NAME/KEY: VARIANT
<222> LOCATION: 3
<223> OTHER INFORMATION: Xaa = any amino acid, preferably Lys or Arg

<400> SEQUENCE: 32

Arg Xaa Xaa Arg
 1

<210> SEQ ID NO 33
<211> LENGTH: 20
<212> TYPE: PRT
<213> ORGANISM: Artificial Sequence
<220> FEATURE:
<223> OTHER INFORMATION: F2A, wild-type 2A polypeptide from
      foot-and-mouth disease virus

<400> SEQUENCE: 33

Gln Leu Leu Asn Phe Asp Leu Leu Lys Leu Ala Gly Asp Val Glu Ser
 1               5                  10                  15

Asn Pro Gly Pro
            20

<210> SEQ ID NO 34
<211> LENGTH: 20

```
<212> TYPE: PRT
<213> ORGANISM: Artificial Sequence
<220> FEATURE:
<223> OTHER INFORMATION: F2A(wt)

<400> SEQUENCE: 34

Gln Leu Leu Asn Phe Asp Leu Leu Lys Leu Ala Gly Asp Val Glu Ser
1               5                   10                  15

Asn Pro Gly Pro
            20

<210> SEQ ID NO 35
<211> LENGTH: 18
<212> TYPE: PRT
<213> ORGANISM: Artificial Sequence
<220> FEATURE:
<223> OTHER INFORMATION: F2A(-2)

<400> SEQUENCE: 35

Leu Asn Phe Asp Leu Leu Lys Leu Ala Gly Asp Val Glu Ser Asn Pro
1               5                   10                  15

Gly Pro

<210> SEQ ID NO 36
<211> LENGTH: 19
<212> TYPE: PRT
<213> ORGANISM: Artificial Sequence
<220> FEATURE:
<223> OTHER INFORMATION: F2A(-1)

<400> SEQUENCE: 36

Leu Leu Asn Phe Asp Leu Leu Lys Leu Ala Gly Asp Val Glu Ser Asn
1               5                   10                  15

Pro Gly Pro

<210> SEQ ID NO 37
<211> LENGTH: 13
<212> TYPE: PRT
<213> ORGANISM: Artificial Sequence
<220> FEATURE:
<223> OTHER INFORMATION: F2A(-7)

<400> SEQUENCE: 37

Leu Lys Leu Ala Gly Asp Val Glu Ser Asn Pro Gly Pro
1               5                   10

<210> SEQ ID NO 38
<211> LENGTH: 20
<212> TYPE: PRT
<213> ORGANISM: Artificial Sequence
<220> FEATURE:
<223> OTHER INFORMATION: F2A(19)

<400> SEQUENCE: 38

Gln Leu Leu Asn Phe Asp Leu Leu Lys Leu Ala Gly Asp Val Glu Ser
1               5                   10                  15

Asn Pro Ala Pro
            20

<210> SEQ ID NO 39
<211> LENGTH: 20
<212> TYPE: PRT
<213> ORGANISM: Artificial Sequence
<220> FEATURE:
<223> OTHER INFORMATION: I2A(0)
```

```
<400> SEQUENCE: 39

Thr Arg Ala Glu Ile Glu Asp Glu Leu Ile Arg Arg Gly Ile Glu Ser
1               5                   10                  15

Asn Pro Gly Pro
            20

<210> SEQ ID NO 40
<211> LENGTH: 20
<212> TYPE: PRT
<213> ORGANISM: Artificial Sequence
<220> FEATURE:
<223> OTHER INFORMATION: I2A(1)

<400> SEQUENCE: 40

Thr Arg Ala Glu Ile Glu Asp Glu Leu Ile Arg Ala Gly Ile Glu Ser
1               5                   10                  15

Asn Pro Gly Pro
            20

<210> SEQ ID NO 41
<211> LENGTH: 20
<212> TYPE: PRT
<213> ORGANISM: Artificial Sequence
<220> FEATURE:
<223> OTHER INFORMATION: I2A(2)

<400> SEQUENCE: 41

Thr Arg Ala Glu Ile Glu Asp Glu Leu Ile Arg Arg Gly Ile Glu Ser
1               5                   10                  15

Asn Pro Gly Pro
            20

<210> SEQ ID NO 42
<211> LENGTH: 20
<212> TYPE: PRT
<213> ORGANISM: Artificial Sequence
<220> FEATURE:
<223> OTHER INFORMATION: I2A(3)

<400> SEQUENCE: 42

Thr Arg Ala Glu Ile Glu Asp Glu Leu Ile Arg Arg Gly Ile Glu Ser
1               5                   10                  15

Asn Pro Ala Pro
            20

<210> SEQ ID NO 43
<211> LENGTH: 49
<212> TYPE: DNA
<213> ORGANISM: Artificial Sequence
<220> FEATURE:
<223> OTHER INFORMATION: Synthetic polyA sequence

<400> SEQUENCE: 43
aataaaatat ctttattttc attacatctg tgtgttggtt ttttgtgtg          49
```

REVERSIBLE GENE EXPRESSION

CROSS-REFERENCE TO RELATED APPLICATIONS

The present application claims the benefit of U.S. Provisional App. No. 61/721,365 filed Nov. 1, 2012, and U.S. Provisional App. No. 61/779,987, filed Mar. 13, 2013, each of which is hereby incorporated by reference in its entirety. This present application is related to U.S. application Ser. No. 13/400,945, filed Feb. 12, 2012.

STATEMENT REGARDING FEDERALLY SPONSORED R&D

This invention was made with government support under HHSN261200800001E awarded by the National Institutes of Health. The government has certain rights in the invention.

REFERENCE TO SEQUENCE LISTING, TABLE, OR COMPUTER PROGRAM LISTING

The present application is being filed along with a Sequence Listing in electronic format. The Sequence Listing is provided as a file CALTE092A_SEQLIST.TXT, created and last modified on Oct. 28, 2013, which is 44,659 bytes in size, and updated by a file CALTE092A REPLACEMENT.TXT, created and last modified on Jan. 10, 2014, which is 44,663 bytes in size. The information in the electronic format of the Sequence Listing is incorporated herein by reference in its entirety.

FIELD

Embodiments herein relate generally to inducible gene expression systems and methods expressing gene products.

SUMMARY

In some embodiments, an inducible expression system for gene products is provided. The system can comprise a first adeno-associated virus vector comprising a first ITR, a promoter positioned 3' to the first ITR, a first recombinase target site positioned 3' to the first ITR and 5' to a 3' end of the promoter, a second recombinase target site positioned 3' to a 5' end of the promoter, an insertion site positioned 3' to the promoter and 3' to the second recombinase target site, such that the promoter would be operably linked to at least an inserted polynucleotide, a third recombinase target site positioned 3' to the insertion site, and a second ITR positioned 3' to the third recombinase target site. In some embodiments, the first, second, and third recombinase target sites are oriented in the same direction. The system can include a source of a recombinase configured to induce recombination events between two or more of the recombinase target sites. In some embodiments, the source of recombinase comprises a second vector comprising a promoter operably linked to a recombinase polynucleotide encoding the recombinase. In some embodiments, the second vector comprises one of an adeno-associated virus vector, or an adenovirus vector. In some embodiments, the source of recombinase comprises a recombinase polypeptide fused to a cell-penetration peptide. In some embodiments, the first adeno-associated virus vector further comprises a WPRE positioned 3' to the insertion site and 5' to the second ITR, a fourth recombinase target site positioned 3' to the insertion site and 5' to a 3' end of the WPRE, a fifth recombinase target site positioned 3' to the fourth recombinase target site, and 3' to a 5' end of the WPRE, and a sixth recombinase target site positioned 3' of the first recombinase target site and 5' of the second recombinase target site. In some embodiments, the fourth, fifth, and sixth recombinase target sites are oriented in the same direction. In some embodiments, the third recombinase target site is positioned 3' to the WPRE and 5' to the second ITR. In some embodiments, the promoter comprises a synthetic intron comprising a splice donor, a transcriptional enhancer positioned 3' to the splice donor, and a splice acceptor positioned 3' to the splice donor, in which the first recombinase target and second recombinase target flank the synthetic intron. In some embodiments, the recombinase target sites of the AAV vector of the expression system comprise Lox sites and the recombinase comprises Cre. In some embodiments, the recombinase target sites of the AAV vector of the expression system comprise FRT sites and the recombinase comprises FLPase. In some embodiments, the first, second, and third recombinase target sites are identical to each other. In some embodiments, the fourth, fifth, and sixth recombinase target sites are identical to each other. In some embodiments, the first, second, third, fourth, fifth, and sixth recombinase target sites are identical to each other. In some embodiments, the first adeno-associated vector further comprises a cleavage polynucleotide positioned 3' to the third recombinase target site. In some embodiments, the WPRE comprises the polynucleotide sequence of SEQ ID NO: 27, SEQ ID NO: 28, or SEQ ID NO: 29. In some embodiments, the adeno-associated vector further comprises a polyadenylation sequence positioned 3' of the WPRE and 5' of the third recombinase target site. In some embodiments, the polyadenylation sequence comprises the polynucleotide sequence of SEQ ID NO: 26, or SEQ ID NO: 43. In some embodiments, the first, second, third, fourth, fifth, and sixth recombinase target sites are oriented in the same direction. In some embodiments, the first, second, and third recombinase target sites are oriented in a direction opposite the fourth, fifth, and sixth recombinase target sites. In some embodiments, the first adeno-associated virus vector further comprises a WPRE positioned 3' to the insertion site and 5' to the second ITR, a fourth recombinase target site positioned 3' to the first polynucleotide and 5' to a 3' end of the WPRE, a fifth recombinase target site positioned 3' to the fourth recombinase target site, and 3' to a 5' end of the WPRE. In some embodiments, the fourth and fifth recombinase target sites are oriented in the same direction. In some embodiments, the third recombinase target site is positioned 3' to the WPRE and 5' to the second ITR. In some embodiments, the first, second, third, fourth, and fifth recombinase target sites are oriented in the same direction.

In some embodiments, a method of conditionally expressing at least a first gene product in a mammal is provided. The method can comprise administering to the mammal a first adeno-associated virus vector comprising a first ITR, a promoter positioned 3' to the first ITR, a first recombinase target site positioned 3' to the first ITR and 5' to a 3' end of the promoter, a second recombinase target site positioned 3' to a 5' end of the promoter, and a first polynucleotide encoding a first gene product, in which the first polynucleotide is positioned 3' to the promoter and 3' to the second recombinase target site, and in which the promoter is operably linked to the first polynucleotide, a third recombinase target site positioned 3' to the first polynucleotide, and a second ITR positioned 3' to the third recombinase target site, in which the first, second, and third recombinase target sites are oriented in the same direction. After administration of the first adeno-associated virus vector, the first gene product can be expressed in the mammal. The method can further comprise administering a recombinase to the mammal, so that the recombinase induces recombination between at least two of the recombinase target sites after the first gene product is expressed, thus reducing expression of the first gene product. In some embodiments, administering the recombinase comprises administering a second vector to the mammal, in which the second vector comprises a promoter operably linked to a recombinase polynucleotide encoding the recombinase. In some embodiments, expression of the recombinase polynucleotide is induced after the first gene product is expressed, thus reducing expression of the first gene product. In some embodiments, the recombinase is administered after the first adeno-associated virus vector, thereby reducing expression of the first gene product. In some embodiments, administering the recombinase comprises contacting at least one cell of the mammal with the recombinase fused to a cell-penetration polypeptide. In some embodiments, the recombinase target sites comprise Lox sites and the recombinase comprises Cre. In some embodiments, the recombinase target sites comprise FRT sites and the recombinase comprises FLPase. In some embodiments, the first gene product comprises at least a heavy chain or a light chain of an immunoglobulin. In some embodiments, the first adeno-associated virus vector further comprises a cleavage polynucleotide positioned 3' of the first polynucleotide, and a second polynucleotide encoding a second gene product positioned 3' of the cleavage polynucleotide. In some embodiments, the first adeno-associated virus vector further comprises a WPRE positioned 3' to the insertion site and 5' to the second ITR, a fourth recombinase target site positioned 3' to the first polynucleotide and 5' to a 3' end of the WPRE, a fifth recombinase target site positioned 3' to the fourth recombinase target site, and 3' to a 5' end of the WPRE, and a sixth recombinase target site positioned 3' of the first recombinase target site and 5' of the second recombinase target site. In some embodiments, the fourth, fifth, and sixth recombinase target sites are oriented in the same direction. In some embodiments, the third recombinase target site is positioned 3' to the WPRE and 5' to the second ITR. In some embodiments, the recombinase induces recombination events involving the first, second, third, fourth, fifth, and sixth recombinase target sites, thereby excising at least a portion of the first adeno-associated virus vector. In some embodiments, the first adeno-associated virus vector further comprises a WPRE positioned 3' to the insertion site and 5' to the second ITR, a fourth recombinase target site positioned 3' to the first polynucleotide and 5' to a 3' end of the WPRE, a fifth recombinase target site positioned 3' to the fourth recombinase target site, and 3' to a 5' end of the WPRE. In some embodiments, the fourth and fifth recombinase target sites are oriented in the same direction. In some embodiments, the third recombinase target site is positioned 3' to the WPRE and 5' to the second ITR. In some embodiments, the recombinase induces recombination events involving the first, second, third, fourth, and fifth recombinase target sites, thereby excising at least a portion of the first adeno-associated virus vector.

In some embodiments, expression of the first gene product is reduced at least 10-fold. In some embodiments, the mammal is a mouse. In some embodiments, the mammal is a human

BRIEF DESCRIPTION OF THE DRAWINGS

FIG. 1A is a schematic diagram illustrating an adeno-associated vector for expressing a gene product of interest in accordance with some embodiments herein. Solid arrows indicate recombinase target sites and their relative orientations.

FIG. 1B is a schematic diagram illustrating promoter region for expressing a gene product of interest in accordance with some embodiments herein. Recombinase target sites (and relative orientations) are depicted as solid arrows.

FIG. 2A is a schematic diagram of an adeno-associated vector for expressing a gene product of interest in accordance with some embodiments herein.

FIG. 2B is a graph illustrating luciferase activity in 293T cells with adeno-associated virus (AAV) constructs according to some embodiments herein. The AAV constructs were based on the vector of FIG. 2A and contained one loxP site. Luciferase activity for each construct was observed in the absence of CRE (i.e., pUC) and the presence or CRE.

FIG. 2C is a schematic diagram illustrating the position of the loxP site for each of the constructs used in the experiment depicted in FIG. 2B. For each experiment (e.g. each pair of bars) in FIG. 2B, the corresponding construct schematic is shown in FIG. 2C to the right of the bars. LoxP sites (and relative orientations) are depicted as solid arrows.

FIG. 8A is a graph illustrating luciferase activity in 293T cells transfected with shortened AAV constructs according to some embodiments herein. The constructs contained five loxP sites. Luciferase activity for each construct was observed in the absence of CRE (i.e., pUC) and the presence or CRE.

FIG. 8B is a schematic diagram illustrating the position of the loxP sites for each of the constructs used in the experiment depicted in FIG. 8A. For each experiment (e.g. each pair of bars) in FIG. 8A, the corresponding construct schematic is shown in FIG. 8B to the right of the bars. Certain elements of the constructs are depicted, include a WPRE, WPRE (No X), WPRE (Short), SV40 PolyA sequence, and a synthetic PolyA sequence. LoxP sites (and relative orientations) are depicted as solid arrows.

FIG. 11A illustrates the results for vector 1594, FIG. 11B illustrates the results for vector 1784, FIG. 11C illustrates the results for vector 1799, FIG. 11D illustrates the results for vector 1605, FIG. 11E illustrates the results for vector 1785, FIG. 11F illustrates the results for vector 1800, FIG. 11G illustrates the results for vector 1782, FIG. 11H illustrates the results for vector 1797, FIG. 11I illustrates the results for vector 1806, FIG. 11J illustrates the results for vector 1490, FIG. 11K illustrates the results for vector 1783, FIG. 11L illustrates the results for vector 1798, and FIG. 11M illustrates the results for vector 1180.

FIG. 12A illustrates the results for vector 1594, FIG. 12B illustrates the results for vector 1784, FIG. 12C illustrates the results for vector 1799, FIG. 12D illustrates the results for vector 1605, FIG. 12E illustrates the results for vector 1785, FIG. 12F illustrates the results for vector 1800, FIG. 12G illustrates the results for vector 1782, FIG. 1211 illustrates the results for vector 1797, FIG. 12I illustrates the results for vector 1806, FIG. 12J illustrates the results for vector 1490, FIG. 12K illustrates the results for vector 1783, FIG. 12L illustrates the results for vector 1798, and FIG. 12M illustrates the results for vector 1180.

FIG. 14A illustrates a schematic vector encoding luciferase, but without Lox sites, and a Xenogen image of the detected luciferase expression for mice co-transfected with ZsGreen (no Cre; mice 1-2 from left) or Cre (mice 3-4 from left). FIG. 14B illustrates a schematic vector encoding luciferase with Lox sites and their relative orientations indicated by solid arrows, and a Xenogen image of the detected luciferase expression for mice co-transfected with ZsGreen (no Cre; mice 1-2 from left) or Cre (mice 3-4 from left).

FIG. 15A illustrates a schematic vector encoding luciferase, but without Lox sites, and a Xenogen image of the detected luciferase expression for mice co-transfected with ZsGreen (no Cre; mice 1-2 from left) or Cre (mice 3-4 from left). FIG. 15B illustrates a schematic vector encoding luciferase, with Lox sites and their relative orientations indicated by solid arrows, and a Xenogen image of the detected luciferase expression for mice co-transfected with ZsGreen (no Cre; mice 1-2 from left) or Cre (mice 3-4 from left).

FIG. 26 summarizes the results of the whole body Xenogen imaging shown in FIG. 19-23.

FIG. 27 summarizes the results of the liver Xenogen imaging shown in FIG. 19-23.

FIG. 28 summarizes the results of the leg Xenogen imaging shown in FIG. 19-23.

FIG. 30 is a graph illustrating expression levels of AC50 antibody (μg/mL) at various timepoints after infection with AAV vectors in the presence or absence of Cre, in accordance with some embodiments herein. Mice received intramuscular injection of either $2\times10^{10}$ GC of vector 1677 encoding the heavy chain and light chain of antibody AC50, but lacking loxP sites, or $2\times10^{10}$ GC of vector 1834 encoding the heavy chain and light chain of antibody AC50, and containing loxP sites in accordance with embodiments herein. 7 weeks later, the mice were injected intramuscularly with either $2.5\times10^{12}$ GC of vector 1787 (encoding GFP) or $2.5\times10^{12}$ GC of vector 1742 (encoding Cre). Antibody expression was measured by a sandwich ELISA, and although initial antibody expression levels were comparable, antibody expression was substantially decreased for the combination of vector 1834 (LoxP sites) and vector 1742 (Cre) in comparison to the other vectors.

DETAILED DESCRIPTION

Figures 3A, 3B, 3C:
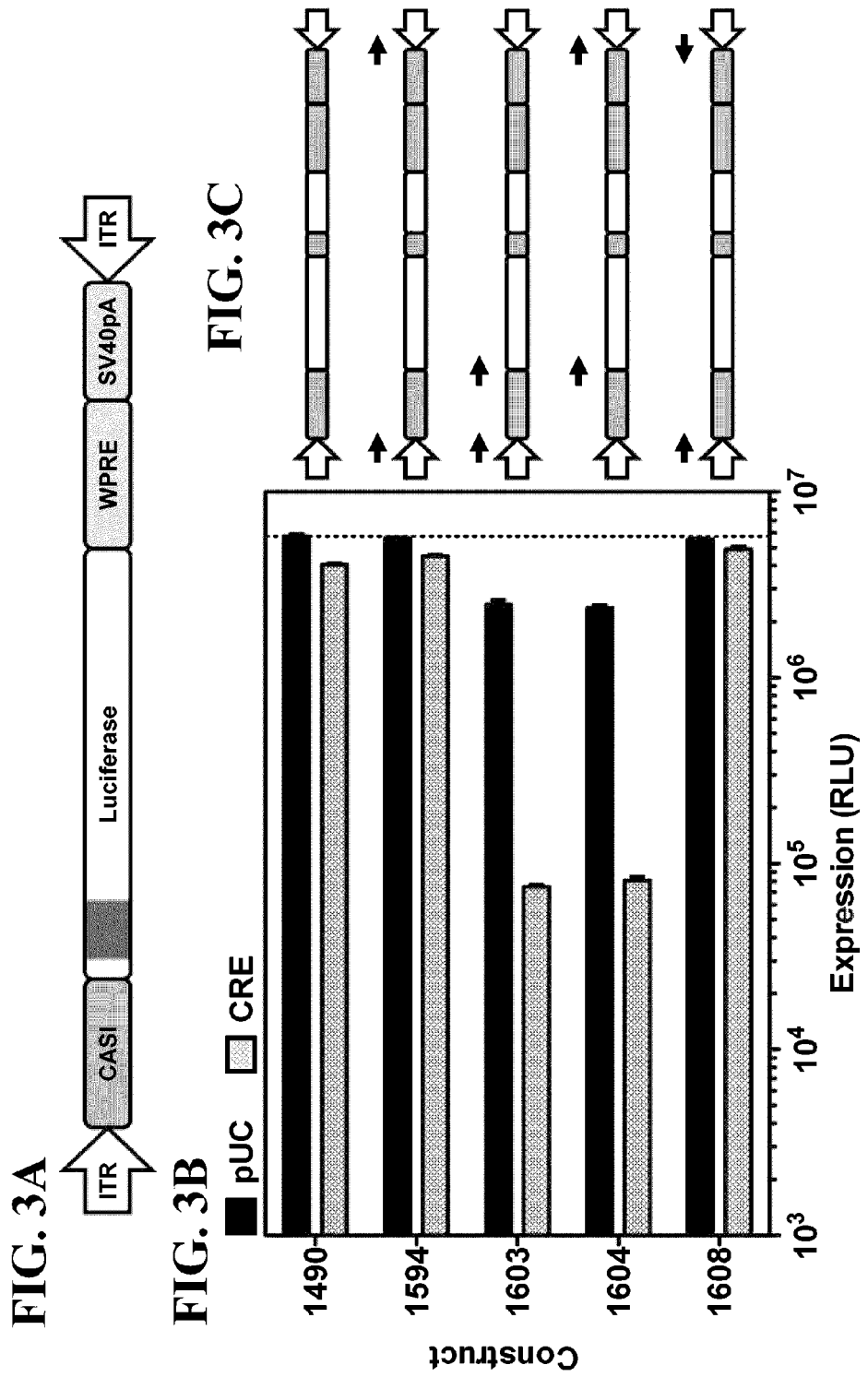
FIG. 3A is a schematic diagram of an adeno-associated vector for expressing a gene product of interest in accordance with some embodiments herein.
FIG. 3B is a graph illustrating luciferase activity in 293T cells transfected with AAV constructs according to some embodiments herein. The constructs were based on the vector of FIG. 3A, and contained two loxP sites. The luciferase activity for each construct was observed in the absence of CRE (i.e., pUC) and the presence or CRE.
FIG. 3C is a schematic diagram illustrating the position of the loxP sites for each of the constructs used in the experiment depicted in FIG. 3B. For each experiment (e.g. each pair of bars) in FIG. 3B, the corresponding construct schematic is shown in FIG. 3C to the right of the bars. LoxP sites (and relative orientations) are depicted as solid arrows.

According to some embodiments herein, reversible adeno-associated virus (AAV)-based gene expression systems are provided. The AAV gene expression systems can be useful for reversible gene expression in a mammal, for example for gene therapy applications. AAV is a non-integrating vector, and as such, does not modify the host cell genome. As AAV can stably exist in a host for a long time, it can be useful to turn-off gene expression from the AAV after a period of time. On the other hand, other types of vectors for gene expression, for example adenovirus, a typically short-lived, and thus would seldom benefit from additional mechanisms for turning-off gene expression. An AAV vector can encode a gene product of interest, and can contain a promoter region comprising a plurality of recombinase target sites, preferably positioned in the same orientation, although in some embodiments, different recombinase sites can be positioned in different orientations. One or more of the recombinase sites can be positioned between the promoter and the sequence encoding the gene product of interest. Upon insertion of the AAV vector into a mammal, the gene product of interest can be expressed. In some embodiments, at least some gene expression can be controllably turned-off using recombination. A recombinase can act upon two or more of the recombinase target sites of the inserted construct, inducing removal of sequences downstream of the promoter, and optionally at least a portion of the promoter. The removal of such sequences can reduce or eliminate expression of the gene product of interest. In some embodiments, the recombinase is encoded in a second AAV vector. In some embodiments, the recombinase is encoded in an adenoviral vector. In some embodiments, a cell-penetration-peptide-recombinase fusion polypeptide (for example Tat-Cre) is provided. Since AAV vectors do not integrate into the host genome, there is minimal danger of the recombinase inducing rearrangements in the host genome. In contrast, if multiple copies of an integrating vector (e.g. lentivirus) were to be integrated into a host genome, the recombinase could cause rearrangements.

As used herein, the term "vector" refers to a polynucleotide construct, typically a plasmid or a virus, used to transmit genetic material to a host cell. Vectors can be, for example, viruses, plasmids, cosmids, or phage. A vector as used herein can be composed of either DNA or RNA. In some embodiments, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

As used herein "upstream" refers to positions 5' of a location on a polynucleotide, and positions toward the N-terminus of a location on a polypeptide. As used herein "downstream" refers to positions 3' of a location on nucleotide and toward the C-terminus of a location on a polypeptide.

The term "construct," as used herein, refers to a recombinant nucleic acid that has been generated for the purpose of the expression of a specific nucleotide sequence(s), or that is to be used in the construction of other recombinant nucleotide sequences.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can modulate the efficiency of transcription, regardless of the distance or orientation of the enhancer relative to the start site of transcription.

As used herein, the term "antibody" is used in the broadest sense and specifically covers human, non-human (e.g., murine) and humanized monoclonal antibodies (including full-length monoclonal antibodies), polyclonal antibodies, multi-specific antibodies (e.g., bispecific antibodies), and antibody fragments so long as they exhibit the desired biological activity. Various antibodies can be expressed using the system and method disclosed herein. "Antibodies" and "immunoglobulins" are usually heterotetrameric glycoproteins, composed of two identical light (L) chains and two identical heavy (H) chains. Each light chain is linked to a heavy chain by a disulfide bond. The number of disulfide linkages varies among the heavy chains of different immunoglobulin isotypes. Each heavy chain comprises a variable domain ($V_H$) followed by a number of constant domains. Each light chain comprises a variable domain at one end ($V_L$) and a constant domain at its other end. The constant domain of the light chain is aligned with the first constant domain of the heavy chain, and the light-chain variable domain is aligned with the variable domain of the heavy chain. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

As used herein, the term "variant" refers to a polynucleotide (or polypeptide) having a sequence substantially similar to a reference polynucleotide (or polypeptide). In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans.

As used herein, the term "transfection" refers to the introduction of a nucleic acid into a host cell, such as by contacting the cell with a recombinant AAV vector as described herein.

AAV vectors

AAV vectors are a class of relatively compact vector that can be used to stably introduce a transgene into a host cell without integrating into the host genome. As such, AAV vectors can introduce a transgene without disruption host genomic sequences, and expression of a transgene from an AAV vector can persist for a long time, for example months or years. AAV vectors are described in detail in U.S. Pub. No. 2012/0232133, the entirety of which is incorporated by reference herein. AAV is a replication-deficient parvovirus, the single-stranded DNA genome of which is about 4.7 kb in length including 145 nucleotide inverted terminal repeat (ITRs). The ITRs can play a role in integration of the AAV DNA into the host cell genome. However, in the absence of the rep gene, integration by AAV vectors is negligible. It is contemplated that integration of AAV's comprising recombinase target sites into a host genome can create a risk of the recombinase inducing rearrangements of the host genome. For example if a first AAV integrates at a first genomic location, and a second AAV integrates at a second genomic location, and each AAV comprises a recombinase target site, the recombinase can induce recombination between the two AAVs, and thus rearrange portions of the host genome. Accordingly, preferably the AAV vectors in accordance with embodiments herein are configured not to integrate with the host genome. In some embodiments, the AAV vectors lack a functional rep gene. In some embodiments, the rep gene is deleted from the AAV vectors. In some embodiments, the ITRs of the AAVs are configured to minimize or eliminate integration.

Accounting for the ITR's (about 0.3 kb), AAV's can typically contain up to about 4.4 kb of nucleic acid sequence of interest. As such, AAV's are much more compact than adenovirus vectors, which can typically contain up to about 7.5 kb of nucleic acid sequence of interest. When AAV infects a host cell, the viral genome integrates into the host's chromosome resulting in latent infection of the cell. In a natural system, a helper virus (for example, adenovirus or herpesvirus) provides genes that allow for production of AAV vector in the infected cell. In the case of adenovirus, genes E1A, E1B, E2A, E4 and VA provide helper functions. Upon infection with a helper virus, the AAV provirus is rescued and amplified, and both AAV and adenovirus are produced. In the instances of recombinant AAV vectors having no Rep and/or Cap genes, the AAV can be non-integrating.

AAV vectors that comprise coding regions of one or more proteins of interest, for example proteins that are more than 500 amino acids in length, are provided. The AAV vector can include a 5' inverted terminal repeat (ITR) of AAV, a 3' AAV ITR, a promoter, and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the recombinant AAV vector includes a posttranscriptional regulatory element downstream of the restriction site and upstream of the 3' AAV ITR. In some embodiments, the AAV vectors disclosed herein can be used as AAV transfer vectors carrying a transgene encoding a protein of interest for producing recombinant AAV vectors that can express the protein of interest in a host cell.

Generation of the viral vector can be accomplished using any suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)).

The viral vector can incorporate sequences from the genome of any known organism. The sequences can be incorporated in their native form or can be modified in any way to obtain a desired activity. For example, the sequences can comprise insertions, deletions or substitutions.

The viral vectors described herein can include a prokaryotic replicon (that is, a DNA sequence having the ability to direct autonomous replication and maintenance of the recombinant DNA molecule extrachromosomally in a prokaryotic host cell), such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Additional Vectors

Additional exemplary vectors for use in eukaryotic cells that can be used in accordance with some embodiments herein, for example to deliver recombinase to the host cell, include, but are not limited to: pSVL and pKSV-10 available from Pharmacia; pBPV-1/pML2d (International Biotechnologies, Inc.); pCDNA and pTDT1 (ATCC, #31255); viral vectors based on vaccinia virus, poliovirus, adenovirus, herpes simplex virus, a lentivirus; vectors derived from retroviruses such as Rous Sarcoma Virus, Harvey Sarcoma Virus, avian leukosis virus, human immunodeficiency virus, myeloproliferative sarcoma virus, and mammary tumor virus); and the like. Additional examples of suitable eukaryotic vectors include bovine papilloma virus-based vectors, Epstein-Barr virus-based vectors, SV40, 2-micron circle, pcDNA3.1, pcDNA3.1/GS, pYES2/GS, pMT, pIND, pIND (Sp1), pVgRXR (Invitrogen), and the like, or their derivatives. In some embodiments, one of these vectors is used to deliver recombinase to the host cell. In some embodiments, one of these vectors is used to deliver a second gene product of interest to the host cell, for example a gene product in which reversible expression is not desired. In some embodiments, one of these vectors encodes a gene product of interest and comprises sequences for reversible expression of the gene product of interest as described herein.

Cell-Penetrating Peptides

Cell-penetrating peptides can be fused to a polypeptide of interest, and facilitate entry of the polypeptide of interest into a cell. According to some embodiments, polypeptides, for example recombinase polypeptides, are delivered to a cell through use of a cell penetration peptide. As discussed in more detail below, concurrently with, or following administration of an AAV vector for reversible expression of a gene product of interest to a host organism or cell, a recombinase polypeptide fused to a cell-penetration peptide can be administered to the host organism or cell, so that the recombinase enters the cell or cells of the host organism, and provides recombinase activity therein.

Various cell penetration peptides are known in the art, for example Hiv-1-Tat and derivatives thereof. HIV-1 Tat (MEPVDPRLEPWKHPGSQPKTACTNCYCKKCCFHC-QVCFITKALGISYGRKKRRQRR RAHQN-SQTHQASLSKQPTSQPRGDPTGPKE; SEQ ID NO: 5) has been shown to facilitate entry of a peptide comprising this sequence into a eukaryotic cell (see, e.g., Lundberg et al. (2002) A brief introduction to cell-penetrating peptides, J. Mol. Recognit. 16: 227-233, hereby incorporated by reference in its entirety). Various Tat derivatives fused to polypeptides of interest have been shown to mediate cell entry. For example, residues 47-57 of TAT (YGRKKRRQRRR; SEQ ID NO: 6) are sufficient to mediate cellular entry by a target polypeptide fused thereto. Additional exemplary cell-penetrating peptides are shown in Table 1, below. It is noted that several of the peptides identified in Table 1 include C-terminal amidation or cysteamide modification to facilitate cell-penetrating-peptide activity. In some embodiments, a cell penetrating peptide is fused to a C-terminus of a polypeptide of interest, for example a recombinase, so that the polypeptide of interest can be internalized by a cell. In some embodiments, the cell penetrating peptide is fused to an N-terminus of a polypeptide of interest. In some embodiments, the cell penetrating peptide is fused internally to a polypeptide of interest. In some embodiments, a cell-penetrating peptide comprising at least about 80% identity to a cell-penetrating polypeptide listed in Table 1, for example 80%, 81%, 82%, 83%, 84%, 85%, 86, 87%, 88%, 89%, 90%, 91%, 92%, 93%, 94%, 95%, 96%, 97%, 98%, or 99% identity is fused to a polypeptide of interest.

TABLE 1

| Exemplary Cell-Penetration Peptide | SEQ ID NO: | Sequence |
| --- | --- | --- |
| Penetratin | 7 | RQIKIWFQNRRMKWKK |
| Tat | 8 | YGRKKRRQRR |
| VT5 | 9 | DPKGDPKGVTVTVTVTVTGKGDPKPD-amide |
| MAP | 10 | KLALKLALKALKAALKLA-amide |
| Transportan | 11 | GWTLNSAGYLLGKINLKALAALAKKIL-amide |
| Transportan-10 | 12 | AGYLLGKINLKALAALAKKIL-amide |
| pVEC | 13 | LLIILRRRIRKQAHAHSK-amide |
| pISL | 14 | RVIRVWFQNKRCKDKK-amide |
| (R)$_7$ | 15 | RRRRRRR |
| Pep-1 | 16 | KETWWETWWTEWSQPKKKRKV (C-terminally modified with a cysteamide group) |
| Mouse PrP (1-28) | 17 | MANLGYWLLALFVTMWTDVGLCKKRPKP |

As discussed herein, cell-penetration peptides can be fused to a recombinase, and the recombinase can be administered to a host cell or host organism when reduction or elimination of gene expression from the AAV vector is desired.

Recombinases and Recombinase Target Sites

Recombination systems can mediate recombination between recombinase target sites, and depending on the orientation of the recombinase target sites, can either excise or flip sequences flanked by the recombinase target sites. According to some embodiments herein, recombinase target sites in the same orientation can flank portions of AAV vectors as described herein, so that upon addition of a recombinase, portions of the AAV vector can be removed, reducing or silencing expression of gene products encoded by these vectors. In some embodiments, an AAV vector encoding at least one gene product of interest and comprising recombinase target sites positioned as described herein is administered to a subject, so that the gene product or products of interest are expressed in the subject, and a recombinase is then administered to the subject (or recombinase activity is induced in the subject) to induce recombination in the AAV vector, so as to eliminate or reduce expression of the gene product or products of interest in the subject.

A variety of recombinases and corresponding recombinase target sites can be used in accordance with embodiments herein. "Recombinases," as used herein, refer to gene products and synthetic analogs thereof that catalyze recombination between a first and second polynucleotide. It is noted that recombinases typically can catalyze recombination between polynucleotide sequences in cis (i.e. on the same polynucleotide strand) or in trans (i.e. on different polynucleotide strands). "Recombinase target sites" refer to polynucleotide sequences on which recombinases specifically act to induce recombination. A particular recombinase may have specificity for a single nucleic acid sequence, or a plurality of nucleic acid sequences. Such a plurality of sequences can be described by a consensus sequence. In some embodiments, a recombinase polypeptide is provided. In some embodiments, a polynucleotide encoding a recombinase polypeptide (a "recombinase polynucleotide") is provided. Exemplary recombinases and recombinase target sites that can be used in accordance with embodiments herein include, but are not limited to, Cre-lox and FLP-FRT.

The Cre-lox system, derived from bacteriophage P1, is a well-characterized recombinase and recombinase target site system (see, e.g., Lakso et al., 1992, *Proc. Natl. Acad. Sci. USA* 89: 6232-6236; Orban et al., 1992, *Proc. Natl. Acad. Sci. USA* 89: 6861-6865, each of which is incorporated by reference herein in its entirety) that can be used in accordance with some embodiments herein. Cre recombinase catalyzes site-specific recombination, which can excise or invert an intervening target sequence or transgene located between lox sequences. Canonically, loxP sequences are targets for Cre recombinase. A loxP sequence comprises a 34 base pair polynucleotide sequence of SEQ ID NO: 18 (ATAACTTCGTATAGCATACATTATACGAAGTTAT). It is appreciated that variants loxP sequences, for example lox2272 and loxN can also be used as Cre recombinase target in accordance with embodiments herein (see Livet et al. (2007), Transgenic strategies for combinatorial expression of fluorescent proteins in the nervous system, Nature 450: 56-63). Lox2272 comprises the polynucleotide sequence of SEQ ID NO: 19 (ATAACTTCGTATAAAG-TATCCTATACGAAGTTAT). LoxN comprises the polynucleotide sequence of SEQ ID NO: 20 (ATAACTTCG-TATAGTATACCTTATACGAAGTTAT). Without being limited to any particular theory, Cre recombinase can work on any of the loxP or variant lox sites described herein. While Cre recombinase can induce recombination between a pair of identical lox sites (e.g. two loxP sites, or two lox2272 sites), Cre recombinase typically cannot induce recombination between a pair of non-identical lox sites (e.g. cannot induce recombination between a loxP and a lox2272 site, or a loxN and a lox2272 site). As such, according to some embodiments herein, for each lox sequence in the AAV vector, there is at least one additional identical lox sequence in the vector.

The orientation of lox sequences can determine whether the intervening transgene is excised or inverted when Cre recombinase is present (Abremski et al., 1984, *J. Biol. Chem.* 259:1509-1514). Cre can catalyze the excision of the transgene when the lox sequences are oriented as direct repeats (e.g. in the same orientation on the same strand) and catalyzes inversion of the transgene when lox sequences are oriented as inverted repeats (e.g. in opposite orientations on the strand. As such, in some embodiments, two or more lox sequences are oriented in the same direction on a polynucleotide strand. In some embodiments, 2, 3, 4, 5, 6, 7, 8, 9, 10, 11, 12, 13, 14, 15, 16, 17, 18, 19, or 20 lox sequences are oriented in the same direction on a polynucleotide strand. In some embodiments, all of the lox sequences on a strand are oriented in the same direction.

The FLP recombinase system, derived from of Saccharomyces cerevisiae (see, e.g., O'Gorman et al., 1991, *Science* 251: 1351-1355; PCT publication WO 92/15694, each of which is incorporated by reference herein in its entirety) can be used to generate in vivo site-specific genetic recombination, similar to the Cre-lox system. In some embodiments a FLP recombinase target (FRT) site comprises the sequence of SEQ ID NO: 21 (GAAGTTCCTATTCTCTA-GAAAGTATAGGAACTTC). A number of functional variant FRTs are known in the art, for example SEQ ID NO: 22 (GAAGTTCCTATTCCGAAGTTCCTATTCTCTA-GAAAGTATAGGAACTTC). Accordingly, in some embodiments, a variant FRT site is used. Without being limited by any particular theory, FLPase recombinase can work on any of the FRT or variant FRT sites described herein. While FLP recombinase can induce recombination between a pair of identical FLP sites, it typically cannot induce recombination between a pair of non-identical FRT sites. Similar to Cre, FLP recombinase can catalyze the excision of a sequence positioned between two FRT sites in the same orientation, and can catalyze the inversion of a sequence positioned between two FRT sites in opposite orientations. Accordingly, in some embodiments, at least two FRT sequences are oriented in the same direction on a polynucleotide strand. In some embodiments, 2, 3, 4, 5, 6, 7, 8, 9, 10, 11, 12, 13, 14, 15, 16, 17, 18, 19, or 20 FRT sequences are oriented in the same direction on a polynucleotide strand. In some embodiments, all of the FRT sequences on a strand are oriented in the same direction.

It is noted that while orienting a plurality identical recombinase target sites (e.g. loxP sites or FRT sites) in different directions could still result in excision of sequences, depending on which sites paired with each other, a combination of inversion and recombination events could occur, yielding different final sequences from AAV vector to AAV vector (e.g. if a vector included loxP1>loxP2> <loxP3<loxP4, with arrows indicating orientation, recombinase could excise the sequences between loxP1 and loxP2, and also the sequences between loxP3 and loxP4, but could also result in an inversion between loxP1 and loxP3, and a subsequent excision of sequences between loxP2 and loxP2, which would then be oriented in the same direction; the skilled artisan will appreciate that such an arrangement could also lead to a variety of other outcomes). Thus, preferably, all of the recombinase target sites that can recombine with each other (e.g. identical recombinase target sites) are oriented in the same direction.

While all of recombinase target sites that can recombine with each other are preferably oriented in the same orientation, in some embodiments, the AAV vector can comprise recombinase target sites in different orientations. In some embodiments, two or more of a first recombinase target site (e.g. a loxP site) are oriented in one direction flanking a first sequence, and two or more of a second, different, recombinase target site (e.g. an FRT site) are oriented in the other direction, flanking a second sequence. The addition of Cre can induce recombination between the loxP sites to excise the first sequence, while the addition of FLR can induce recombination between the FRT sites to excise the second sequence. Accordingly in some embodiments, recombinase target sites can be provided in different orientations, for example of two or more of a first recombinase target site are oriented in a first orientation, and two or more of a different, second recombinase target site are oriented in a second orientation, in which the first recombinase target sites are different from the second recombinase target sites, so that recombination events cannot be induced between the first and second sites.

Promoters and Associated Sequences

Various promoters can be operably linked with a nucleic acid comprising the coding region of the gene product of interest in the vectors to drive expression of the gene product of interest in accordance with embodiments herein. In some embodiments, the promoter can drive the expression of the protein of interest in a cell infected with a virus derived from the viral vector, such as a target cell. The promoter can be naturally-occurring or non-naturally occurring.

Examples of promoters, include, but are not limited to, viral promoters, plant promoters and mammalian promoters. Examples of viral promoters include, but are not limited to cytomegalovirus (CMV) immediate early promoter, CAG promoter (which is a combination of the CMV early enhancer element and chicken beta-actin promoter, described in Alexopoulou et al. BMC Cell Biology 9:2, (2008)), simian virus 40 (SV40) promoter, the 35S RNA and 19S RNA promoters of cauliflower mosaic virus (CaMV) described in Brisson et al., Nature 1984, 310:511-514, the coat protein promoter to tobacco mosaic virus (TMV), and any variants thereof. Examples of plant promoters include, but are not limited to, heat shock promoters, such as soybean hsp17.5-E or hsp17.3-B described in Gurley et al., Mol. Cell. Biol. 1986, 6:559-565, and any variants thereof. Examples of mammalian promoters include, but are not limited to, human elongation factor 1α-subunit (EF1-1α) promoter, human ubiquitin C (UCB) promoter, murine phosphoglycerate kinase-1 (PGK) promoter, and any variants thereof.

In some embodiments, the promoter is a synthetic CASI promoter. The synthetic CASI promoter contains a portion of the CMV enhancer, a portion of the chicken beta-actin promoter, and a portion of the UBC enhancer. In some embodiments, the UBC enhancer is positioned in a synthetic intron, for example flanked by an upstream splice donor and downstream splice acceptor. An exemplary portion of the chicken beta-actin promoter that can be used in CASI promoters in conjunction with embodiments herein includes SEQ ID NO: 23 (TGGTCGAGGTGAGCCCCACGTTCT-GCTTCACTCTCCCCATCTCCCCCCCCTCCCC ACC CCCAATTTTGTATTTATTTATTTTTTAATTATTTTGT-GCAGCGATGGGGGCGG GGGGGGGGGGGGGGCGCGCGCCAG-GCGGGGCGGGGCGGGGCGAGGGGCGGGGC GGGGCGAGGCGGAGAGGTGCGGCGGCAGC-CAATCAGAGCGGCGCGCTCCGAAA GTTTCCTTT-TATGGCGAGGCGGCGGCGGCGGCGGC-CCTATAAAAAGCGAAGCGC GCGGCGGGCGGGAGTCGCTGCGCGCTGCCTTCGC-CCCGTGCCCCGCTCCGCCGCC GCCTCGCGCCGC-CCGCCCCGGCTCTGACTGACCGCGTTACT), as well as polynucleotides with at least about 80% identity thereto, for example 80%, 81%, 82%, 83%, 84%, 85%, 86%, 87%, 88%, 89%, 90%, 91%, 92%, 93%, 94%, 95%, 96%, 97%, 98%, and 99%. An exemplary portion of the UBC enhancer that can be used in CASI promoters in conjunction with embodiments herein includes SEQ ID NO: 24 (GCCTC-CGCGCCGGGTTTTGGCGCCTCCCGCGGGCGCCCC CCTCCTCACGGCGAGC GCTGCCACGTCAGAC-GAAGGGCGCAGCGAGCGTCCTGATCCTTCCGC-CCGGACGC TCAGGACAGCGGCCCGCTGCT-CATAAGACTCGGCCTTAGAACCCCAGTATCAGCA GAAGGACATTTTAGGACGGGACTTGGGT-GACTCTAGGGCACTGGTTTTCTTTCCA GAGAGCG-GAACAGGCGAGGAAAAGTAGTCCCTTCTCGGC-GATTCTGCGGAGGGA TCTCCGTGGGGCGGTGAACGCCGATG), as well as polynucleotides with at least about 80% identity thereto, for example 80%, 81%, 82%, 83%, 84%, 85%, 86%, 87%, 88%, 89%, 90%, 91%, 92%, 93%, 94%, 95%, 96%, 97%, 98%, and 99%. In some embodiments, the CASI promoter is modified. In some embodiments, the CASI promoter comprises a first recombinase target site upstream of the splice donor and a second recombinase target site upstream of the splice acceptor. In some embodiments, the CASI promoter comprises a first recombinase target site upstream of the splice donor and a second recombinase target site downstream of the splice acceptor. In some embodiments, the CASI promoter comprises a first recombinase target site downstream of the splice donor and a second recombinase target site upstream of the splice acceptor. In some embodiments, the CASI promoter comprises a first recombinase target site downstream of the splice donor and a second recombinase target site downstream of the splice acceptor.

An exemplary modified CASI promoter that can be used in accordance with some embodiments herein is illustrated in FIG. 1B. Such a promoter can comprise, from 5' to 3', a CMV enhancer fragment, beta-actin promoter fragment, splice donor, UBC enhancer fragment, splice acceptor, in which a first pair of loxP sites flank the splice donor, and a second pair of loxP site flank the splice acceptor, and in which all four of the loxP sites are in the same orientation. Such promoter can comprise a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or more, sequence identity to SEQ ID NO: 25 (GGAGT-TCCGCGTTACATAACTTACGGTAAATGGCCCGCCT GGCTGACCGCCC AACGACCCCCGCCCATTGACGT-CAATAATGACGTATGTTCCCATAGTAACGCCAA TAGGGACTTTCCATTGACGTCAATGGGTGGAGT-ATTTACGGTAAACTGCCCACTT GGCAGTACAT-CAAGTGTATCATATGCCAAGTACGCCCCCTATT- GACGTCAATGACGGTAAATGGCCCGCCTGGCATTATGCCCAGTACATGACCTTATGGGACTTTCCTA CTTGGCAGTACATCTACGTATTAGTCATCGCTATTACCATGGTCGAGGTGAGCCC
CACGTTCTGCTTCACTCTCCCCATCTCCCCCCCCTCCCCACCCCCAATTTTGTATTT ATTTATTTTTTAATTATTTTGTGCAGC-GATGGGGGCGGGGGGGGGGGGGGGCGC
GCGCCAGGCGGGGCGGGGCGGGGC-GAGGGGCGGGGCGGGGCGAGGCGGAGAGG TGCGGCGGCAGCCAATCAGAGCGGCGCGCTC-CGAAAGTTTCCTTTTATGGCGAGG
CGGCGGCGGCGGCGGCCCTATAAAAAGC-GAAGCGCGCGGCGGGCGGGAGTCGCT GCGCGCT-GCCTTCGCCCCGTGCCCCGCTCCGCCGCCGC-CTCGCGCCGCCCGCCCC
GGCTCTGACTGACCGCGTTACTAAAACAGG-TAAGTCCATAACTTCGTATAGCATA CATTATAC-GAAGTTATGGCCTCCGCGCCGGGTTTTGGCGCCTC-CCGCGGGCGCCC
CCCTCCTCACGGCGAGCGCTGCCACGTCAGAC-GAAGGGCGCAGCGAGCGTCCTG ATCCTTCCGC-CCGGACGCTCAGGACAGCGGCCCGCTGCT-CATAAGACTCGGCCTT
AGAACCCCAGTATCAGCAGAAGGACATTTTAG-GACGGGACTTGGGTGACTCTAG GGCACTG-GTTTTCTTTCCAGAGAGCGGAACAGGCGAG-GAAAAGTAGTCCCTTCTC
GGCGATTCTGCGGAGGGATCTCCGTGGGGCGGT-GAACGCCGATGATATAACTTCG TATAGCATACAT-TATACGAAGTTATGCCTCTACTAACCATGTTCAT-GTTTTCTTTT
TTTTTCTACAGGTCCTGGGTGACGAACAG).

To increase expression from the promoter in vectors in accordance with embodiments herein, the promoter can comprise a transcriptional enhancer. In some embodiments, the transcriptional enhancer comprises a UBC enhancer. In some embodiments, the transcriptional enhancer is positioned in a synthetic intron. For example, the transcriptional enhancer can be positioned downstream of a splice acceptor, and upstream of a splice donor.

In some embodiments, the promoter is operably linked to a polynucleotide encoding one or more polypeptides of interest. In some embodiments, the promoter is operably linked with a polynucleotide encoding the heavy chain and/or the light chain of an antibody of interest, or a portion thereof (such as the heavy and light variable region of the antibody). In some embodiments, the promoter is operably linked to a polynucleotide encoding the heavy chain and the light chain of an antibody of interest to allow multicistronic expression of the heavy and light chain genes. In some embodiments, a cleavage site (for example a 2A sequence) or IRES element is positioned between the coding region of the heavy chain variable region and the coding region of the light chain variable region in the vector to facilitate equivalent expression of each subunit. Alternatively, polynucleotides encoding the heavy and light chains can be introduced separately into the target cell, each in an appropriate viral vector.

The size of the promoter can vary. Because of the limited packaging capacity of AAV, it is preferred to use a promoter that is small in size, but at the same time allows high level production of the protein(s) of interest in host cells. For example, in some embodiments the promoter is at most about 1.5 kb, at most about 1.4 kb, at most about 1.35 kb, at most about 1.3 kb, at most about 1.25 kb, at most about 1.2 kb, at most about 1.15 kb, at most about 1.1 kb, at most about 1.05 kb, at most about 1 kb, at most about 800 base pairs, at most about 600 base pairs, at most about 400 base pairs, at most about 200 base pairs, or at most about 100 base pairs.

Regulatory Elements

Vectors according to some embodiments herein, for example AAV vectors, can include various regulatory elements, such as a transcription initiation region and/or a transcriptional termination region. Examples of transcription termination region include, but are not limited to, polyadenylation signal sequences. Examples of polyadenylation signal sequences include, but are not limited to, Bovine growth hormone (BGH) poly(A), SV40 late poly(A), rabbit beta-globin (RBG) poly(A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence. In some embodiments, the transcriptional termination region comprises a SV40 late poly(A) sequence, for example the polynucleotide sequence of SEQ ID NO: 26 (TTCGAGCA-GACATGATAAGATACATTGATGAGTTTGGACAAAC-CACAACTAGAA TGCAGTGAAAAAAATGCTTTATTT-GTGAAATTTGTGATGCTATTGCTTTATTTGTA ACCATTATAAGCTGCAATAAACAAGT-TAACAACAACAATTGCATTCATTTTATGTT TCAGGT-TCAGGGGGAGATGTGGGAGGTTTTTTAAAGCAAG-TAAAACCTCTACAAA TGTGGTAAAATC) or a polynucleotides with at least about 80% identity thereto, for example 80%, 81%, 82%, 83%, 84%, 85%, 86%, 87%, 88%, 89%, 90%, 91%, 92%, 93%, 94%, 95%, 96%, 97%, 98%, and 99% identity. In some embodiments, the transcriptional termination region comprises a synthetic poly(A) sequence. In some embodiments, the transcriptional termination region comprises a synthetic poly(A) sequence, for example the polynucleotide sequence of SEQ ID NO: 43 (AATAAAATATCTTTATTTTCATTACATCTGTGTGT-TGGTTTTTTGTGTG), or a polynucleotides with at least about 80% identity thereto, for example 80%, 81%, 82%, 83%, 84%, 85%, 86%, 87%, 88%, 89%, 90%, 91%, 92%, 93%, 94%, 95%, 96%, 97%, 98%, and 99% identity.

Various posttranscriptional regulatory elements can be used in the viral vectors, for example to increase expression level of the protein of interest in a host cell. In some embodiments, the posttranscriptional regulatory element can be a viral posttranscriptional regulatory element. Non-limiting examples of viral posttranscriptional regulatory element include woodchuck hepatitis virus posttranscriptional regulatory element (WPRE), hepatitis B virus posttranscriptional regulatory element (HBVPRE), RNA transport element (RTE), and any variants thereof.

Figure 9A:
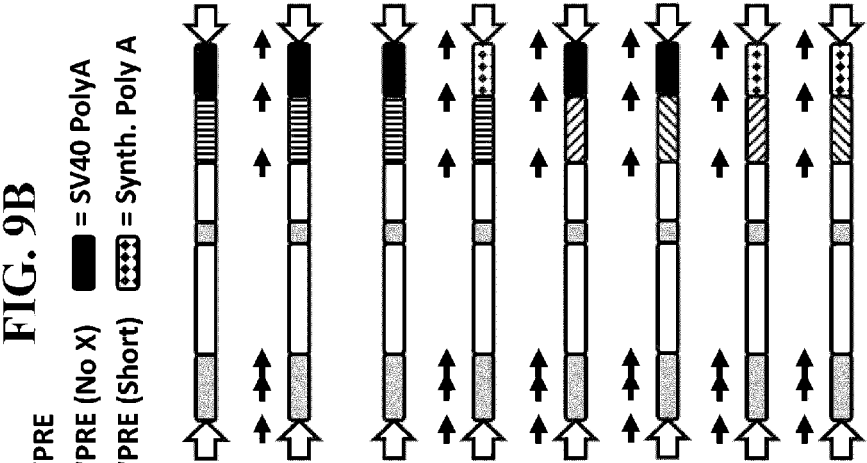
FIG. 9A is a graph illustrating luciferase activity in 293T cells transfected with shortened AAV constructs according to some embodiments herein. The constructs contained five loxP sites. Luciferase activity for each construct was observed in the absence of CRE (i.e., pUC) and the presence or CRE.
Figure 9B:
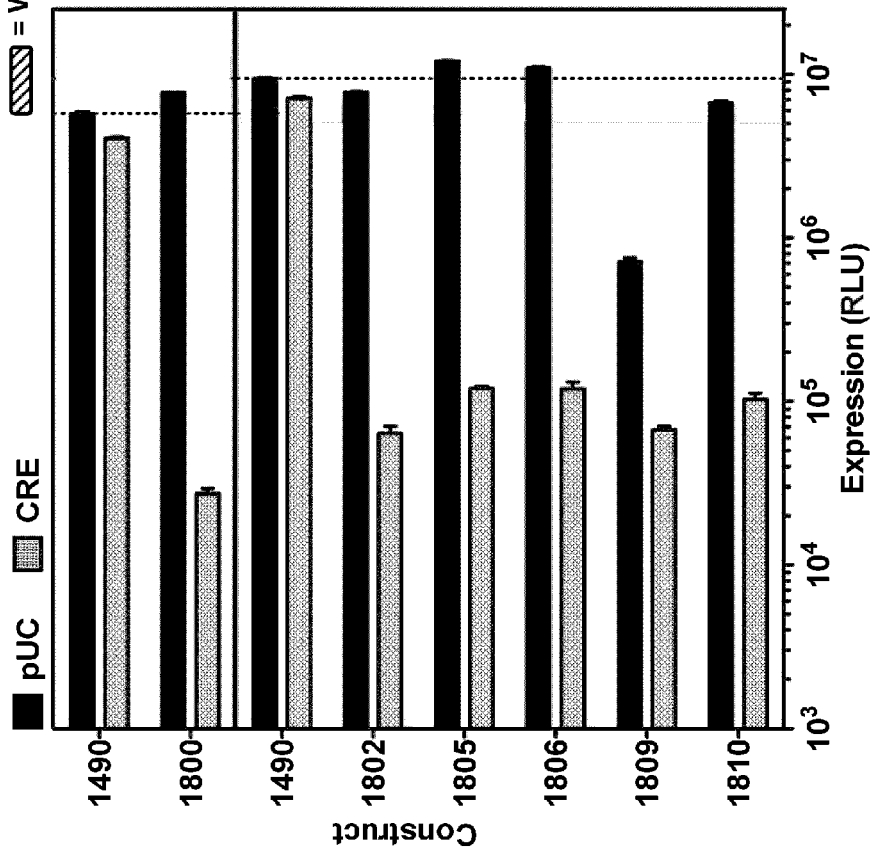
FIG. 9B is a schematic diagram illustrating the position of the loxP sites for each of the constructs used in the experiment depicted in FIG. 9A. For each experiment (e.g. each pair of bars) in FIG. 9A, the corresponding construct schematic is shown in FIG. 9B to the right of the bars. Certain elements of the constructs are depicted, include a WPRE, WPRE (No X), WPRE (Short), SV40 PolyA sequence, and a synthetic PolyA sequence. LoxP sites (and relative orientations) are depicted as solid arrows.

A variety of WPRE's can be used in accordance with embodiments herein. In some embodiments, the WPRE is "full-length" (see, e.g., FIGS. 8B and 9B), comprising the nucleic acid sequence of SEQ ID NO: 27 (TAATCAAC-CTCTGGATTACAAAATTTGTGAAAGATTGACTGGT-ATTCTTAACTAT GTTGCTCCTTTTACGCTATGTGGA-TACGCTGCTTTAATGCCTTTGTATCATGCTAT
TGCTTCCCGTATGGCTTTCATTTTCTCCTCCTTG-TATAAATCCTGGTTGCTGTCTCT TTATGAGGAGTT-GTGGCCCGTTGTCAGGCAACGTGGCGTGGTGTG-CACTGTGTT
GCTGACGCAACCCCCACTGGTTGGGGCATTGC-CACCACCTGTCAGCTCCTTTCCG
GGACTTTCGCTTTCCCCCTCCCTATTGCCACGGCG- GAACTCATCGCCGCCTGCCTT GCCCGCTGCTG-
GACAGGGGCTCGGCTGTTGGGCACTGACAATTC-
CGTGGTGTTGT
CGGGGAAATCATCGTCCTTTCCTTGGCTGCTCGC-
CTGTGTTGCCACCTGGATTCTG CGCGGGACGTCCT-
TCTGCTACGTCCCTTCGGCCCTCAATCCAGCGGAC-
CTTCCTTC
CCGCGGCCTGCTGCCGGCTCTGCGGCCTCTTC-
CGCGTCTTCGCCTTCGCCCTCAGA CGAGTCG-
GATCTCCCTTTGGGCCGCCTCCCCGCCT). It is contemplated herein that to increase cloning capacity of adeno-associated viral vectors, in some embodiments, a shorter WPRE is used. As shown in FIGS. 8-9, a variety of shorter WPREs can function comparably to the full-length WPRE to mediate gene expression. It has been observed that under some circumstances, an "X" polypeptide can be expressed from a portion of the WPRE sequence. To avoid expression of an "X" polypeptide, a portion of the WPRE can be removed, while still retaining posttranscriptional regulatory function (e.g. a "no X" WPRE). In some embodiments a "no X" WPRE is used, for example a WPRE of SEQ ID NO: 28 (TAATCAACCTCTGGATTACAAAATTTGTGAAAGAT-
TGACTGGTATTCTTAACTAT GTTGCTCCTTTTACGC-
TATGTGGATACGCTGCTTTAATGCCTTTGTATCAT-
GCTAT
TGCTTCCCGTATGGCTTTCATTTTCTCCTCCTTG-
TATAAATCCTGGTTGCTGTCTCT TTATGAGGAGTT-
GTGGCCCGTTGTCAGGCAACGTGGCGTGGTGTG-
CACTGTGTTT
GCTGACGCAACCCCCACTGGTTGGGGCATTGC-
CACCACCTGTCAGCTCCTTTCCG
GGACTTTCGCTTTCCCCCTCCCTATTGCCACGGCG-
GAACTCATCGCCGCCTGCCTT GCCCGCTGCTG-
GACAGGGGCTCGGCTGTTGGGCACTGACAATTC-
CGTGGTGTTGT CGGGGAAATCATCGTCCTTTCC)
(see, e.g., FIGS. 8B and 9B). In some embodiments, a "short WPRE" is used, for example SEQ ID NO: 29 (TAATCAAC-
CTCTGGATTACAAAATTTGTGAAAGATTGACTGGT-
ATTCTTAACTAT GTTGCTCCTTTTACGCTATGTGGA-
TACGCTGCTTTAATGCCTTTGTATCATGCTAT
TGCTTCCCGTATGGCTTTCATTTTCTCCTCCTTG-
TATAAATCCTGGTTGCTGTCTCT TTATGAGGAGTT-
GTGGCCCGTTGTCAGGCAACGTGGCGTGGTGTG-
CACTGTGTTT
GCTGACGCAACCCCCACTGGTTGGGGCATTGC-
CACCACCTGTCAGCTCCTTTCCG
GGACTTTCGCTTTCCCCCTCCCTATTGCCACGGCG-
GAACTCATCGCCGCCTGCCTT GCCCGCTGCTG-
GACAGGGGCTCGGCTGTTGGGCACTGACAATTC-
CGTGGTGTTGT
CGGGGAAATCATCGTCCTTTCCTTGGCTGCTCGC-
CTGTGTTGCCACCTGGATTCTG CGCGGGACGTCCT-
TCTGCTACGTCCCTTCGGCCCTCAATCCAGCGGAC-
CTTCCTTC CCG). In some embodiments, a variant of one of the listed WPREs is used. It is noted that the "no X" WPRE is about 69% identical (411/592 bases) to the "full-length" WPRE, while the "short" WPRE is about 85% identical (504/592 bases) to the "full-length" WPRE. Accordingly, in some embodiments, the adeno-associated vector comprises a WPRE with at least about 69% identity to the full-length WPRE, for example, at least about 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical, including ranges between any two of the listed values. In some embodiments, the WPRE is at least about 69% identical to the "short" WPRE or "no X" WPRE, for example, at least about 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical, including ranges between any two of the listed values.

The RTE can comprise a rev response element (RRE), for example, a lentiviral RRE. A non-limiting example is bovine immunodeficiency virus rev response element (RRE). In some embodiments, the RTE is a constitutive transport element (CTE). Examples of CTE include, but are not limited to Mason-Pfizer Monkey Virus CTE and Avian Leukemia Virus CTE.

In some embodiments, the AAV vector includes a gene for a selectable marker that is effective in a eukaryotic cell, such as a drug resistance selection marker. This selectable marker gene can encode a factor necessary for the survival or growth of transformed host cells grown in a selective culture medium. Host cells not transformed with the vector containing the selection gene will not survive in the culture medium. Typical selection genes encode proteins that confer resistance to antibiotics or other toxins, e.g., ampicillin, neomycin, methotrexate, kanamycin, gentamycin, Zeocin, or tetracycline, complement auxotrophic deficiencies, or supply critical nutrients withheld from the media.

The viral vectors disclosed herein can also include one or more A nucleotides immediately after an insertion site downstream of the promoter, where the insertion site allows the insertion of a polynucleotide encoding the protein(s) of interest. For example, one or more A nucleotides are located immediately after the TAA stop codon of the protein of interest after the insertion of the polynucleotide encoding the protein of interest into the vector. In some embodiments, one A nucleotide, two A nucleotides, three A nucleotides, or more are located immediately after the restriction site. In some embodiments, one A nucleotide, two A nucleotides, three A nucleotides, or more are located immediately after the TAA stop codon of the protein of interest.

In some embodiments, the viral vectors can include additional sequences that make the vectors suitable for replication and integration in eukaryotes. In other embodiments, the viral vectors disclosed herein can include a shuttle element that makes the vectors suitable for replication and integration in both prokaryotes and eukaryotes. In some embodiments, the viral vectors can include additional transcription and translation initiation sequences, such as promoters and enhancers; and additional transcription and translation terminators, such as polyadenylation signals.

In some embodiments, the viral vectors can include a regulatory sequence that allows, for example, the translation of multiple proteins from a single mRNA. Non-limiting examples of such regulatory sequences include internal ribosome entry site (IRES) and "cleavage polynucleotides" encoding cleavage sites such as 2A self-processing sequence. In some embodiments, the 2A sequence is a 2A peptide site from foot-and-mouth disease virus (F2A sequence). In some embodiments, the F2A sequence has a standard furin cleavage site. For example, the F2A sequence having a standard furin cleavage site can include a nucleotide sequence having at least about 90%, at least about 95%, at least about 96%, at least about 97%, at least about 98%, at least about 99%, or more, sequence identity to SEQ ID NO: 30 (CGGGCTAAGAGAGCACCGGTGAAACA-
GACTTTGAATTTTGACCTTCTCAAGTTG GCGGGA-
GACGTGGAGTCCAACCCAGGGCCC). In some embodiments, the F2A sequence has a modified furin cleavage site. For example, the F2A sequence having a modified furin cleavage site can include a nucleotide sequence having at least about 90%, at least about 95%, at least about 96%, at least about 97%, at least about 98%, at least about 99%, or more, sequence identity to SEQ ID NO: 31 (CGAAAAAGAAGATCAGGTTCGGGTGCGCCAG-TAAAGCAGACATTAAACTTTGAT TTGCTGAAACTT-GCAGGTGATGTAGAGTCAAATCCAGGTCCA).

The viral vectors can also, in some embodiments, have one or more restriction site(s) located near the promoter sequence to provide for the insertion of nucleic acid sequences encoding one or more proteins of interest and other protein(s).

Insertion Sites

In some embodiments, the AAV vector includes one or more insertion sites. An insertion site can be positioned for the insertion of a polynucleotide in a desired location on the AAV vector. In some embodiments, the insertion site is for inserting a polynucleotide encoding a desired gene product in a desired location. In some embodiments, the insertion site includes at least one cleavage polynucleotide (for example a 2A polynucleotide) positioned between a site for inserting a first polynucleotide encoding a gene product and a site for inserting a second polynucleotide encoding a gene product.

In some embodiments, an insertion site can be positioned in an AAV vector to facilitate insertion of a polynucleotide encoding a gene product of interest that is operatively linked to the promoter of the AAV vector. The insertion site can be positioned 3' to the promoter, for example about 10 bp, 20, 30, 40, 50, 100, 150, 200, 250, 300, 400, 500, 600, 700, 800, 900, 1000, 1100, 1200, 1500, or 2000 bp 3' to the promoter.

In some embodiments, the insertion site is configured for the insertion of a first polynucleotide encoding a first gene product of interest and a second polynucleotide encoding a second gene product of interest. The insertion site can comprise a cleavage polynucleotide positioned 3' of a site in which the first polynucleotide can be inserted, and can be configured to be in-frame with the coding sequence of the first polynucleotide. The cleavage polynucleotide can be positioned 5' of a site in which the second polynucleotide can be inserted, and can be configured to be in-frame with the coding sequence of the second polynucleotide. In some embodiments, the cleavage polynucleotide encodes a 2A sequence or 2A variant as described herein.

In some embodiments, the insertion site comprises one or more restriction endonuclease sites. In some embodiments, the insertion site comprises a multiple cloning site (MCS). In some embodiments, the insertion site comprises a GATE-WAY destination site.

Cleavage Sites

As used herein "cleavage site" refers to a sequence that mediates the separation of a first polypeptide that would otherwise be in cis to a second polypeptide. Accordingly, for simplicity, "cleavage," "cleavage site," and the like as used herein refer to the separation of any two polypeptides that are encoded by a single polynucleotide in cis. Thus, "cleavage" and "cleavage site," can, but do not necessarily refer to proteolytic sites and events, and can also refer to other mechanisms for mediating the separation of polypeptides, for example ribosomal skipping. As used herein "cleavage polynucleotide" refers to a polynucleotide encoding a cleavage site. In some embodiments, a cleavage site mediates the separation via an intra-ribosomal, translational termination-and-restart event during the synthesis of the nascent polypeptide chains so that a peptide bond is not formed between an upstream amino acid residue and a downstream amino acid residue. For example, such a cleavage site can include a 2A polypeptide as described herein. Exemplary cleavage sites are listed in Table 2. For example, such a cleavage site can comprise a translation termination sequence (e.g. a stop codon) upstream of an internal ribosome entry site. In some embodiments, a cleavage site includes a protease target site. For example, such a protease target site can comprise a furin cleavage site (Arg-X-X-Arg, preferably Arg-X-Lys/Arg-Arg; SEQ ID NO: 32). As used herein, "cleavage polynucleotide" refers to a polynucleotide that encodes a cleavage site.

As used herein, 2A sequences or elements refer to small peptides introduced as a linker between two proteins, allowing autonomous intraribosomal self-processing of polyproteins (See e.g., de Felipe. Genetic Vaccines and Ther. 2:13 (2004); deFelipe et al. Traffic 5:616-626 (2004)). These short peptides allow co-expression of multiple proteins from a single vector. Many 2A elements are known in the art. Examples of 2A sequences that can be used in the methods and system disclosed herein, without limitation, include 2A sequences from the foot-and-mouth disease virus (F2A), equine rhinitis A virus (E2A), *Thosea asigna* virus (T2A), and porcine teschovirus-1 (P2A) as described in U.S. Patent Publication No. 2007/0116690. In some embodiments, a cleavage site comprises a 2A polypeptide. In some embodiments, the 2A polypeptide comprises a wild-type 2A polypeptide from foot-and-mouth disease virus ("F2A"; QLL-NFDLLKLAGDVESNPGP; SEQ ID NO: 33). In some embodiments, the 2A polypeptide is selected from Table 1. In some embodiments, the 2A polypeptide is a variant of a 2A polypeptide from Table 1. Variants can include polypeptide sequences having at least about 80%, at least about 85%, at least about 90%, at least about 95%, at least about 97%, at least about 99%, or more, sequence identity to a 2A polypeptide disclosed herein. Variants can include a deletion of at least one N-terminal amino acid from the 2A polypeptide of SEQ ID NO: 33, for example a deletion of 1, 2, 3, 4, 5, 6, 7, 8, 9, or 10 amino acids, including ranges between any two of the listed values. Variants can include a deletion of at least one C-terminal amino acid from the 2A polypeptide of SEQ ID NO: 33, for example a deletion of 1, 2, 3, 4, 5, 6, 7, 8, 9, or 10 amino acids.

Depending on the desired stoichiometry between two gene products encoded in a single transcript, a cleavage site of desired activity can be selected. In some embodiments, a polynucleotide encoding the 2A polypeptide is selected based on its relative activity. In some embodiments, F2A (wt)(QLLNFDLLKLAGDVESNPGP; SEQ ID NO: 34); F2A(-2) (LNFDLLKLAGDVESNPGP; SEQ ID NO: 35), and F2A(-1) (LLNFDLLKLAGDVESNPGP; SEQ ID NO: 36) are relatively high activity 2A polypeptides. In some embodiments, F2A(-7) (LKLAGDVESNPGP; SEQ ID NO: 37), F2A(19) (QLLNFDLLKLAGDVESNPAP; SEQ ID NO: 38), I2A(0) (TRAEIEDELIRRGIESNPGP; SEQ ID NO: 39), I2A(1) (TRAEIEDELIRRGIESNPGP; SEQ ID NO: 40), I2A(2) (TRAEIEDELIRRGIESNPGP; SEQ ID NO: 41), and I2A(3) (TRAEIEDELIRRGIESNPAP; SEQ ID NO: 42) are relatively low activity 2A polypeptides.

Gene Products of Interest

As used herein "gene product of interest," also referred to as "desired gene product" refers to a gene product, for example a polypeptide or polynucleotide (such as a ribosomal RNA, ribozyme, dsRNA, antisense-polynucleotide, siRNA, or the like) that can be inducibly expressed in a host cell or host organism.

It can be useful to express an antibody directly in a host organism. For example, vectored immunoprophylaxis can be an effective strategy to prevent HIV infection in humanized mice, and involves continuous production of antibody proteins at protective doses to function. Regulation systems that require the addition of exogenous drugs to maintain gene expression are not amenable to prophylaxis strategies due to difficulty of achieving patient compliance for drugs that could prevent infection such as HAART. As such, in some embodiments, the gene product of interest comprises an antibody.

It can be useful to replace or supplement a defective gene product through gene therapy. However, in some instances, it can be useful to subsequently silence expression of a gene product in gene therapy. For example in the context of clinical trials for a gene therapy product, it can be useful to have the option to reduce or eliminate transgene expression. For example, if a transgene construct in clinical trials may produce undesired side effects, or if an improved transgene construct is developed subsequent to the clinical trials, it can be useful to reduce or eliminate expression from the earlier transgene, so as to minimize or end the undesired side effects, or to deactivate the earlier transgene if favor of a later-generation transgene.

AAV Vectors

Various vectors can be used to express gene products of interest in mammals or mammalian cells as described herein, for example, for gene therapy. In some embodiments, the vector comprises an AAV vector. A variety of AAV vectors can be used in inducible expression systems in accordance with embodiments herein. In some embodiments, an AAV vector comprises a first ITR, and a promoter positioned downstream (3') of the first ITR. The vector can comprise a first recombinase target site downstream (3') of the first ITR, and upstream (5') of the 3' end of promoter. The vector can comprise an insertion site downstream (3') of the promoter such that the promoter is operably linked to any polypeptide (for example, a polypeptide encoding a gene product of interest) that is inserted in the insertion site. The vector can comprise a second recombinase target site positioned downstream (3') of the 5' end of the promoter and upstream (5') of the insertion site. The vector can comprise a third recombinase target site positioned downstream (3') of the insertion site and upstream (5') of a second ITR. All three of the recombinase sites can be oriented in the same direction. The inducible expression system can also comprise a source of recombinase that can act on the recombination target sites.

In some embodiments, the vector also include a WPRE positioned downstream (3') of the insertion site and upstream (5') of a second ITR. The vector can also include a fourth recombinase target site positioned downstream (3') of the insertion site and upstream (5') of a 3' end of the WPRE. The vector can also include a fifth recombinase target site positioned downstream (3') of a 5' end of the WPRE. The vector can also include a sixth recombinase target site positioned downstream (3') of the WPRE and upstream (5') of the second ITR. All six recombinase target sites can all be oriented in the same direction.

In some embodiments, the AAV vector comprises at least three recombinase target sites, more preferably, four recombinase target sites, more preferably five recombinase target sites, more preferably six recombinase target sites. In some embodiments, the AAV vector comprises at least three recombinase target sites, for example 3, 4, 5, 6, 7, 8, 9, 10, 11, 12, 13, 14, 15, 16, 17, 18, 19, or 20 recombinase target sites, including ranges between any two of the listed values.

In some embodiments, the recombinase comprises Cre, and the recombinase target sites comprise lox sites. In some embodiments, the recombinase comprises FLPase, and the recombinase target sites comprise FRT sites. In some embodiments, for each recombinase target site in the AAV vector, there is at least one other identical recombinase target site in the same orientation also in the vector, preferably at least two other identical sites in the same orientation, more preferably at least four other identical sites in the same orientation, more preferably at least five other identical sites in the same orientation.

In some embodiments, the WPRE is a full-length WPRE as described herein, or a variant thereof. In some embodiments, the WPRE is a full-length WPRE as described herein, or a variant thereof, for example SEQ ID NO: 27. In some embodiments, the WPRE is a "short" WPRE or a variant thereof, for example SEQ ID NO: 28. In some embodiments, the WPRE is a "no X" WPRE or a variant thereof, for example SEQ ID NO: 29.

In some embodiments, the AAV virus vector comprises a polyadenylation site. The polyadenylation site can be positioned downstream (3') of the WPRE and upstream (5') of the second ITR. In some embodiments, the polyadenylation site comprises a SV40 polyadenylation site as described herein. In some embodiments, the polyadenylation site comprises a synthetic polyadenylation site as described herein.

In some embodiments, the insertion site is configured for the insertion of polynucleotide encoding a gene product of interest. In some embodiments, the insertion site is configured for the insertion of two or more polynucleotides each encoding gene products of interest, and separated by a cleavage polynucleotide. In some embodiments, the insertion site is configured for insertion of a single polynucleotide comprising the two or more polynucleotides encoding gene products of interest (optionally with a cleavage polynucleotide or IRES positioned therebetween). In some embodiments, the insertion site configured for insertion of a first polynucleotide encoding a first gene product of interest and a second polynucleotide encoding a second gene product of interest. Such an insertion site can optionally comprise a cleavage polynucleotide or IRES positioned therebetween. The cleavage site can be configured to encode a cleavage site in-frame with the sequences encoding the gene products of interest. As such, the AAV vector can be configured to simultaneously express two or more gene products of interest. In some embodiments, the gene products of interest comprise the light chain and the heavy chain of an immunoglobulin, for example an antibody. In some embodiments, the gene products of interest comprise multimeric subunits of a gene product to be expressed in gene therapy, for example a multimeric extracellular receptor.

In some embodiments, the AAV vectors comprises vector 1806 (SEQ ID NO: 1) or a variant thereof. It is noted that vector 1806 comprises a "no X" WPRE, and an SV40 polyadenylation sequence. It is noted that vector 1806 comprises polypeptides encoding a heavy chain and light chain of antibody AC50, separated, in-frame by a 2A polypeptide. It is contemplated that in some embodiments, other polynucleotides encoding gene products of interest can readily be inserted into the backbone of vector 1806 or a variant thereof. As used herein, the "backbone" of vector 1806 refers to the sequence of vector 1806, excluding the polynucleotides encoding the light and heavy chains. In some embodiments, the backbone of vector 1806, or a variant having at least about 90% identity to the backbone vector 1806, for example about 90%, 91%, 92%, 93%, 94%, 95%, 96%, 97%, 98%, 99%, 99.5%, or 99.9% identity to the backbone of vector 1806 is provided. In some embodiments, at least one polypeptide encoding a gene product of interest is inserted therein. In some embodiments, at least two polypeptides, each encoding a gene product are inserted therein, and separated, in-frame by a cleavage polypeptide, for example a polypeptide encoding 2A. In some embodiments, the two polypeptides encode different gene products. In some embodiments, the two polypeptides each encode the same gene product.

In some embodiments, the AAV vector comprises a promoter, for example a CASI promoter or modified CASI promoter as described herein. The AAV vector can further comprise a first recombinase target site positioned 5' to a 3' end of the promoter, for example positioned inside the promoter, or downstream of the promoter. The AAV vector can further comprise a second recombinase target site positioned 3' to a 5' end of the promoter. The second recombinase target site can be positioned 3' to the first recombinase target site, and, for example, can be positioned inside the promoter or downstream of the promoter. In some embodiments, the first and second recombinase sites flank a synthetic intron of the promoter. In some embodiments, one or both of the first and second recombinase sites are positioned within a synthetic intron of the promoter. The AAV vector can further comprise an insertion site positioned 3' to the promoter and 3' to the second recombinase target site, such that the promoter would be operably linked to at least an inserted polynucleotide. The AAV vector can further comprise a third recombinase target site positioned 3' to the insertion site. In some embodiments, the AAV vector includes flanking ITRs, with a first ITR positioned 5' to the first recombinase target site and promoter, and a second ITR positioned 3' to the third recombinase site. In some embodiments, the first, second, and third recombinase sites are in the same orientation. In some embodiments, the first, second, and third recombinase target sites comprise lox sites, for example loxP sites, loxN sites, or lox2272 sites as described herein. In some embodiments, the first, second, and third recombinase target sites comprise FRT sites. In some embodiments, the AAV further comprises a WPRE positioned 3' to the insertion site, and 5' to the second ITR. The third recombinase target site can be positioned between the WPRE and the second ITR (e.g. 3' of the WPRE and 5' of the ITR). In some embodiments, the WPRE is a full-length WPRE as described herein. In some embodiments, the WPRE is a short WPRE as described herein. In some embodiments, the WPRE is a "no X" WPRE as described herein. The AAV vector can further comprise a fourth recombinase target site positioned 3' to the insertion site and 5' to a 3' end of the WPRE, for example within the WPRE or downstream of the WPRE. The AAV vector can further comprise a polyadenylation site, for example an SV40 polyadenylation site or synthetic polyadenylation site as described herein. The AAV can further comprise a fifth recombinase target site positioned 3' to the fourth recombinase target site and downstream of the WPRE (i.e. 3' to the WPRE). The AAV can further comprise a sixth recombinase target site positioned 3' to the first recombinase target site and 5' to the second recombinase target site. The fourth, fifth, and sixth recombinase target sites can be oriented in the same direction. In some embodiments, the first, second, third, fourth, fifth, and sixth recombinase target sites are oriented in the same direction. In some embodiments, the first, second, and third recombinase target sites are oriented in one direction, and the fourth, fifth, and sixth recombinase target sites are oriented in the other direction, for example if the first, second, and third recombinase target sites are identical (e.g. loxP sites) and the fourth, fifth, and sixth recombinase target sites are identical but different from the first, second, and third recombinase target sited (e.g. the fourth, fifth, and sixth sites are loxP sites). In some embodiments, at least two of the first, second, and third recombinase target sites are positioned flanking and/or within a synthetic intron of the promoter as described herein. In some embodiments, the promoter of the vector comprises a synthetic intron comprising a transcriptional enhancer as described herein. In some embodiments, each of the first and second recombinase target sites flank the synthetic intron. In some embodiments, one of the first and second recombinase target sites is positioned adjacent to the synthetic intron (e.g. upstream of the splice donor or downstream of the splice acceptor), and the other is positioned within the synthetic intron (e.g. between the splice donor and splice acceptor). In some embodiments, both of the first and second recombinase target sites are positioned within the synthetic intron.

In some embodiments, the AAV vector comprises a first ITR, a first recombinase target site positioned 3' to the first ITR and 5' of the 3' end of a promoter, a second recombinase target site within the promoter and 3' of the first recombinase target site, an insertion site 3' to the promoter, a third recombinase target site positioned 3' to the insertion site, a WPRE positioned 3' to the third recombinase target site, a fourth recombinase target site positioned 3' to the WPRE, a polyadenylation sequence positioned 3' to the fourth recombinase target site, a fifth recombinase target site positioned 3' to the polyadenylation sequence, and a second ITR positioned 3' to the fifth recombinase target site. In some embodiments, the promoter comprises a CASI promoter as described herein. In some embodiments, the promoter comprises a modified CASI promoter as described herein, in which the first recombinase target site and second recombinase target site are positioned either flanking a synthetic intron, within the synthetic intron, or such that one recombinase target site is positioned 5' to the splice donor or 3' to the splice acceptor of the synthetic intron and the other recombinase target site is positioned between the splice donor and splice acceptor. In some embodiments, the first, second, third, fourth, and fifth recombinase target sites are all in the same orientation. In some embodiments, the WPRE comprises one of a full-length WPRE, "short" WPRE, or "no X" WPRE as described herein. In some embodiments, the polyadenylation sequence comprises one of an SV40 polyadenylation sequence or synthetic polyadenylation sequence. Exemplary AAV vectors according to some of these embodiments are illustrated schematically in FIG. 8B. In some embodiments, the recombinase target sites comprise lox sites as described herein. In some embodiments, the recombinase target sites comprise FRT sites as described herein.

In some embodiments, the AAV vector comprises a first ITR, a first recombinase target site positioned 3' to the first ITR and 5' of the 3' end of a promoter, a second recombinase target site within the promoter and 3' of the first recombinase target site, a third recombinase target site positioned within the promoter and 3' of the second recombinase target site. The AAV vector can comprise an insertion site 3' to the promoter, a fourth recombinase target site positioned 3' to the insertion site, a WPRE positioned 3' to the fourth recombinase target site, a fifth recombinase target site positioned 3' to the WPRE, a polyadenylation sequence positioned 3' to the fifth recombinase target site, a sixth recombinase target site positioned 3' to the polyadenylation sequence, and a second ITR positioned 3' to the sixth recombinase target site. In some embodiments, the promoter comprises a CASI promoter as described herein. In some embodiments, the promoter comprises a modified CASI promoter as described herein, in which the second recombinase target site and third recombinase target site are positioned either flanking a synthetic intron, within the synthetic intron, or such that one recombinase target site is 5' to the splice donor or 3' to the splice acceptor of the synthetic intron and the other recombinase target site is between the splice donor and splice acceptor. In some embodiments, the first, second, third, fourth, fifth, and sixth recombinase target sites are all in the same orientation. In some embodiments, the WPRE comprises one of a full-length WPRE, "short" WPRE, or "no X" WPRE as described herein. In some embodiments, the polyadenylation sequence comprises one of an SV40 polyadenylation sequence or synthetic polyadenylation sequence. Exemplary AAV vectors according to some of these embodiments are illustrated schematically in FIG. 9B. In some embodiments, the recombinase target sites comprise lox sites as described herein. In some embodiments, the recombinase target sites comprise FRT sites as described herein.

In some embodiments, the AAV vector comprises a first ITR, a first recombinase target site positioned 3' to the first ITR and 5' of the 3' end of a promoter, a second recombinase target site within the promoter and 3' of the first recombinase target site, a first polynucleotide encoding a gene product of interest 3' to the promoter, and a third recombinase target site positioned 3' to the first polynucleotide. Optionally, the AAV vector can further comprise a second polynucleotide encoding a second gene product of interest positioned 3' to the first polynucleotide and 5' to the third recombinase target site. In some embodiments, the coding sequences of the first polynucleotide and second polynucleotide are in-frame with each other, and a cleavage polynucleotide is positioned 3' of (and in-frame with) the first polynucleotide and 5' to (and in-frame with) the second polynucleotide. Exemplary cleavage polynucleotides can include polynucleotides encoding 2A or 2A variant as described herein, or a furin site as described herein. In some embodiments, an IRES is positioned between the first and second polynucleotide. In some embodiments, the first polynucleotide encodes one of the heavy chain or light chain of an antibody, and the second polynucleotide encode the other of the heavy chain or light chain of an antibody. The AAV vector can further include a WPRE positioned 3' to the third recombinase target site, a fourth recombinase target site positioned 3' to the WPRE, a polyadenylation sequence positioned 3' to the fourth recombinase target site, a fifth recombinase target site positioned 3' to the polyadenylation sequence, and a second ITR positioned 3' to the fifth recombinase target site. In some embodiments, the promoter comprises a CASI promoter as described herein. In some embodiments, the promoter comprises a modified CASI promoter as described herein, in which the first recombinase target site and second recombinase target site are positioned either flanking a synthetic intron, within the synthetic intron, or with one recombinase target site 5' to the splice donor or 3' to the splice acceptor of the synthetic intron and the other recombinase target site between the splice donor and splice acceptor. In some embodiments, the first, second, third, fourth, and fifth recombinase target sites are all in the same orientation. In some embodiments, the WPRE comprises one of a full-length WPRE, "short" WPRE, or "no X" WPRE as described herein. In some embodiments, the polyadenylation sequence comprises one of an SV40 polyadenylation sequence or synthetic polyadenylation sequence. In some embodiments, the recombinase target sites comprise lox sites as described herein. In some embodiments, the recombinase target sites comprise FRT sites as described herein.

In some embodiments, the AAV vector comprises a first ITR, a first recombinase target site positioned 3' to the first ITR and 5' of the 3' end of a promoter, a second recombinase target site within the promoter and 3' of the first recombinase target site, a third recombinase target site positioned within the promoter and 3' of the second recombinase target site. The AAV vector can comprise a first polynucleotide encoding a gene product of interest 3' to the promoter, and a fourth recombinase target site positioned 3' to the first polynucleotide. Optionally, the AAV vector can further comprise a second polynucleotide encoding a second gene product of interest positioned 3' to the first polynucleotide and 5' to the fourth recombinase target site. In some embodiments, the coding sequences of the first polynucleotide and second polynucleotide are in-frame with each other, and a cleavage polynucleotide is positioned 3' of (and in-frame with) the first polynucleotide and 5' to (and in-frame with) the second polynucleotide. Exemplary cleavage polynucleotides can include polynucleotides encoding 2A or 2A variant as described herein, or a furin site as described herein. In some embodiments, an IRES is positioned between the first and second polynucleotide. In some embodiments, the first polynucleotide encodes one of the heavy chain or light chain of an antibody, and the second polynucleotide encode the other of the heavy chain or light chain of an antibody. The AAV vector can include a WPRE positioned 3' to the fourth recombinase target site, a fifth recombinase target site positioned 3' to the WPRE, a polyadenylation sequence positioned 3' to the fifth recombinase target site, a sixth recombinase target site positioned 3' to the polyadenylation sequence, and a second ITR positioned 3' to the sixth recombinase target site. In some embodiments, the promoter comprises a CASI promoter as described herein. In some embodiments, the promoter comprises a modified CASI promoter as described herein, in which the second recombinase target site and third recombinase target site are positioned either flanking a synthetic intron, within the synthetic intron, or such that one recombinase target site is 5' to the splice donor or 3' to the splice acceptor of the synthetic intron and the other recombinase target site is between the splice donor and splice acceptor. In some embodiments, the first, second, third, fourth, fifth, and sixth recombinase target sites are all in the same orientation. In some embodiments, the WPRE comprises one of a full-length WPRE, "short" WPRE, or "no X" WPRE as described herein. In some embodiments, the polyadenylation sequence comprises one of an SV40 polyadenylation sequence or synthetic polyadenylation sequence. Exemplary AAV vectors according to some of these embodiments are illustrated schematically in FIG. 1A. In some embodiments, the recombinase target sites comprise lox sites as described herein. In some embodiments, the recombinase target sites comprise FRT sites as described herein.

Reversible Expression Systems

According to some embodiments, reversible expression systems are provided. The expression systems can include a first AAV vector as described herein. In some embodiments, the first AAV vector comprises a polynucleotide encoding a desired gene product. In some embodiments, the first AAV vector comprises at least one insertion site for a polynucleotide encoding a desired gene product. The expression systems can include a source of recombinase as described herein. In some embodiments, the recombinase is encoded on a second AAV vector. In some embodiments, the recombinase is encoded on a second vector that is not an AAV vector, for example an adenoviral vector. The AAV or non-AAV vector encoding the recombinase can comprise promoter operably linked to a recombinase polypeptide. In some embodiments, the recombinase polypeptide is fused to a cell-penetration peptide, for example Tat or a variant thereof, to facilitate entry of the cell by the recombinase polypeptide.

In some embodiments, the source of the recombinase comprises a second vector encoding the recombinase. In some embodiments, an AAV vector encodes the recombinase. In some embodiments, an adenoviral vector encodes the recombinase. In some embodiments, a fusion polypeptide of a cell-penetration peptide and recombinase (for example Tat-Cre or Tat-FLPase) is provided. In some embodiments, a polynucleotide encoding a fusion polypeptide of a cell-penetration peptide and recombinase is provided.

Kits

In some embodiments kits are provided. The kit can comprise a reversible expression system as described herein, including a AAV vector for expressing a gene product of interest as described herein and a source of recombinase as described herein. In some embodiments, the kit comprises at least one type of cell for expressing the reversible expression system as described herein some embodiments, the cell comprises a mammalian cell suitable for production of gene products, for example a Chinese hamster ovary (CHO) cell, baby hamster kidney (BHK) cell, HeLa cell, monkey kidney cell (COS), human hepatocellular carcinoma cell (e.g. Hep G2), or the like. In some embodiments, the cell comprises a cell suitable for replacement therapy, for example, least one of a hematopoetic stem cell, embryonic stem cell, induced pluripotent stem cell, or the like.

In some embodiments, the kit comprises packaging, instructions, and the like.

Methods of Expressing a Gene Product of Interest

According to some embodiments, reversible gene expression as described herein can be performed in vivo. In some embodiments, a gene product of interest in expressed in a subject for a period of time, and then expression is reduced or eliminated. In some embodiments, the subject is a mammal. The subject can be, in some embodiments, a non-human mammal, for example, a non-human primate such as a monkey, a dog, a cat, a mouse, or a cow. The subject can be in some embodiments, a human. In some embodiments, the human is a participant in a clinical trial. The method can include administering to the subject a first AAV vector configured for reversible gene expression encoding a desired gene product as described herein. The method can include expression of the desired gene product in the subject after administration of the first AAV vector. The method can include administering a recombinase to the subject. The recombinase can induce recombination between at least two of the recombinase target sites of the AAV vector after the first gene product is expressed, thus reducing expression of the first gene product. In some embodiments, the recombinase is administered in a second AAV vector. In some embodiments, the recombinase is administered in an adenovirus vector. In some embodiments, a fusion polypeptide comprising the recombinase and a cell-penetration peptide is administered to the host.

In some embodiments, the method comprises administering to a subject an AAV vector as described herein. In some embodiments, the AAV vector comprises three recombinase target sites as described herein. In some embodiments, the AAV vector comprises five recombinase target sites as described herein. In some embodiments, the AAV vector comprises six recombinase target sites as described herein. Exemplary subjects include, but are not limited to, humans, mice, non-human primates, non-human mammals, cow, sheep, pigs, and the like as described herein. In some embodiments, the AAV vector is administered to a cell that is transplanted into the subject. In some embodiments, the AAV vector comprises one polynucleotide encoding a gene product of interest. In some embodiments, the AAV vector comprises a first polynucleotide encoding a first gene product of interest, and a first polynucleotide encoding a first gene product of interest. In some embodiments, the first and second polynucleotides are separated, in-frame, by a cleavage polynucleotide as described herein. In some embodiments, the first and second polynucleotides are separated by an IRES. In some embodiments, the method comprises expressing both the first and second gene products of interest simultaneously in a subject, for example if the first and second gene products of interest comprise the heavy chain and light chain of an antibody. After the first and second gene products are expressed for a period of time as described herein, the method can comprise reducing or eliminating expression of the first and second gene products of interest. The method can comprise administering a recombinase as described herein to the subject. In some embodiments, the recombinase is administered in a vector. In some embodiments, the recombinase is administered in an AAV vector. In some embodiments, the recombinase is administered in a non-AAV vector, for example an adenovirus vector. In some embodiments, a recombinase polypeptide fused to a cell-penetration peptide is administered to the subject. In some embodiments, the recombinase target sites comprise lox sites as described herein (as such, the recombinase can comprise Cre). In some embodiments, the recombinase target sites comprise FRT sites as described herein (as such, the recombinase can comprise FLPase). Without being limited by any particular theory, administration of the recombinase can induce recombination events between recombinase target sites in the AAV, excising at least portions of the AAV, so as to reduce or eliminate expression of the gene product or products of interest. In some embodiments, administration of the recombinase reduces gene expression at least 10-fold, for example about 10, 20, 50, 100, 200, 500, 1000, 2000, 5000, or 10000-fold, including ranges between any of the listed values.

Reversible gene expression systems, including AAV vectors, other vectors, and polypeptides can be administered to a subject in a variety of ways in accordance with some embodiments herein. In some embodiments, the reversible gene expression system is administered to a subject (e.g., a human or a non-human mammal) in need thereof. The route of the administration is not particularly limited. For example, a therapeutically effective amount of the recombinant viruses can be administered to the subject by via routes standard in the art. Non-limiting examples of the route include intramuscular, intravaginal, intravenous, intraperitoneal, subcutaneous, epicutaneous, intradermal, rectal, intraocular, pulmonary, intracranial, intraosseous, oral, buccal, or nasal. In some embodiments, the expression system or component thereof is administered to the subject by intramuscular injection. In some embodiments, the expression system or component thereof is administered to the subject by intravaginal injection. In some embodiments, the expression system or component thereof is administered to the subject by the parenteral route (e.g., by intravenous, intramuscular or subcutaneous injection), by surface scarification or by inoculation into a body cavity of the subject. Route(s) of administration and serotype(s) of the expression system or component thereof can be readily determined by one skilled in the art taking into account the infection and/or disease state being treated and the target cells/tissue(s) that are to express the protein of interest. In some embodiments, the expression system or component thereof is administered to muscle cells.

Although the exact dosage will be determined on a drug-by-drug basis, in most cases, some generalizations regarding the dosage can be made. In some embodiments, the recombinant AAV expressing a gene product of interest can be administered via injection to a subject at a dose of about $1\times10^9$ genome copies (GC) of the recombinant virus per kg of the subject to about $1\times10^{13}$ GC per kg, for example about $1\times10^9$ GC/kg to $1\times10^{10}$ GC/kg, about $1\times10^9$ GC/kg to $5\times10^{10}$ GC/kg, about $1\times10^9$ GC/kg to $1\times10^{11}$ GC/kg, about $1\times10^9$ GC/kg to $5\times10^{11}$ GC/kg, about $1\times10^9$ GC/kg to $1\times10^{12}$ GC/kg, about $1\times10^9$ GC/kg to $5\times10^{12}$ GC/kg, about $1\times10^9$ GC/kg to $1\times10^{13}$ GC/kg, about $5\times10^9$ GC/kg to $1\times10^{10}$ GC/kg, about $5\times10^9$ GC/kg to $5\times10^{10}$ GC/kg, about $5\times10^9$ GC/kg to $1\times10^{11}$ GC/kg, about $5\times10^9$ GC/kg to $5\times10^{11}$ GC/kg, about $5\times10^9$ GC/kg to $1\times10^{12}$ GC/kg, about $5\times10^9$ GC/kg to $5\times10^{12}$ GC/kg, about $5\times10^9$ GC/kg to $1\times10^{13}$ GC/kg, about $1\times10^{10}$ GC/kg to $5\times10^{10}$ GC/kg, about $1\times10^{10}$ GC/kg to $1\times10^{11}$ GC/kg, about $1\times10^{10}$ GC/kg to $5\times10^{11}$ GC/kg, about $5\times10^{10}$ GC/kg to $1\times10^{12}$ GC/kg, about $1\times10^{10}$ GC/kg to $5\times10^{12}$ GC/kg, about $1\times10^{10}$ GC/kg to $1\times10^{13}$ GC/kg, about $5\times10^{10}$ GC/kg to $1\times10^{11}$ GC/kg, about $5\times10^{10}$ GC/kg to $5\times10^{11}$ GC/kg, about $5\times10^{10}$ GC/kg to $1\times10^{12}$ GC/kg, about $5\times10^{10}$ GC/kg to $5\times10^{12}$ GC/kg, about $5\times10^{10}$ GC/kg to $1\times10^{13}$ GC/kg, about $1\times10^{11}$ GC/kg to $5\times10^{11}$ GC/kg, about $1\times10^{11}$ GC/kg to $1\times10^{12}$ GC/kg, about $1\times10^{11}$ GC/kg to $5\times10^{12}$ GC/kg, about $1\times10^{11}$ GC/kg to $1\times10^{13}$ GC/kg, about $5\times10^{11}$ GC/kg to $1\times10^{12}$ GC/kg, or about $5\times10^{11}$ GC/kg to $1\times10^{13}$ GC/kg. In some embodiments, for example if the administered source of recombinase comprises a vector encoding the recombinase, the recombinase vector is delivered at least the dose, or more preferably, an excess of the dose of the AAV vector encoding the gene product of interest.

Actual administration of the AAV vector encoding a gene product of interest, expression system, or component thereof can be accomplished by using any physical method that will transport the recombinant AAV vector into the target tissue of the subject. For example, the recombinant AAV vector can be injected into muscle, the bloodstream, and/or directly into the liver. Capsid proteins of the recombinant AAV vector may be modified so that the recombinant AAV vector is targeted to a particular target tissue of interest such as muscle or bone marrow. Pharmaceutical compositions can be prepared as injectable formulations or as topical formulations to be delivered to the muscles by transdermal transport.

For intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the AAV vector as a free acid (DNA contains acidic phosphate groups) or a pharmacologically acceptable salt can be prepared in water suitably mixed with a surfactant such as hydroxpropylcellulose. A dispersion of the AAV vector can also be prepared in glycerol, liquid polyethylene glycols and mixtures thereof and in oils. Under ordinary conditions of storage and use, these preparations contain a preservative to prevent the growth of microorganisms.

The AAV vector to be used can be utilized in liquid or freeze-dried form (in combination with one or more suitable preservatives and/or protective agents to protect the virus during the freeze-drying process). For gene therapy (e.g., of neurological disorders which may be ameliorated by a specific gene product) a therapeutically effective dose of the recombinant virus expressing the therapeutic protein is administered to a host in need of such treatment. The use of the recombinant virus disclosed herein in the manufacture of a medicament for inducing immunity in, or providing gene therapy to, a host is within the scope of the present application. In some embodiments, the AAV can be administered to a cell that is subsequently transplanted into the host, for example a hematopoietic stem cell, embryonic stem cell, induced pluripotent stem cell, or the like.

In instances where human dosages for the AAV vectors have been established for at least some condition, those same dosages, or dosages that are between about 0.1% and 500%, more preferably between about 25% and 250% of the established human dosage can be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

A therapeutically effective amount of the AAV vector encoding a gene product of interest can be administered to a subject at various points of time. For example, the AAV vector can be administered to the subject prior to, during, or after the infection by a virus. The AAV vector can also be administered to the subject prior to, during, or after the occurrence of a disease (e.g., cancer). In some embodiments, the AAV vector is administered to the subject during cancer remission. In some embodiments, the AAV vector is administered prior to infection by the virus for immunoprophylaxis.

The dosing frequency of the AAV vector can vary. For example, the AAV vector can be administered to the subject about once every week, about once every two weeks, about once every month, about one every six months, about once every year, about once every two years, about once every three years, about once every four years, about once every five years, about once every six years, about once every seven years, about once every eight years, about once every nine years, about once every ten years, or about once every fifteen years. In some embodiments, the AAV vector is administered to the subject at most about once every week, at most about once every two weeks, at most about once every month, at most about one every six months, at most about once every year, at most about once every two years, at most about once every three years, at most about once every four years, at most about once every five years, at most about once every six years, at most about once every seven years, at most about once every eight years, at most about once every nine years, at most about once every ten years, or at most about once every fifteen years.

In some embodiments the source of the recombinase is administered at the same time as the AAV vector. In some embodiments, a mixture of AAV vector encoding the gene product of interest and the recombinase source is administered. In some embodiments, for example if the recombinase provided in a vector and is under the control of an inducible promoter, the recombinase is administered but is not active at or immediately after administration. Recombinase activity can subsequently be induced to reduce or eliminate expression of the gene product of interest. In some embodiments, for example if the recombinase target sites of the AAV vector comprise lox sites, the recombinase comprises Cre. In some embodiments, for example if the recombinase target sites of the AAV comprise FRT sites, the recombinase comprises FLPase. In some embodiments, the recombinase is administered along the same route of administration as the AAV encoding the gene product of interest. In some embodiments, the source of recombinase is administered via a different route administration than the AAV encoding the gene product of interest, for example intramuscular, intravaginal, intravenous, intraperitoneal, subcutaneous, epicutaneous, intradermal, rectal, intraocular, pulmonary, intracranial, intraosseous, oral, buccal, or nasal. In some embodiments, the source of recombinase is delivered at a greater dose that the AAV vector encoding the gene product of interest. For example, in some embodiments in which the recombinase is administered as a vector, at least a 2-fold ratio of recombinase vector to AAV vector encoding gene product of interest can be administered, for example at least about a 2, 3, 4, 5, 6, 7, 8, 9, 10, 15, 20, 30, 40, 50, 100, 200, 500, 1000, 1500, 2000, 5000, 10,000, 20,000, 50,000, 100,000, 500,000, or 1,000,000,000-fold ratio of recombinase vector to AAV vector.

In some embodiments, the source of recombinase is provided after the AAV vector is administered to the subject. In some embodiments, the source of recombinase is provided after the gene product of interest has been expressed from the AAV vector. In some embodiments, expression of the gene product of interested is monitored in the subject (for example through direct monitoring of levels of gene product, or through monitoring of biomarkers indicative of levels of gene product or gene product activity), and the source of recombinase is subsequently administered to the subject. In some embodiments, the source of recombinase is administered to the subject upon or after the subject reaching a clinical endpoint. In some embodiments, the source of recombinase is administered to the subject if the subject experiences undesired side effects from the AAV vector encoding the gene product of interest. In some embodiments, the source of recombinase is administered at least about 1 week after the AAV vector encoding the gene product of interest is administered to the subject, for example about 1 week, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 78, 179, 180, 181, 182, 183, 184, 185, 186, 187, 188, 189, 190, 191, 192, 193, 194, 195, 196, 197, 198, 199, or 200 weeks after, including ranges between any two of the listed values.

In some embodiments, upon administration, the source of recombinase provides recombinase activity, which results in a fold-reduction of expression and/or activity of the gene product of interest. In some embodiments, expression, activity, or expression and activity of the gene product of interest are reduced at least about 10-fold, for example about $1 \times 10^1$, $5 \times 10^1$, $1 \times 10^2$, $5 \times 10^2$, $1 \times 10^3$, $5 \times 10^3$, $1 \times 10^4$, $5 \times 10^4$, $1 \times 10^5$, $5 \times 10^5$, $1 \times 10^6$, or $5 \times 10^6$-fold. In some embodiments, prior to recombinase administration, the AAV vector encoding a gene product of interest produces at least a comparable yield of gene product and gene product activity as a comparable AAV vector lacking the recombinase sites. In some embodiments, the addition recombinase eliminates or substantially eliminates expression and/or activity of the gene product of interest.

In some embodiments, addition of the recombinase induces recombination between one pair of the recombinase target sites of the AAV vector encoding the gene product of interest. In some embodiments, addition of the recombinase induces recombination between at least two pairs of the recombinase target sites of the AAV vector encoding the gene product of interest, for example two, three, four, five, six, seven, eight, nine, or ten pairs of recombinase target sites as described herein.

In some embodiments, the AAV encodes a heavy chain and a light chain of an immunoglobulin as described herein. In some embodiments, the immunoglobulin is an antibody. In some embodiments, the antibody binds specifically to a pathogen, for example a virus such as HIV, and thus can be administered as an immunoprophylactic vaccine. In some embodiments, the polynucleotides encoding the heavy chain and light chain are orientated in the same orientation and operationally linked to a promoter of the AAV. A cleavage polynucleotide, for example a 2A polynucleotide can be positioned in-frame between the heavy chain and light chain polynucleotide. In some embodiments, the polynucleotide encoding the heavy chain is upstream (5') of the polynucleotide encoding the light chain. In some embodiments, the polynucleotide encoding the light chain is upstream (5') of the polynucleotide encoding the heavy chain. In some embodiments, the heavy chain and light chain are administered on separate AAV vectors configured for reversible gene expression as described herein, and each AAV vector comprises recombinase target sites configured to reduce or eliminate expression of the respective heavy or light chain upon the addition of recombinase. In some embodiments, the heavy chain and light chain are administered on separate vectors, and only one of the two vectors (heavy chain or light chain) comprises an AAV vector configured for reversible gene expression as described herein.

Example 1: Transfection of 293T Cells with LoxP Constructs +/−Cre (1 LoxP Site)

293T cells were transfected with AAV vector comprising a CASI promoter which was operatively linked to a luciferase coding sequence (Luc2), a full-length WPRE, and an SV40 polyadenylation site (see FIG. 2A). Vector 1490 had no LoxP sites. Each of vectors 1592, 1593, 1595, and 1602 had one LoxP site, positioned as shown in FIG. 2C (solid arrows). For each vector, one population of cells was cotransfected with pUC (control), while another population was cotransfected with a separate plasmid encoding Cre recombinase. As shown in FIG. 2B, each vector produced approximately the same Luciferase activity (RLU) in the presence or absence of Cre.

Example 2: Transfection of 293T Cells with LoxP Constructs +/−Cre (2 LoxP Sites)

293T cells were transfected with AAV vector comprising a CASI promoter which was operatively linked to a luciferase coding sequence (Luc2), a full-length WPRE, and an SV40 polyadenylation site (see FIG. 3A). Vector 1490 had no LoxP sites. Each of vectors 1594, 1603, 1604, and 1608 had two LoxP sites, positioned as shown in FIG. 3C (solid arrows). For each vector, one population of cells was cotransfected with pUC (control), while another population was cotransfected with a separate plasmid encoding Cre recombinase. As shown in FIG. 3B, cotransfection with Cre yielded substantially reduced luciferase activity (about $10^2$-fold) for vectors 1603 and 1604 (each of which had LoxP sites in the same orientation, as shown), but not for vectors 1490, 1594, and 1680. Since 1490 lacks LoxP sites, and 1608 possesses LoxP sites in opposite orientations flanking the promoter, coding, and regulatory sequences (and thus would be expected to invert the flanked sequences), the insubstantial effect of Cre on luciferase activity was as expected. On the other hand, as 1594 possessed LoxP sites in the same orientation flanking the vector, it was unexpected that Cre did not reduce luciferase activity for this vector, as Cre would have been expected to mediate a recombination event that excised the promoter, coding, and regulatory sequences from the vector.

Example 3: Transfection of 293T Cells with LoxP Constructs +/−Cre (3 LoxP Sites)

Figure 4A:
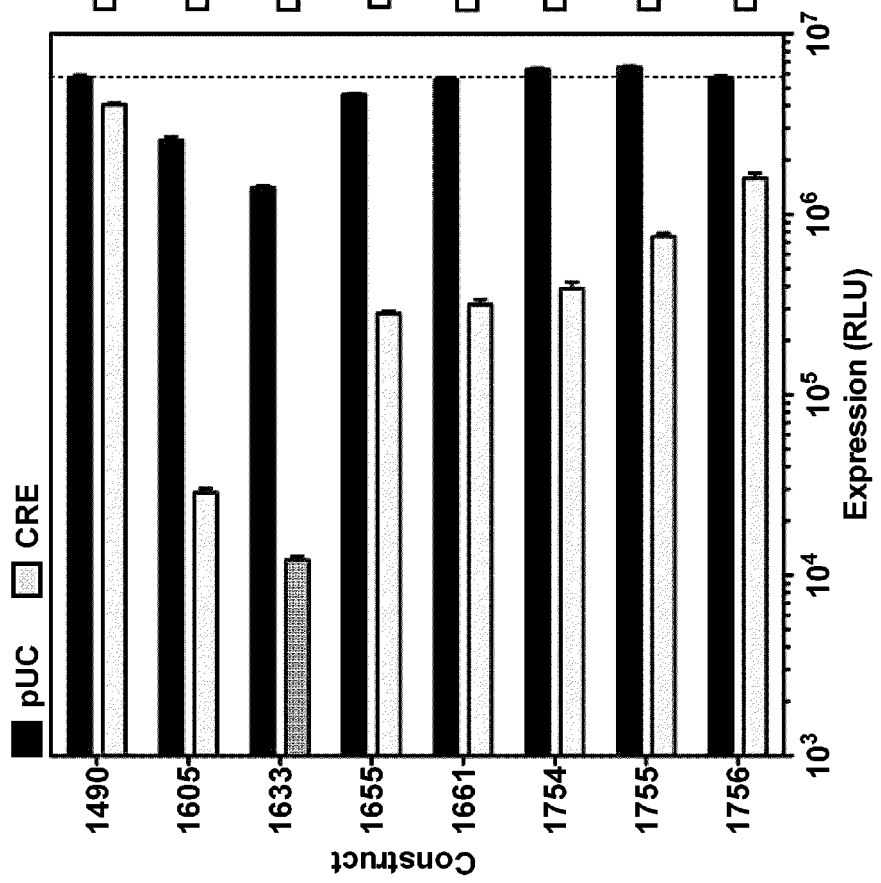
FIG. 4A is a graph illustrating luciferase activity in 293T cells transfected with AAV constructs according to some embodiments herein. The constructs contained three loxP sites, and luciferase activity for each construct was observed in the absence of CRE (i.e., pUC) and the presence or CRE.
Figure 4B:
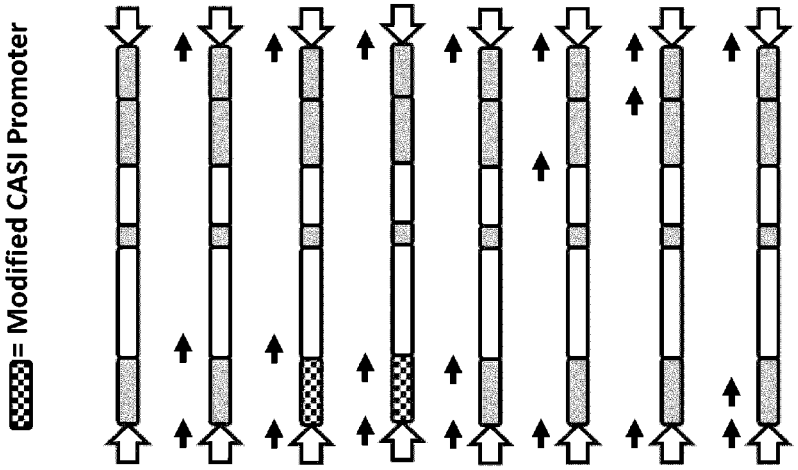
FIG. 4B is a schematic diagram illustrating the position of the loxP sites for each of the constructs used in the experiment depicted in FIG. 4A. For each experiment (e.g. each pair of bars) in FIG. 4A, the corresponding construct schematic is shown in FIG. 4B to the right of the bars. LoxP sites (and relative orientations) are depicted as solid arrows.

293T cells were transfected with AAV vector comprising a CASI promoter or modified CASI promoter which was operatively linked to a luciferase coding sequence (Luc2), a full-length WPRE, and an SV40 polyadenylation site. Vector 1490 had no LoxP sites. Each of vectors 1605, 1633, 1655, 1661, 1754, 1755, and 1756 had three LoxP sites, positioned as shown in FIG. 4B (solid arrows). Vectors 1490, 1605, 1661, 1754, 1755, and 1756 had a CASI promoter. Vectors 1633 and 1655 had a modified CASI promoter, in which Lox P sites were inserted within the promoter sequence (see FIG. 1B, in which positions of solid arrows indicate placement of LoxP sites). In each modified CASI promoter, a first LoxP site was positioned either upstream or downstream of the splice donor, and a second LoxP site was positioned either upstream or downstream of the splice acceptor. For each vector, one population of cells was cotransfected with pUC (control), while another population was cotransfected with a separate plasmid encoding Cre recombinase. As shown in FIG. 4A, cotransfection with Cre yielded substantially reduced luciferase activity (about $10^3$ to $10^4$-fold) for vectors 1605 and 1633 (each of which had LoxP sites in the same orientation, with one LoxP site upstream of the promoter, and one LoxP site immediately downstream of the promoter; see FIG. 4B). It is noted that for the remaining vectors (1655, 1661, 1754, 1755, 1756), even though all of the LoxP sites were in the same orientation and positioned throughout the construct, they did not reduce expression nearly as much as for vectors 1605 and 1633.

Example 4: Transfection of 293T Cells with LoxP Constructs +/−Cre (4 LoxP Sites)

Figure 5A:
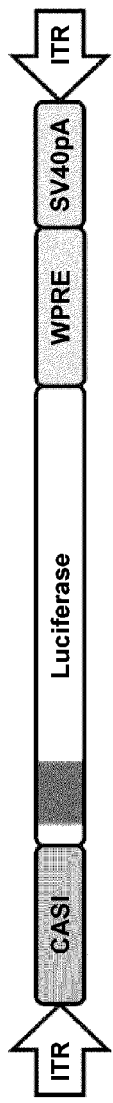
FIG. 5A is a schematic diagram of an adeno-associated vector for expressing a gene product of interest in accordance with some embodiments herein.
Figure 5C:
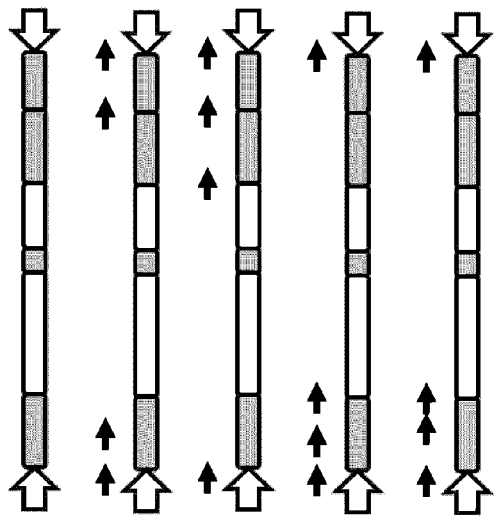
FIG. 5C is a schematic diagram illustrating the position of the loxP sites for each of the constructs used in the experiment depicted in FIG. 5B. For each experiment (e.g. each pair of bars) in FIG. 5B, the corresponding construct schematic is shown in FIG. 5C to the right of the bars. LoxP sites (and relative orientations) are depicted as solid arrows.
Figure 5B:
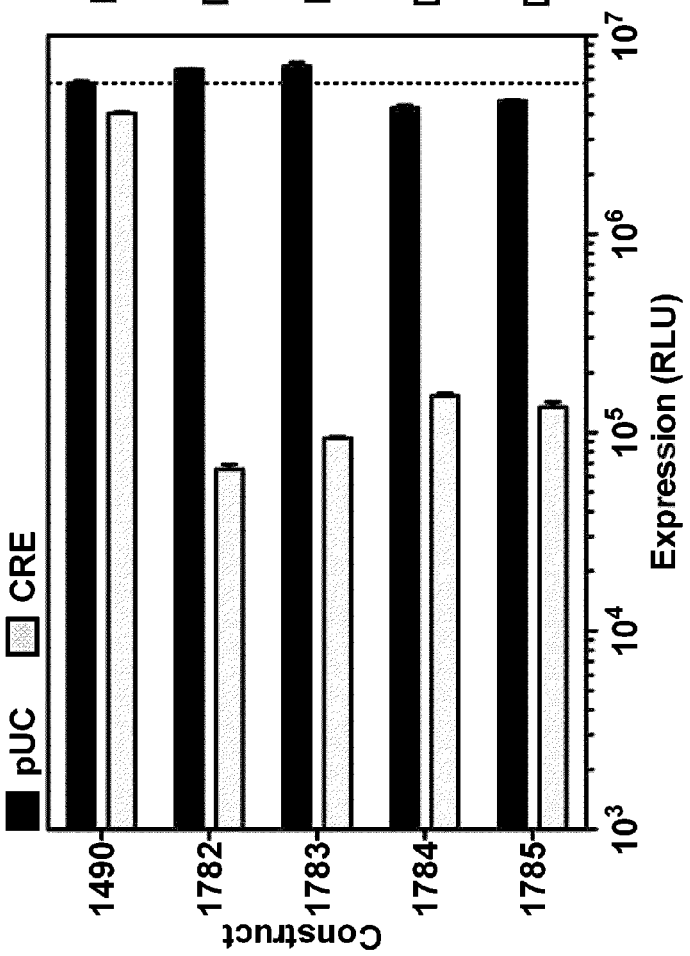
FIG. 5B is a graph illustrating luciferase activity in 293T cells transfected with AAV constructs according to some embodiments herein. The constructs were based on the vector of FIG. 5A and contained four loxP sites. Luciferase activity for each construct was observed in the absence of CRE (i.e., pUC) and the presence or CRE.

293T cells were transfected with AAV vector comprising a CASI promoter which was operatively linked to a luciferase coding sequence (Luc2), a full-length WPRE, and an SV40 polyadenylation site. Vector 1490 had no LoxP sites. Each of vectors 1782, 1783, 1784, and 1785 had four LoxP sites, positioned as shown in FIG. 5C (solid arrows). For each vector, one population of cells was cotransfected with pUC (control), while another population was cotransfected with a separate plasmid encoding Cre recombinase. As shown in FIG. 5B, cotransfection with Cre yielded substantially reduced luciferase activity (about $10^2$-fold) for vectors 1782, 1783, 1784, and 1785 (each of which four had LoxP sites in the same orientation; see FIG. 5B).

Example 5: Transfection of 293T Cells with LoxP Constructs +/−Cre (5 LoxP Sites)

Figure 6B:
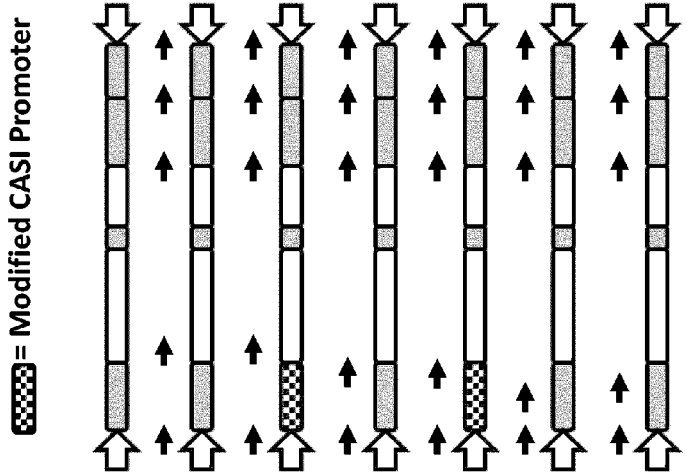
FIG. 6B is a schematic diagram illustrating the position of the loxP sites for each of the constructs used in the experiment depicted in FIG. 6A. For each experiment (e.g. each pair of bars) in FIG. 6A, the corresponding construct schematic is shown in FIG. 6B to the right of the bars. LoxP sites (and relative orientations) are depicted as solid arrows.
Figure 6A:
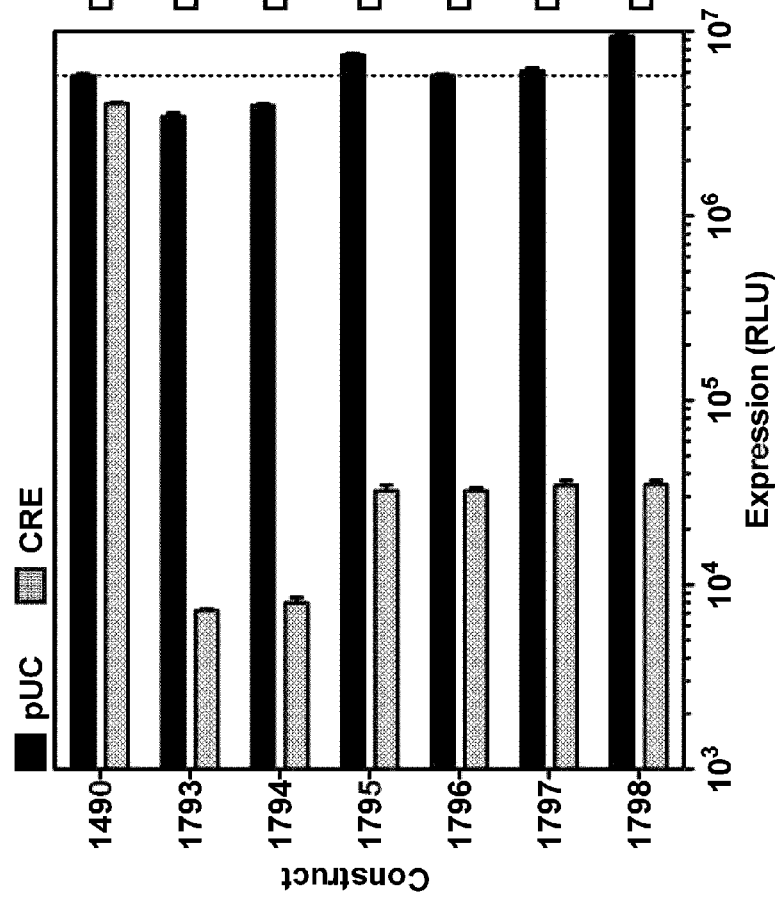
FIG. 6A is a graph illustrating luciferase activity in 293T cells transfected with AAV constructs according to some embodiments herein. Each construct contained five loxP sites. Luciferase activity for each construct was observed in the absence of CRE (i.e., pUC) and the presence or CRE.

293T cells were transfected with AAV vector comprising a CASI promoter or modified CASI promoter which was operatively linked to a luciferase coding sequence (Luc2), a full-length WPRE, and an SV40 polyadenylation site. Vector 1490 had no LoxP sites. Each of vectors 1793, 1794, 1795, 1796, 1797, and 1798 had five LoxP sites, positioned as shown in FIG. 6B (solid arrows). Vectors 1490, 1793, 1795, 1797, and 1798 had a CASI promoter. Vectors 1794 and 1796 had a modified CASI promoter, in which LoxP sited were inserted into the promoter sequence as described herein. For each vector, one population of cells was cotransfected with pUC (control), while another population was cotransfected with a separate plasmid encoding Cre recombinase. As shown in FIG. 6A, cotransfection with Cre yielded substantially reduced luciferase activity for vectors 1793, 1794, 1795, 1796, 1797, and 1798 (about $10^2$-fold), with expression especially low (about $10^3$-fold) for vectors 1793 and 1794 (each of which had a LoxP site upstream of the promoter, and another LoxP site immediately downstream of the promoter, both in the same orientation; see FIG. 6B).

Example 6: Transfection of 293T Cells with LoxP Constructs +/−Cre (6 LoxP Sites)

Figure 7A:
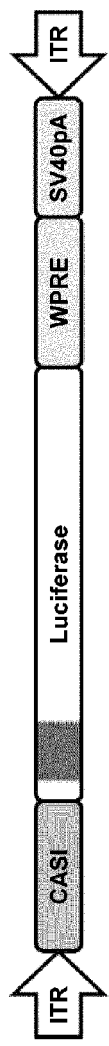
FIG. 7A is a schematic diagram of an adeno-associated vector for expressing a gene product of interest in accordance with some embodiments herein.
Figure 7C:
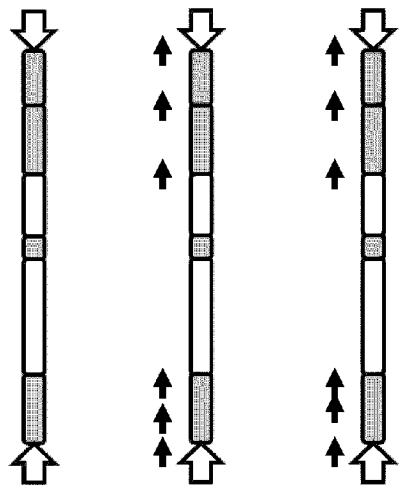
FIG. 7C is a schematic diagram illustrating the position of the loxP sites for each of the constructs used in the experiment depicted in FIG. 7B. For each experiment (e.g. each pair of bars) in FIG. 7B, the corresponding construct schematic is shown in FIG. 7C to the right of the bars. LoxP sites (and relative orientations) are depicted as solid arrows.
Figure 7B:
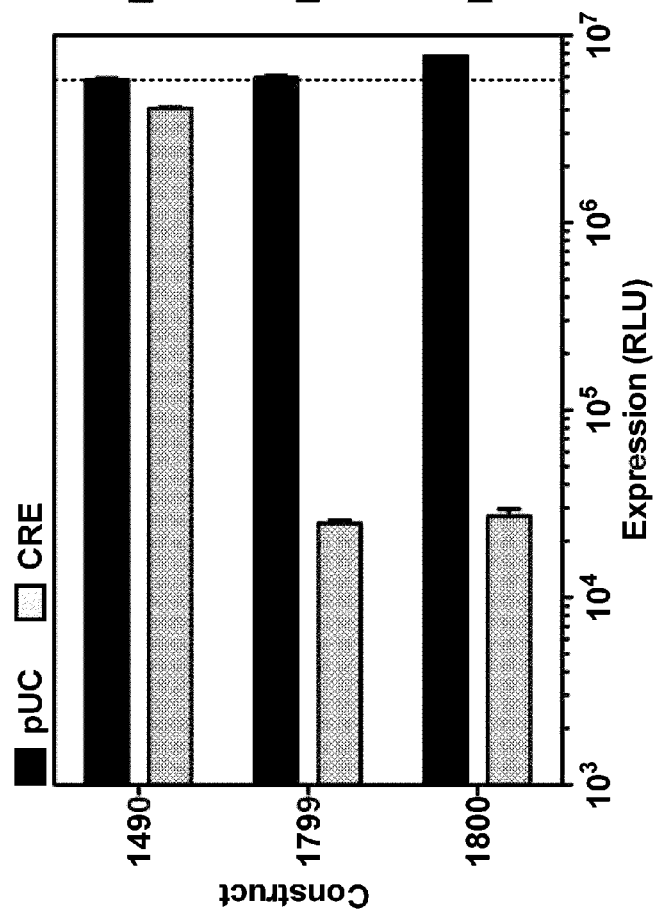
FIG. 7B is a graph illustrating luciferase activity in 293T cells transfected with AAV constructs according to some embodiments herein. The AAV constructs were based on the vector of FIG. 7A, and contained six loxP sites. Luciferase activity for each construct was observed in the absence of CRE (i.e., pUC) and the presence or CRE.

293T cells were transfected with AAV vector comprising a CASI promoter or modified CASI promoter which was operatively linked to a luciferase coding sequence (Luc2), a full-length WPRE, and an SV40 polyadenylation site. Vector 1490 had no LoxP sites. Each of vectors 1799 and 1800 had six LoxP sites, positioned as shown in FIG. 7C (solid arrows). For each vector, one population of cells was cotransfected with pUC (control), while another population was cotransfected with a separate plasmid encoding Cre recombinase. As shown in FIG. 7B, cotransfection with Cre yielded substantially reduced luciferase activity (about $10^3$-fold) for vectors 1799 and 1800.

Example 7: Transfection of 293T Cells with Shortened LoxP Constructs +/−Cre (5 LoxP Sites)

AAV vectors with CASI promoters operatively linked to a luciferase coding sequence (Luc2), shortened WPRE sites and/or SV40 sites were prepared as shown in FIG. 8B. Control vector 1490 had a full-length WPRE (SEQ ID NO: 27) and an SV40 polyadenylation sequence (SEQ ID NO: 26) and no LoxP sites as shown in FIG. 8B. Vector 1798 had a full-length WPRE (SEQ ID NO: 27) and an SV40 polyadenylation sequence (SEQ ID NO: 26) and five LoxP sites as shown in FIG. 8B. Vector 1801 had a full-length WPRE (SEQ ID NO: 27) and a synthetic polyadenylation sequence (SEQ ID NO: 43) and five LoxP sites as shown in FIG. 8B. Vector 1803 had a "No X" WPRE (SEQ ID NO: 28) and an SV40 polyadenylation sequence (SEQ ID NO: 26) and five LoxP sites as shown in FIG. 8B. Vector 1804 had a "short" WPRE (SEQ ID NO: 29) and an SV40 polyadenylation sequence (SEQ ID NO: 26) and five LoxP sites as shown in FIG. 8B. Vector 1807 had a "No X" WPRE (SEQ ID NO:28) and a synthetic polyadenylation sequence (SEQ ID NO: 43) and five LoxP sites as shown in FIG. 8B. Vector 1808 had a "short" WPRE (SEQ ID NO: 29) and a synthetic polyadenylation sequence (SEQ ID NO: 43) and five LoxP sites as shown in FIG. 8B.

293T cells were transfected with the indicated vectors. For each vector, one population of cells 293T cells were transfected with AAV vector comprising a CASI promoter which was operatively linked to a luciferase coding sequence (Luc2), a full-length WPRE, and an SV40 polyadenylation site was cotransfected with pUC (control), while another population was cotransfected with a separate plasmid encoding Cre recombinase. As shown in FIG. 8A, cotransfection with Cre yielded substantially reduced luciferase activity for vectors 1798, 1801, 1803, 1804, 1807, and 1808. It is noted that in the absence of Cre, vectors 1803, 1804, 1807, and 1808 produced comparable luciferase expression to the other vectors, but had much shorter WPREs.

Example 8: Transfection of 293T Cells with Shortened LoxP Constructs +/−Cre (6 LoxP Sites)

AAV vectors with CASI promoters operatively linked to a luciferase coding sequence (Luc2), shortened WPRE sites and/or SV40 sites were prepared as shown in FIG. 9B. Control vector 1490 had a full-length WPRE (SEQ ID NO: 27) and an SV40 polyadenylation sequence (SEQ ID NO: 26) and no LoxP sites as shown in FIG. 9B. Vector 1800 had a full-length WPRE (SEQ ID NO: 27) and an SV40 polyadenylation sequence (SEQ ID NO: 26) and six LoxP sites as shown in FIG. 9B. Vector 1802 had a full-length WPRE (SEQ ID NO: 27) and a synthetic polyadenylation sequence (SEQ ID NO: 43) and six LoxP sites as shown in FIG. 9B. Vector 1805 had a "short" WPRE (SEQ ID NO: 29) and an SV40 polyadenylation sequence (SEQ ID NO: 26) and six LoxP sites as shown in FIG. 9B. Vector 1806 (SEQ ID NO: 1) had a "no X" WPRE (SEQ ID NO: 28) and an SV40 polyadenylation sequence (SEQ ID NO: 26) and six LoxP sites as shown in FIG. 9B. Vector 1809 had a "short" WPRE (SEQ ID NO: 29) and a synthetic polyadenylation sequence (SEQ ID NO: 43) and six LoxP sites as shown in FIG. 9B. Vector 1810 had a "no X" WPRE (SEQ ID NO: 28) and a synthetic polyadenylation sequence (SEQ ID NO: 43) and six LoxP sites as shown in FIG. 9B.

293T cells were transfected with the indicated vectors. For each vector, one population of cells 293T cells were transfected with AAV vector comprising a CASI promoter which was operatively linked to a luciferase coding sequence (Luc2), a full-length WPRE, and an SV40 polyadenylation site was cotransfected with pUC (control), while another population was cotransfected with a separate plasmid encoding Cre recombinase. As shown in FIG. 9A, cotransfection with Cre yielded substantially reduced luciferase activity for vectors 1800, 1802, 1805, 1806, and 1809. It is noted that in the absence of Cre, vectors 1805, 1806, and 1810 produced comparable luciferase expression to the other vectors, but had much shorter WPREs.

Example 9: In Vivo Testing of LoxP AAV Vectors

Figure 10:
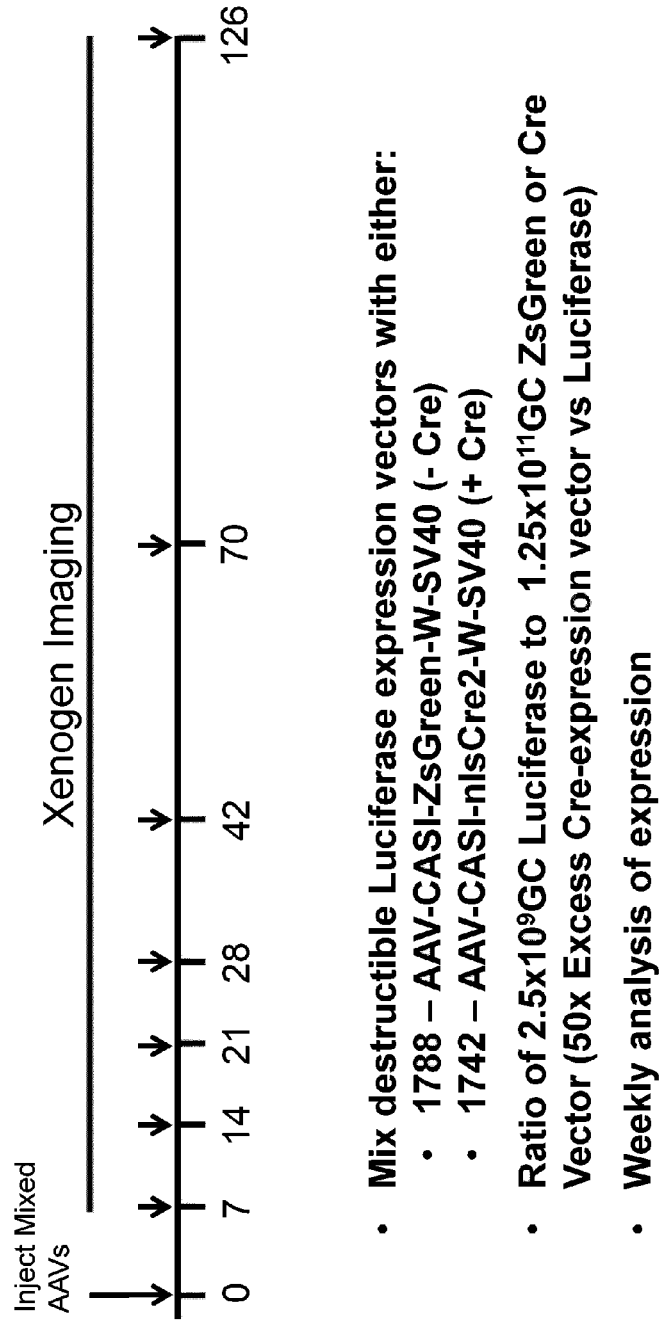
FIG. 10 is a schematic diagram illustrating an experimental protocol for reversibly expressing gene products encoded by AAV vector according to some embodiments herein.
Figure 11:
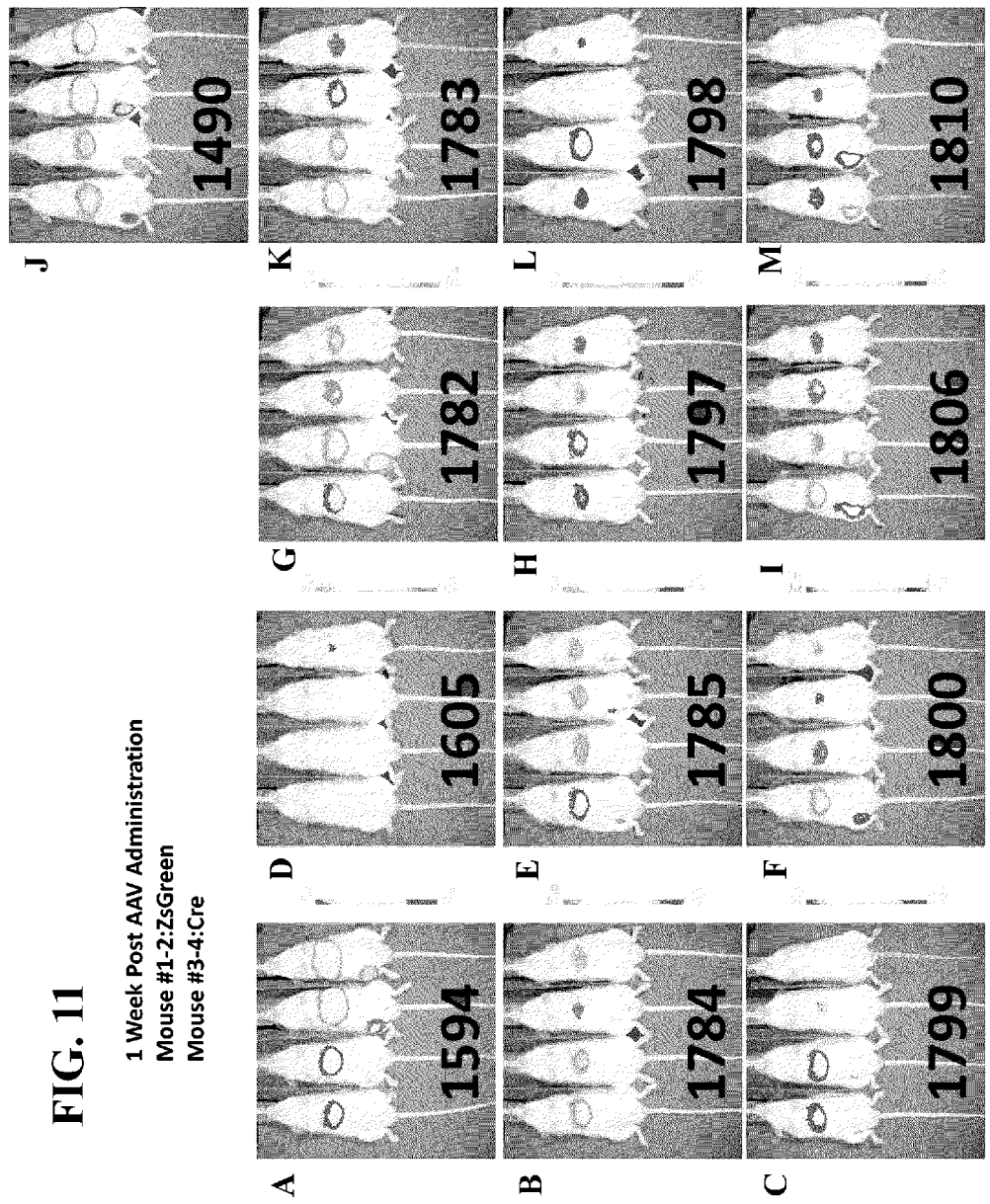
FIG. 11 is a series of photographs illustrating Xenogen imaging of mice injected with AAV (AAV) vectors in accordance with some embodiments herein. Each mouse was injected with the indicated adeno-associated vector encoding luciferase. Mice 1 and 2 (from left) were injected with a mixture of AAV vector encoding luciferase and AAV vector encoding ZsGreen. Mice 3 and 4 (from left) were injected with a mixture of AAV vector encoding luciferase and AAV vector encoding Cre. The images of FIG. 11 were taken one week after administering the Cre.
Figure 12:
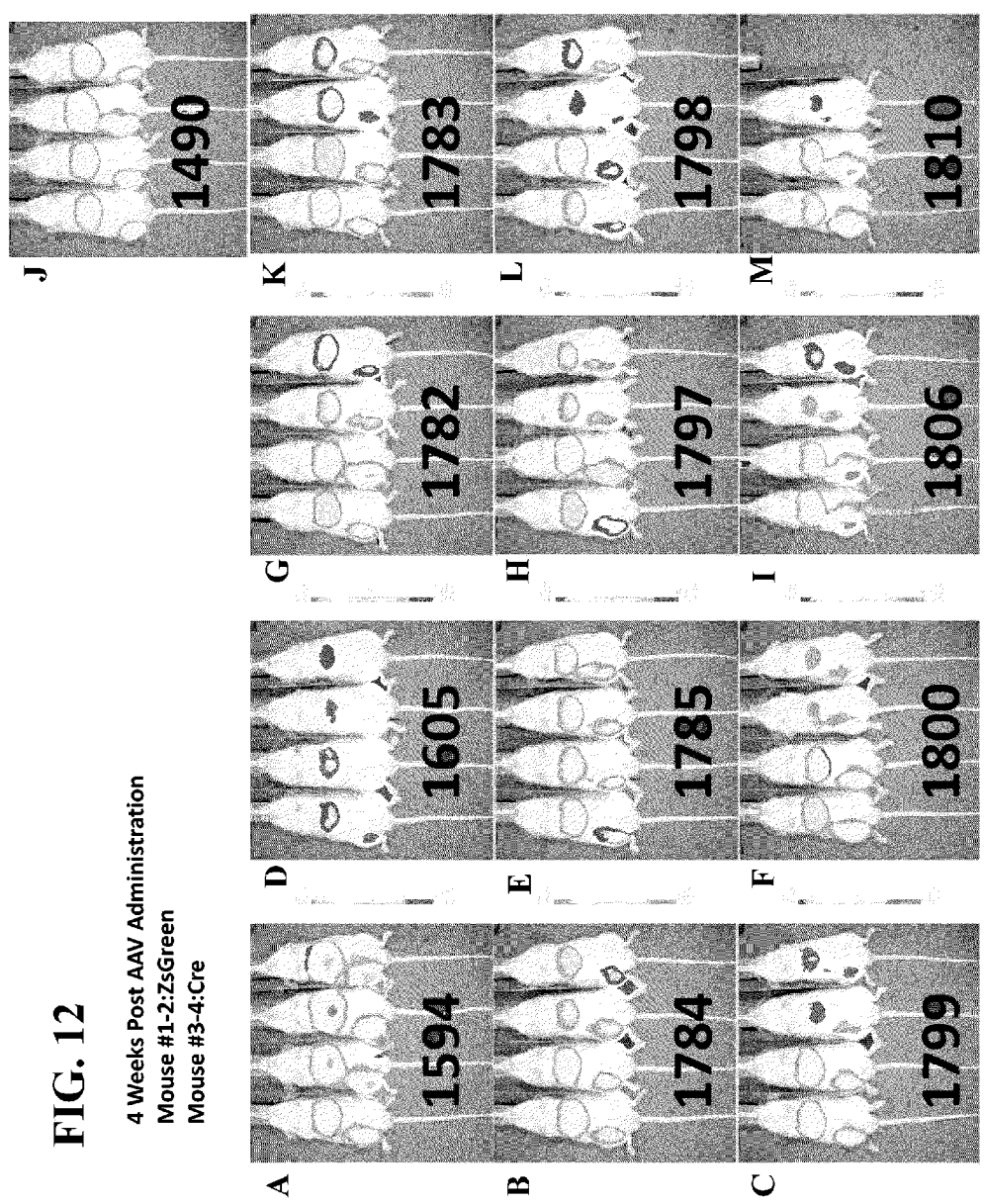
FIG. 12 is a series of photographs illustrating Xenogen imaging of mice injected with AAV vectors in accordance with some embodiments herein. Each mouse was injected with the indicated adeno-associated vector encoding luciferase. Mice 1 and 2 (from left) were injected with a mixture of AAV vector encoding luciferase and AAV vector encoding ZsGreen. Mice 3 and 4 (from left) were injected with a mixture of AAV vector encoding luciferase and AAV vector encoding Cre. The images of FIG. 12 were taken four weeks after administering the CRE.
Figure 14:
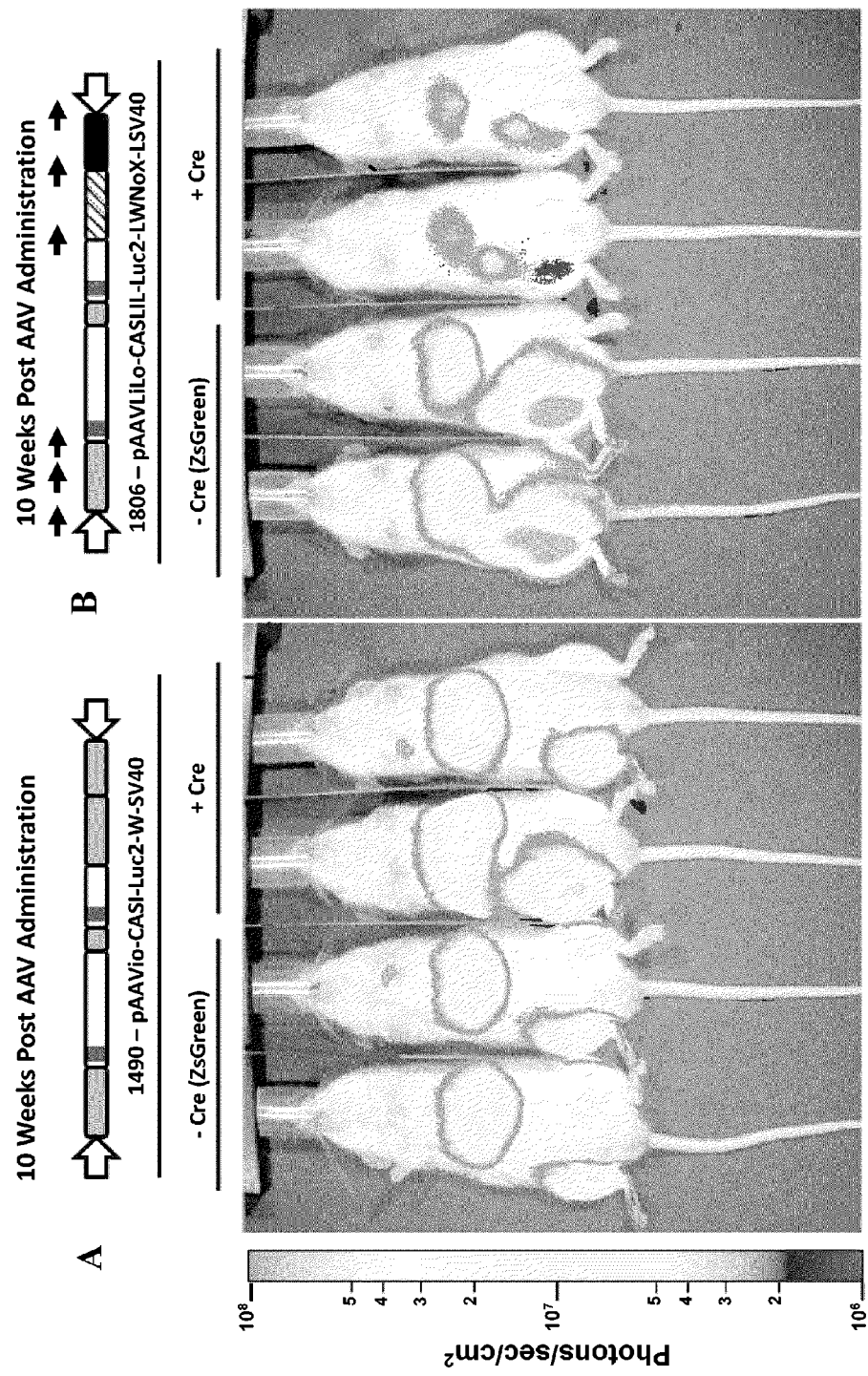
FIG. 14 is a series of photographs and schematics illustrating Xenogen imaging of mice injected with AAV vectors in accordance with some embodiments herein. The Xenogen images were taken 10 weeks after administration of the indicated vectors.
Figure 15:
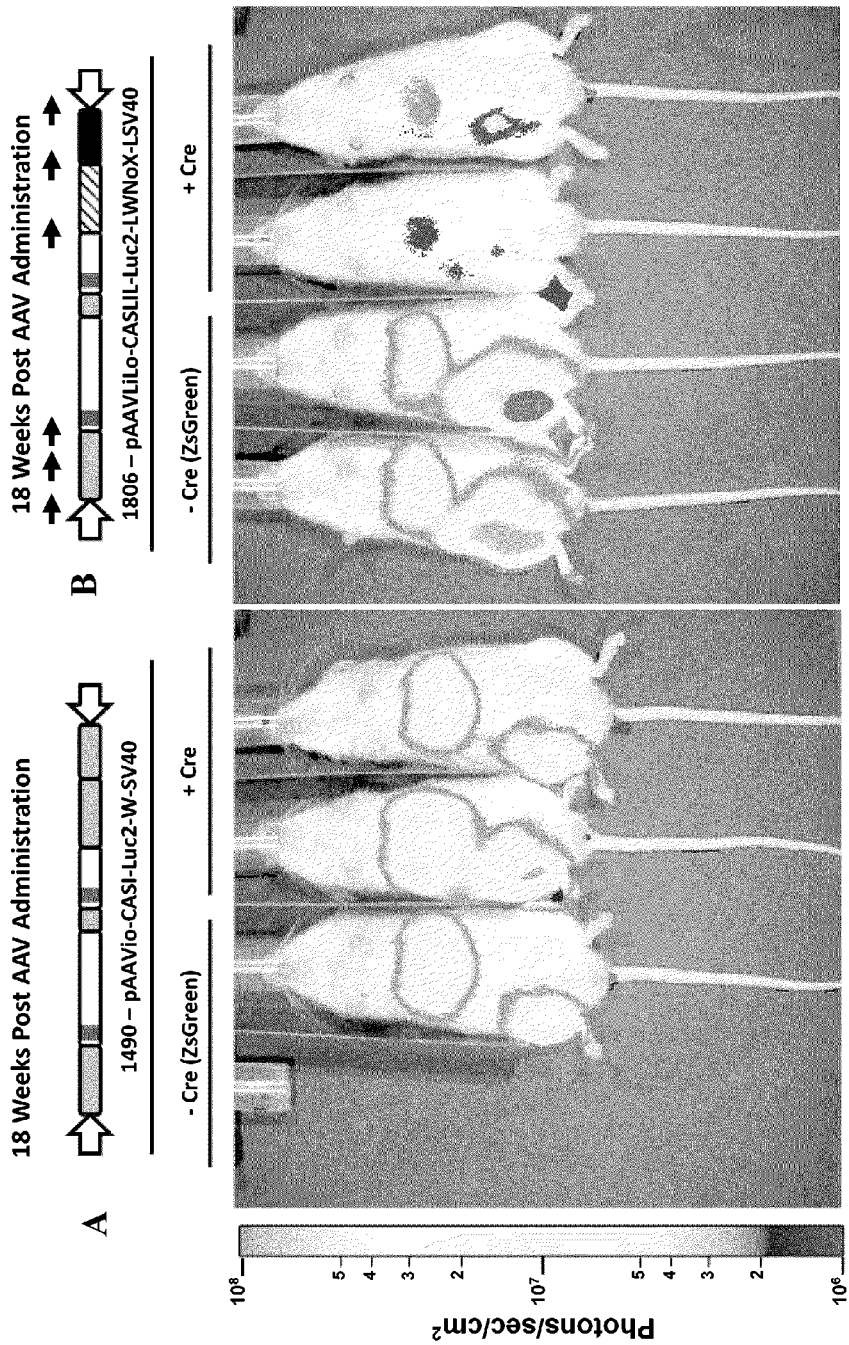
FIG. 15 is a series of photographs and schematics illustrating Xenogen imaging of mice injected with AAV vectors in accordance with some embodiments herein. The Xenogen images were taken 18 weeks after administration of the indicated vectors.
Figure 16:
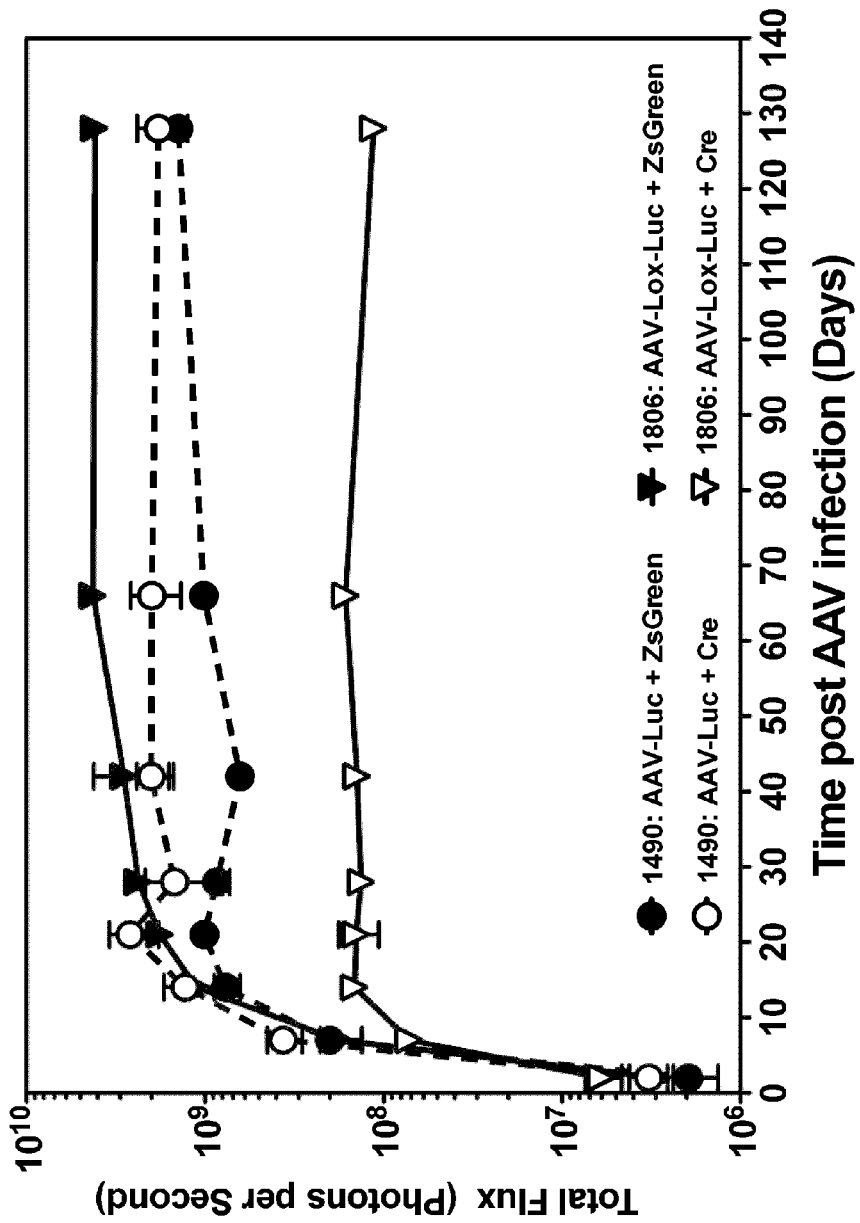
FIG. 16 is a graph illustrating luciferase activity in mice at various timepoints after infection with AAV vectors according to some embodiments herein. Shown is luciferase activity for mice injected with vector 1490, encoding AAV and luciferase (but no Lox sites; see, e.g., FIGS. 14A and 15A), and cotransfected with either ZsGreen (no Cre) or Cre. Shown is luciferase activity for mice transfected with vector 1806, encoding luciferase and comprising six LoxP sites (see, e.g., FIGS. 14B and 15B), and cotransfected with either ZsGreen (no Cre) or Cre.

LoxP AAV vectors in accordance with some embodiments herein encoding luciferase were injected into mice. Each luciferase vector was injected into four mice, of which two received a mixture of AAV vector encoding luciferase and control AAV vector 1788—AAV-CASI-ZsGreen-W-SV40 ("ZsGreen;" no Cre), and two received a mixture AAV vector encoding luciferase and Cre-encoding AAV vector 1742—AAV-CASI-nlsCre2-W-SV40 (+Cre). The vectors were provided at a ratio of $2.5 \times 10^9$ GC Luciferase to $1.25 \times 10^{11}$ GC ZsGreen or Cre Vector, which represented a 50× Excess Cre-expression vector versus Luciferase-encoding vector. Luciferase expression was monitored via Xenogen imaging at 7, 14, 21, 28, 42, 70, and 126 days after injection. The design of this experiment is schematically illustrated in FIG. 10. Xenogen imaging of luciferase activity at 7 days after injection is shown in FIGS. 11A-11M. Xenogen imaging of luciferase activity at 4 weeks after injection is shown in FIGS. 12A-12M. Representative Xenogen imaging 10 weeks after AAV administration is shown in FIGS. 14A (vector 1490; no LoxP sites) and 14B (vector 1806; six loxP sites). Representative Xenogen imaging 18 weeks after AAV administration is shown in FIGS. 14A (vector 1490; no LoxP sites) and 14B (vector 1806; six loxP sites). Notably, at both 10 and 18 weeks, the mice that received vector 1806 (six loxP sites) and Cre have substantially less luciferase activity than controls.

Figure 13:
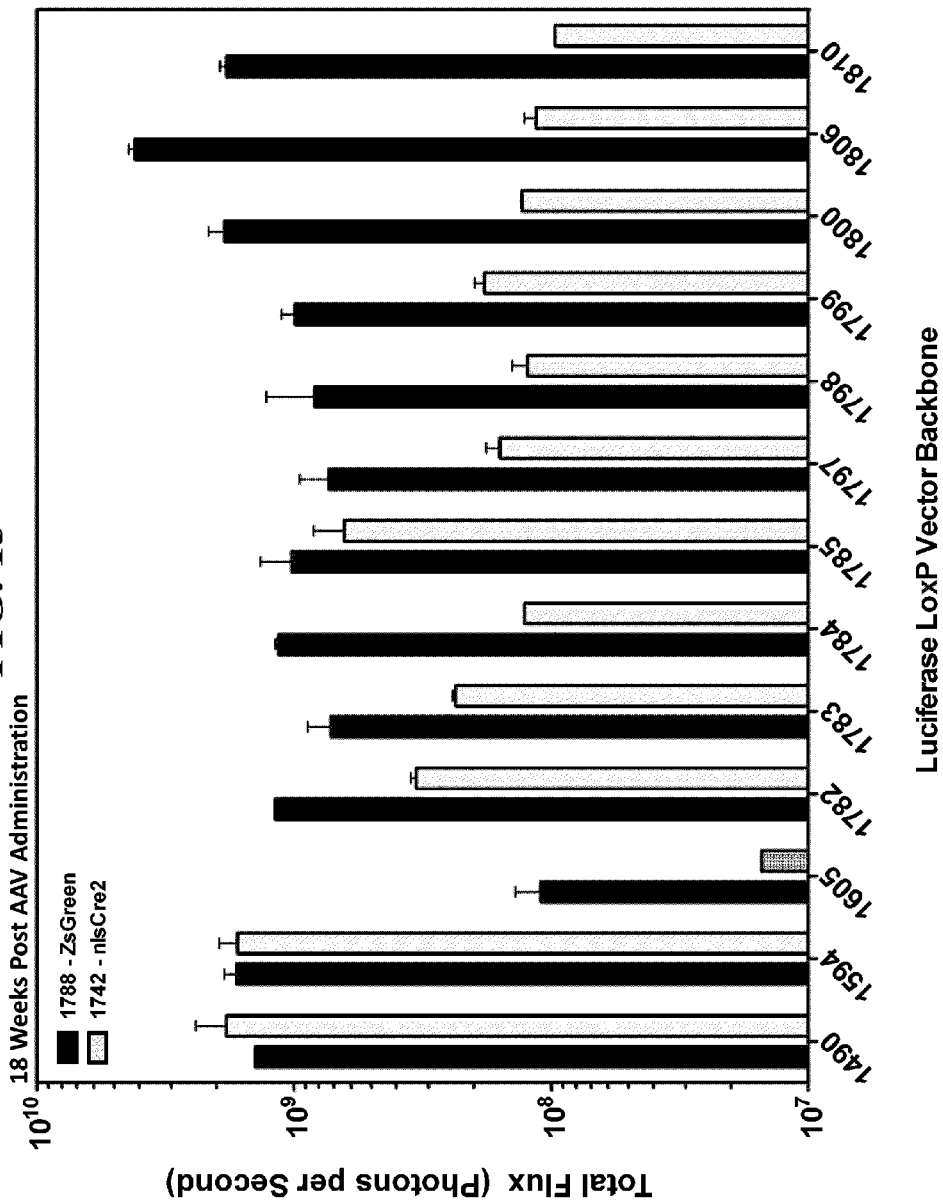
FIG. 13 is a graph illustrating a comparison of luciferase expression 18 weeks after transfecting mice with the indicated AAV vector encoding luciferase according to some embodiments herein. For each vector, a bar is shown for a mice co-transfected with ZsGreen and mice co-transfected with nlsCre2.

A comparison of luciferase activity (via Xenogen imaging) at 18 weeks after injection for zsGreen-injected mice and Cre-injected mice is shown in FIG. 13. Notably, vectors 1800, 1806, and 1810 produced very high levels of luciferase activity in the absence of Cre (levels even higher than vectors that lacked LoxP sites), but these activity levels were reduced more than 10-fold in the presence of Cre.

Example 10: In Vivo Testing of LoxP AAV Vectors

Figure 17:
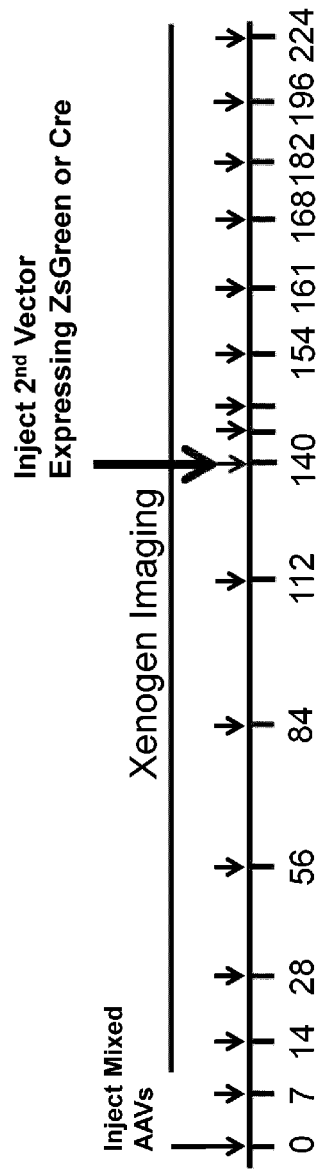
FIG. 17 is a schematic diagram illustrating an experimental protocol for reversibly expressing gene products encoded by AAV vector according to some embodiments herein.
Figure 18:
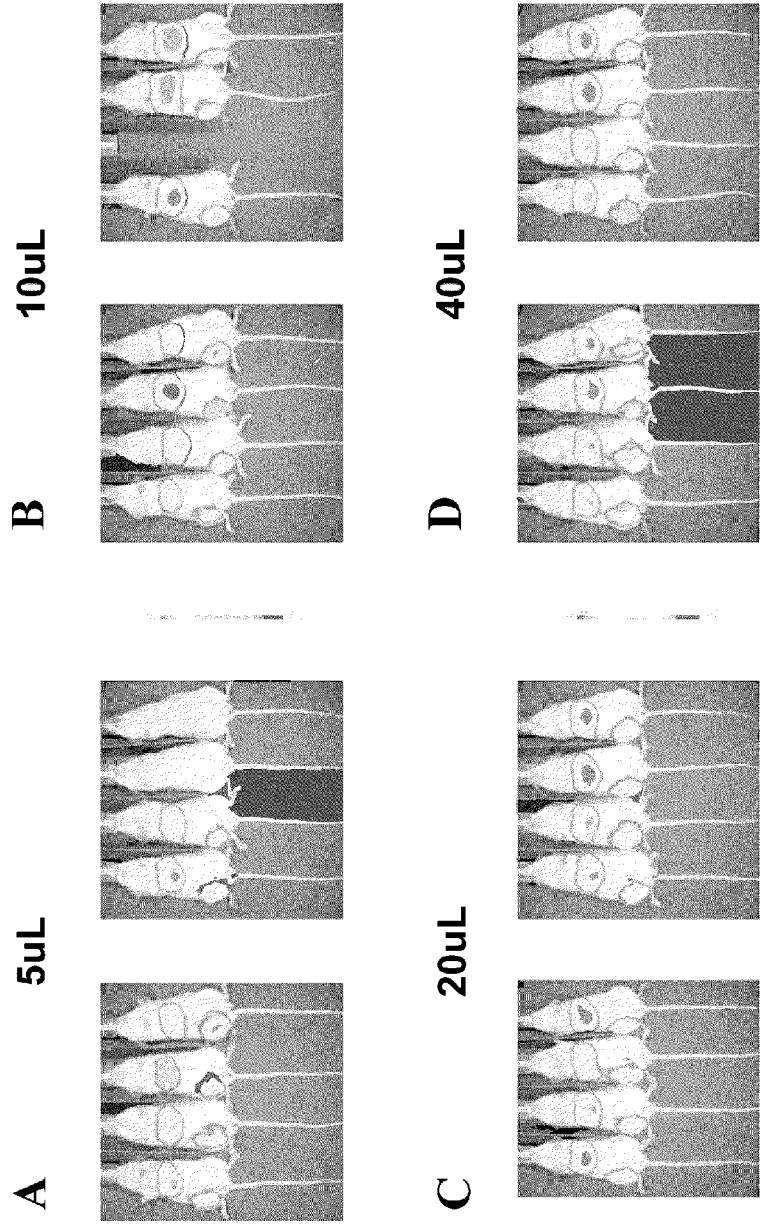
FIG. 18 is a series of photographs and schematics illustrating Xenogen imaging of mice injected with various amounts of AAV vector in accordance with some embodiments herein. Mice were injected with 5 uL (shown in FIG. 18A), 10 uL (shown in FIG. 18B), 20 uL (shown in FIG. 18C) or 40 uL (shown in FIG. 18D) of solution containing $5\times10^{10}$ GC vector 1806 (Luc-LoxP). The Xenogen images were taken 20 weeks after administration of vector 1806.
Figure 19:
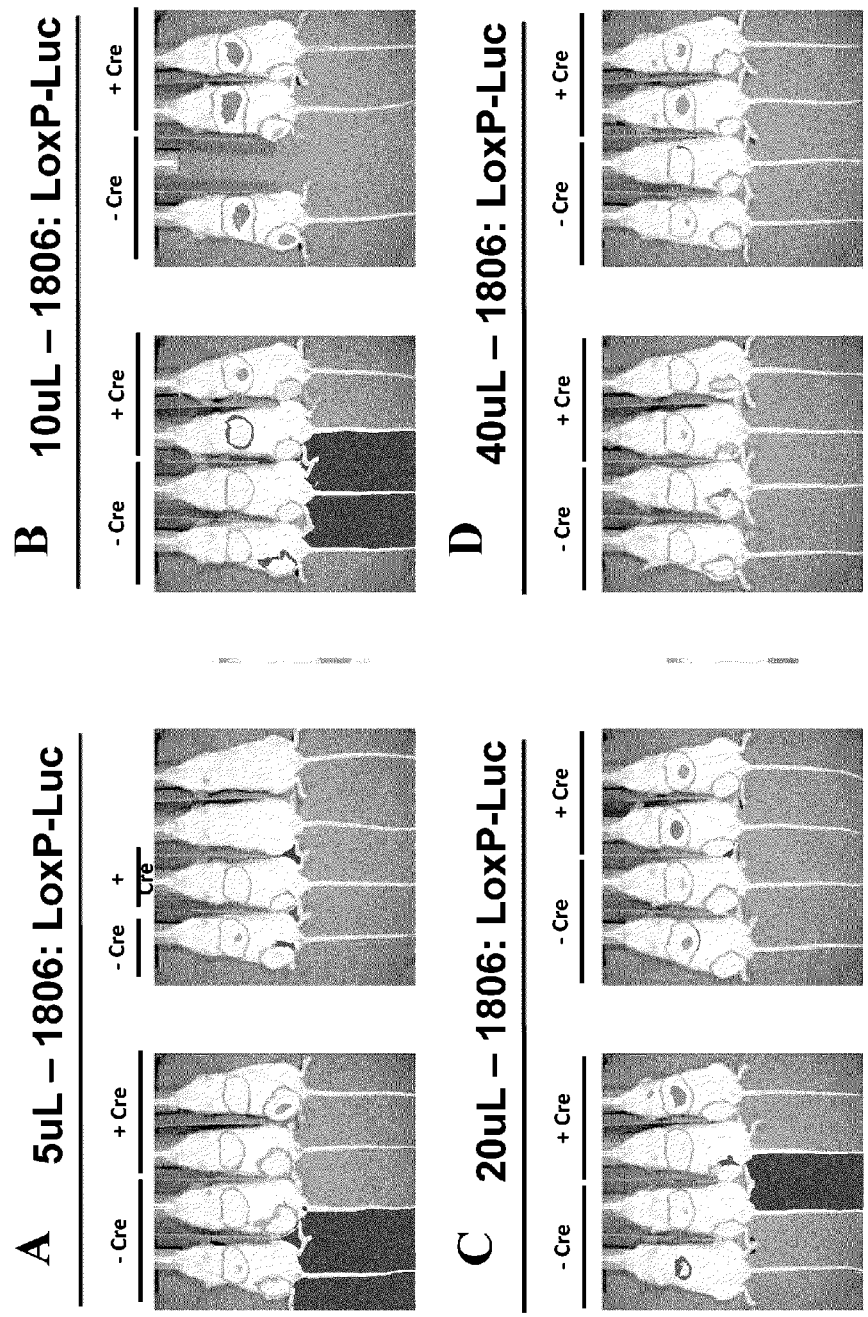
FIG. 19 is a series of photographs illustrating Xenogen imaging of mice injected with various amounts of AAV vector and subsequently injected with AAV vector encoding Cre or ZsGreen in accordance with some embodiments herein. Mice were injected with 5 uL (shown FIG. 19A), 10 uL (shown in FIG. 19B), 20 uL (shown in FIG. 19C) or 40 uL (shown in FIG. 19D) solution containing $5\times10^{10}$ GC vector 1806 (Luc-LoxP), and 20 weeks later, injected with 40 uL of $5\times10^{11}$ GC of a second AAV vector encoding either ZsGreen (−Cre) or Cre (+Cre). The Xenogen images were taken 3 days after administration of the second AAV vector.
Figure 20:
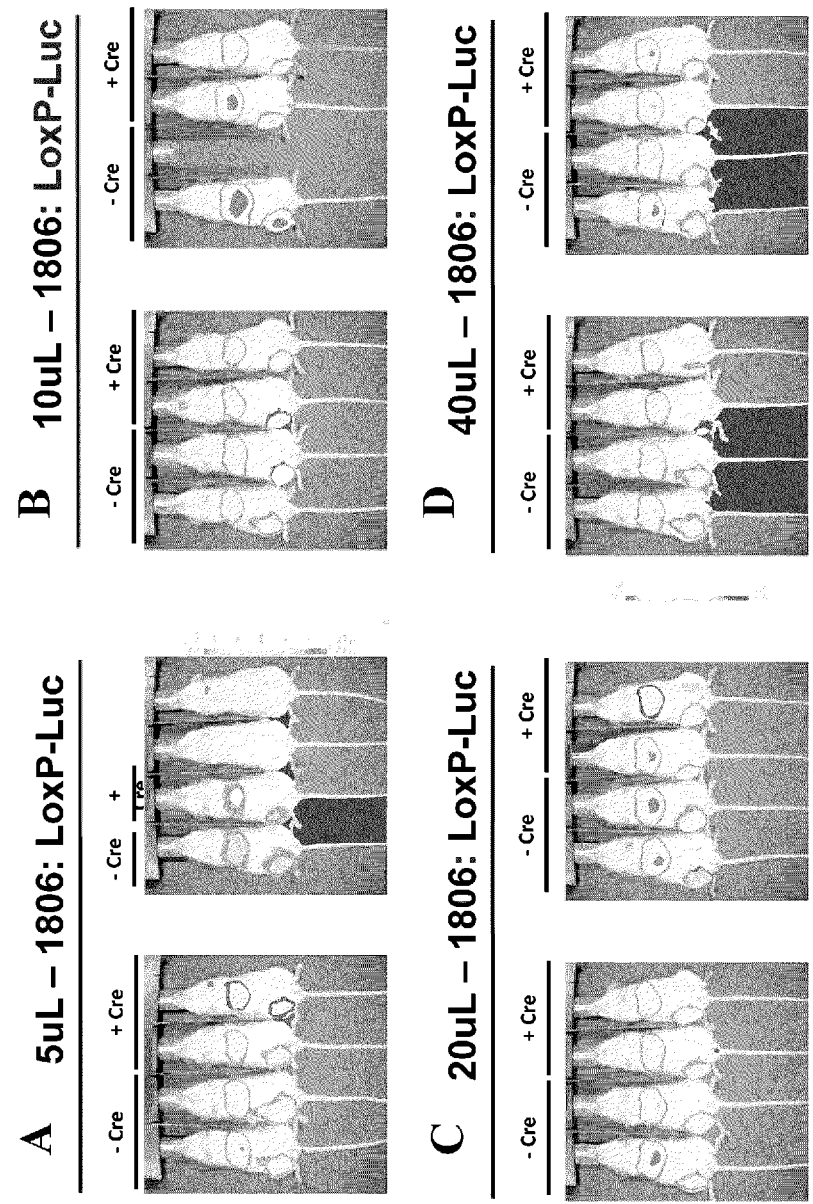
FIG. 20 is a series of photographs illustrating Xenogen imaging of mice injected with various amounts of AAV vector and subsequently injected with AAV vector encoding Cre or ZsGreen in accordance with some embodiments herein. Mice were injected with 5 uL (shown FIG. 20A), 10 uL (shown in FIG. 20B), 20 uL (shown in FIG. 20C) or 40 uL (shown in FIG. 20D) of solution containing $5\times10^{10}$ GC vector 1806 (Luc-LoxP), and 20 weeks later, injected with 40 uL of $5\times10^{11}$ GC of a second AAV vector encoding either ZsGreen (−Cre) or Cre (+Cre). The Xenogen images were taken 7 days after administration of the second AAV vector.
Figure 21:
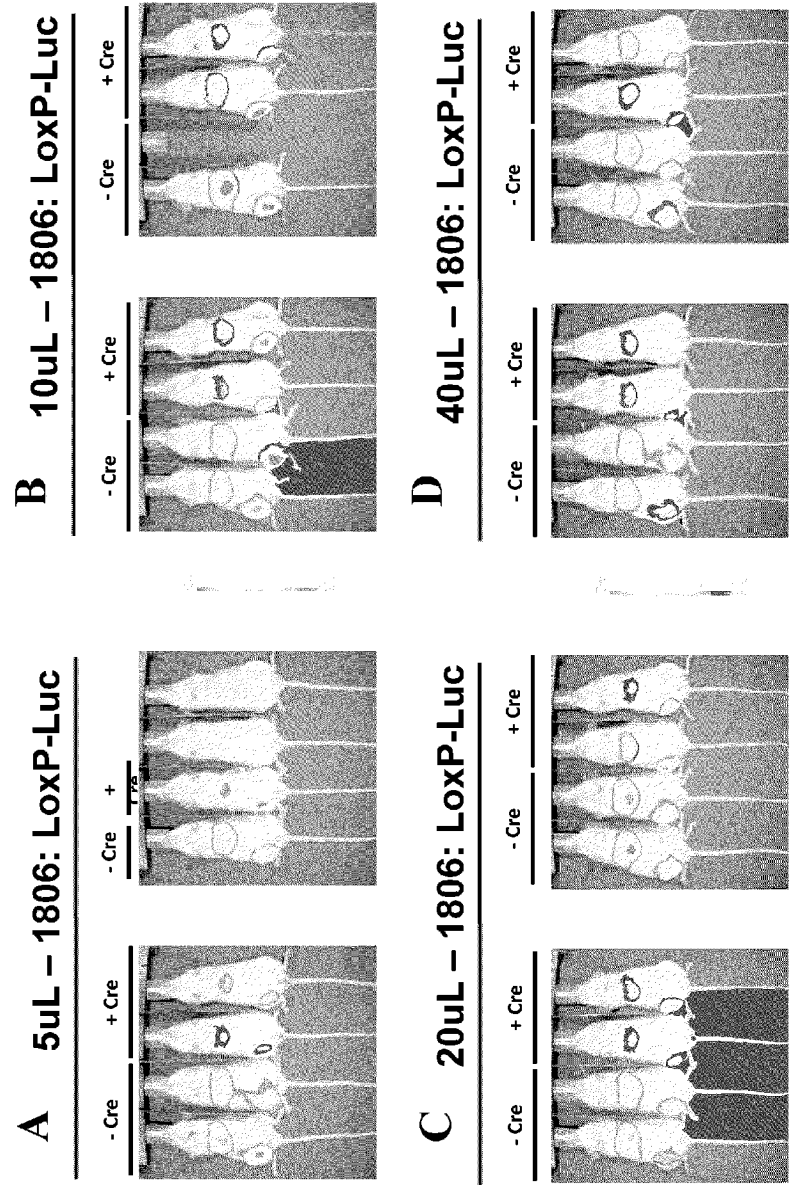
FIG. 21 is a series of photographs illustrating Xenogen imaging of mice injected with various amounts of AAV vector and subsequently injected with AAV vector encoding Cre or ZsGreen in accordance with some embodiments herein. Mice were injected with 5 uL (shown FIG. 21A), 10 uL (shown in FIG. 21B), 20 uL (shown in FIG. 21C) or 40 uL (shown in FIG. 21D) solution containing $5\times10^{10}$ GC vector 1806 (Luc-LoxP), and 20 weeks later, injected with 40 uL of $5\times10^{11}$ GC of a second AAV vector encoding either ZsGreen (−Cre) or Cre (+Cre). The Xenogen images were taken 14 days after administration of the second AAV vector.
Figure 22:
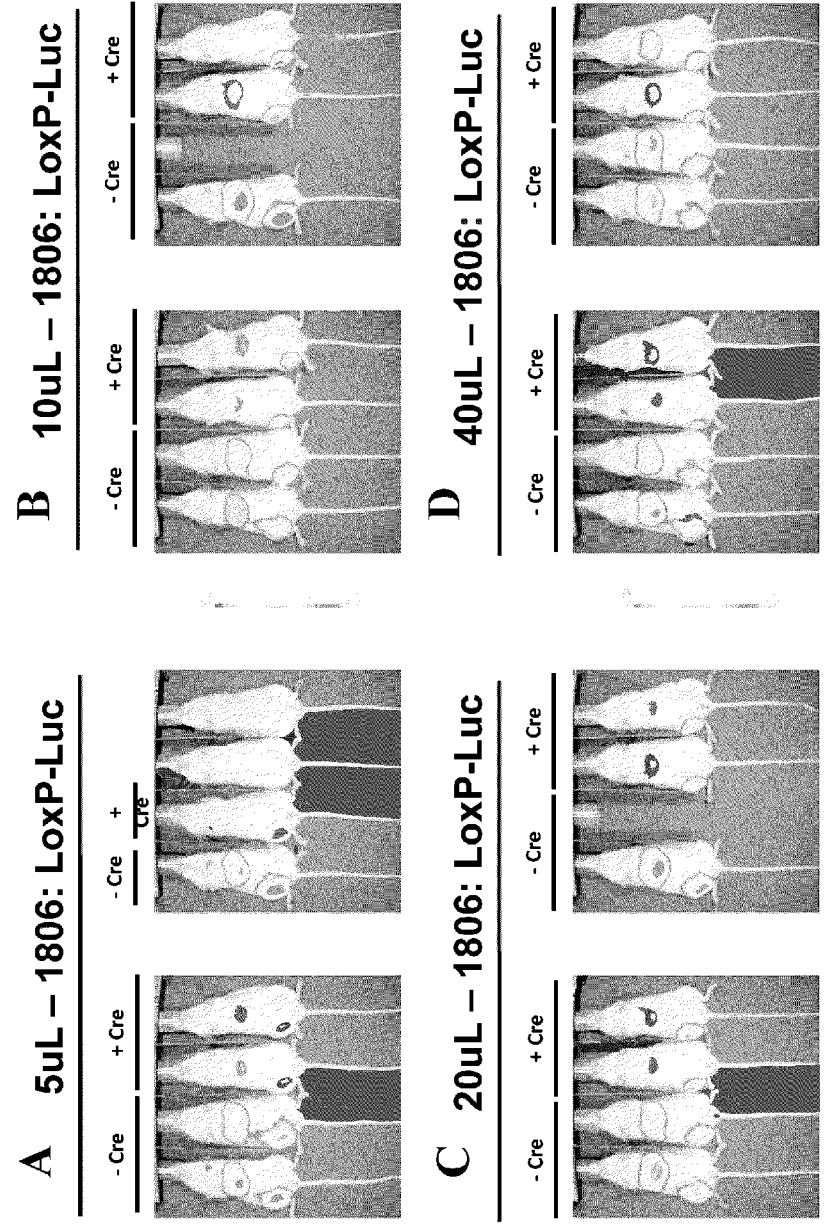
FIGS. 22A-D are a series of photographs illustrating Xenogen imaging of mice injected with various amounts of AAV vector according to the dosages shown in FIG. 21, and subsequently injected with AAV vector encoding Cre or ZsGreen in accordance with some embodiments herein. The Xenogen images were taken 21 days after administration of the second AAV vector.
Figure 23:
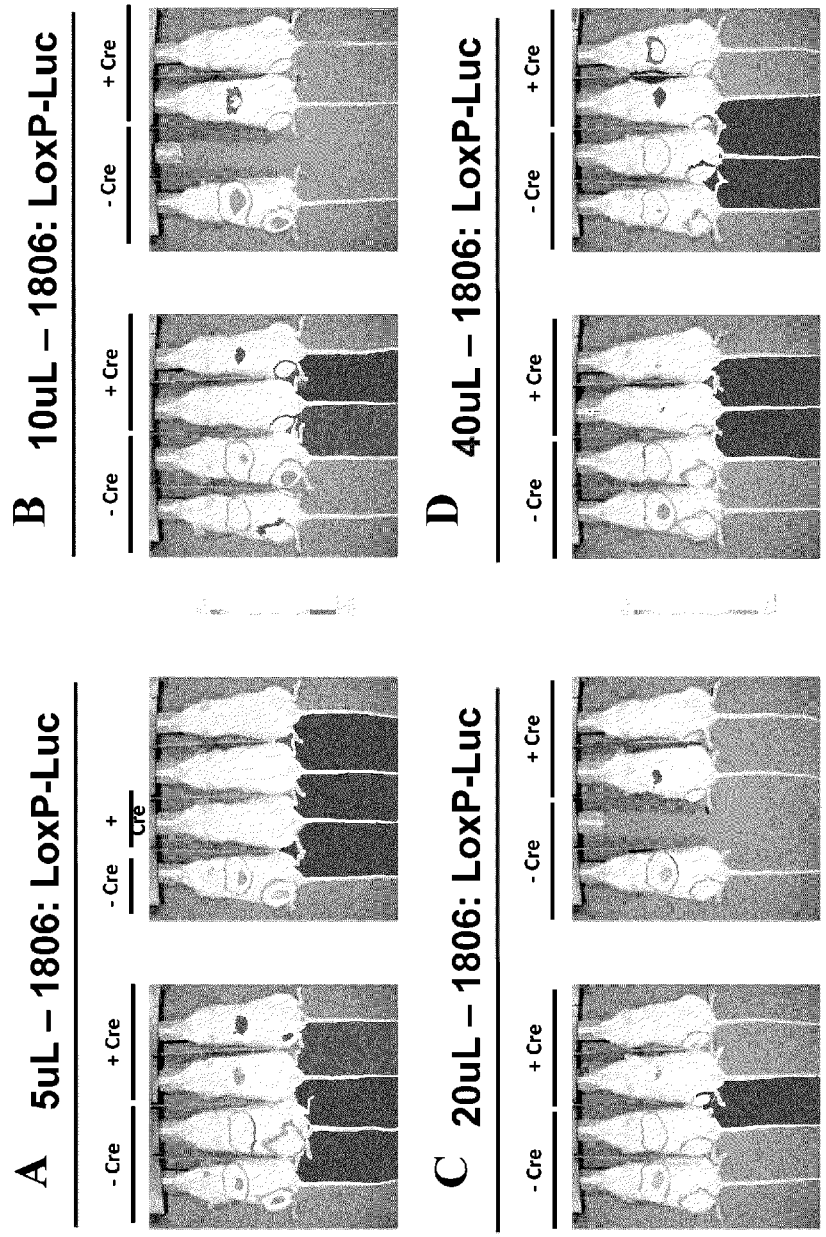
FIGS. 23A-D are a series of photographs illustrating Xenogen imaging of mice injected with various amounts of AAV vector according to the dosages shown in FIG. 21, and subsequently injected with AAV vector encoding Cre or ZsGreen in accordance with some embodiments herein. The Xenogen images were taken 28 days after administration of the second AAV vector.
Figure 24:
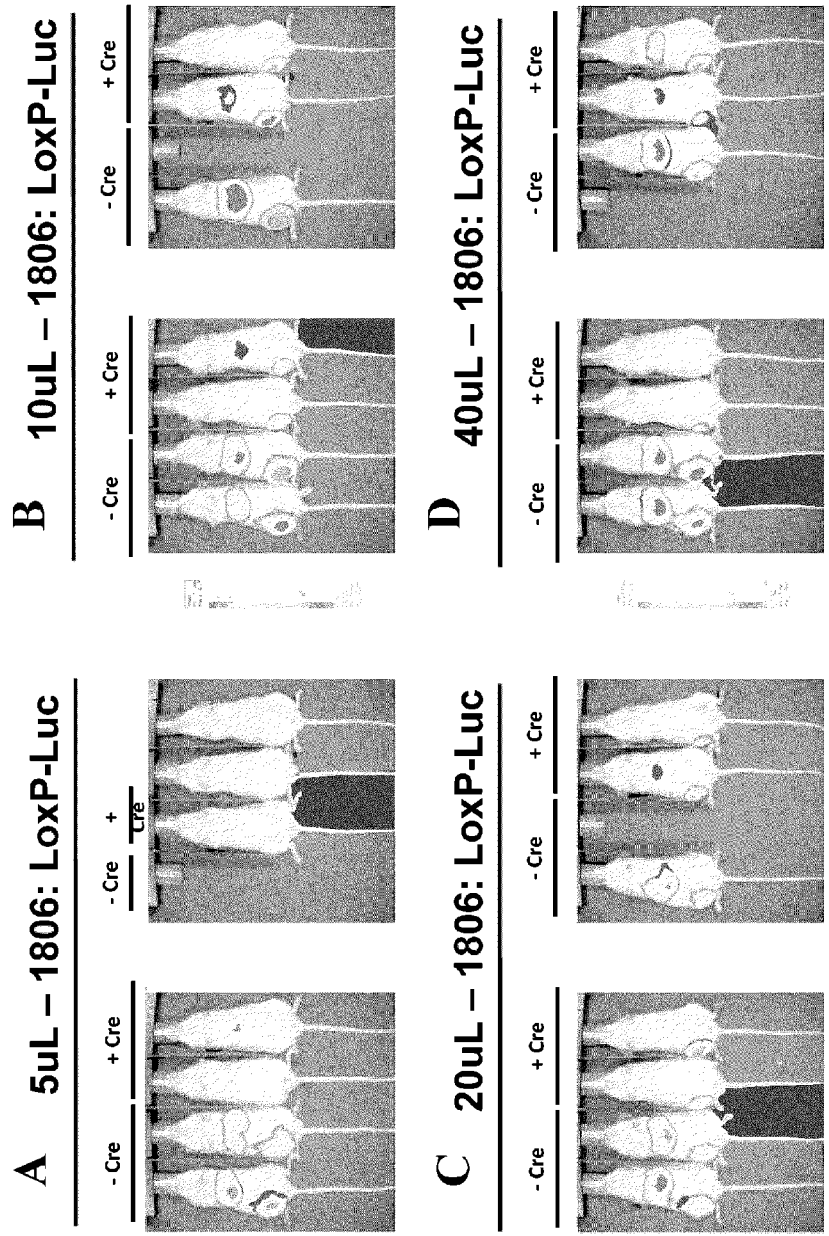
FIGS. 24A-D are a series of photographs illustrating Xenogen imaging of mice injected with various amounts of AAV vector according to the dosages shown in FIG. 21, and subsequently injected with AAV vector encoding Cre or ZsGreen in accordance with some embodiments herein. The Xenogen images were taken 56 days after administration of the second AAV vector.
Figure 25:
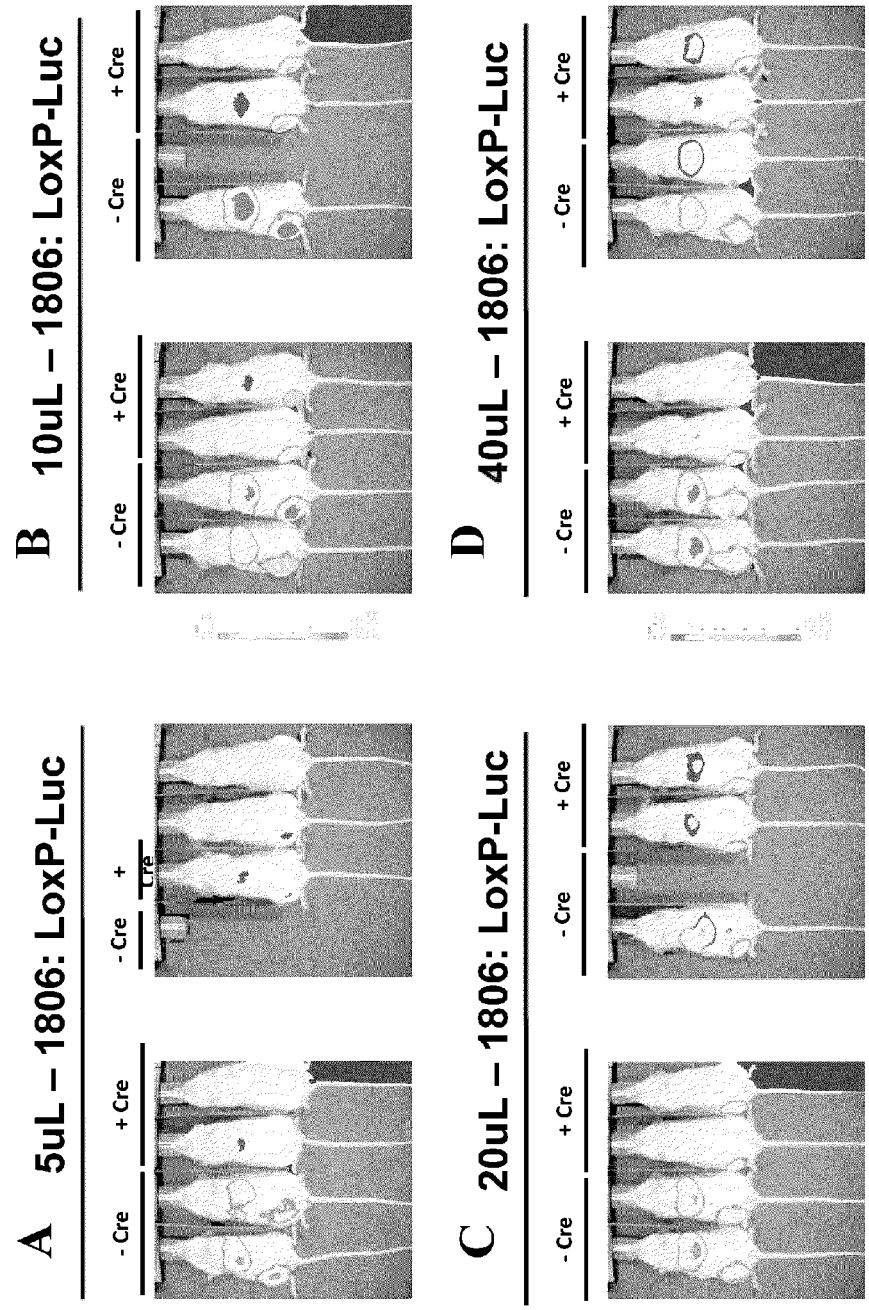
FIGS. 25A-D are a series of photographs illustrating Xenogen imaging of mice injected with various amounts of AAV vector according to the dosages shown in FIG. 21, and subsequently injected with AAV vector encoding Cre or ZsGreen in accordance with some embodiments herein. The Xenogen images were taken 84 days after administration of the second AAV vector.
Figure 26:
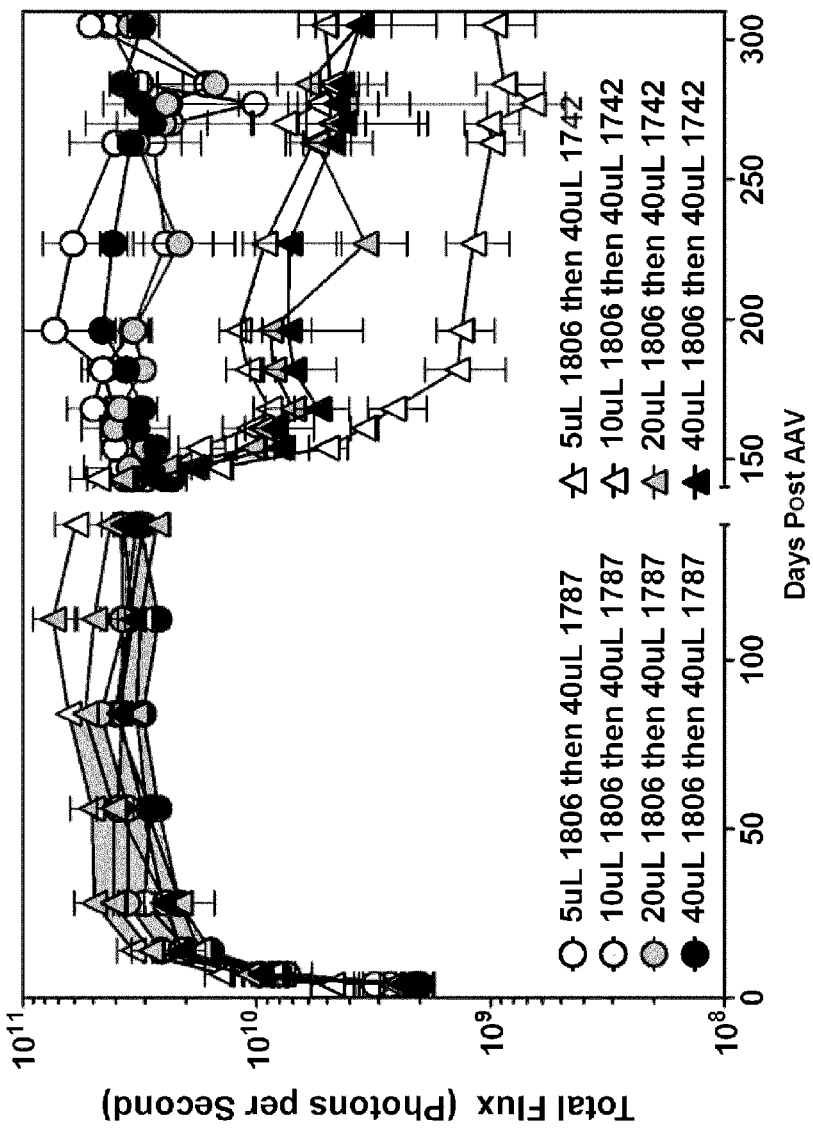
FIG. 26 is a graph illustrating luciferase activity in mice (total body) at various timepoints after injection with various quantities of vector 1806 encoding luciferase, 20 weeks later, injection with 40 uL of $5\times10^{11}$ GC of a second AAV vector encoding either ZsGreen (−Cre) or Cre (+Cre) in accordance with some embodiments herein.
Figure 27:
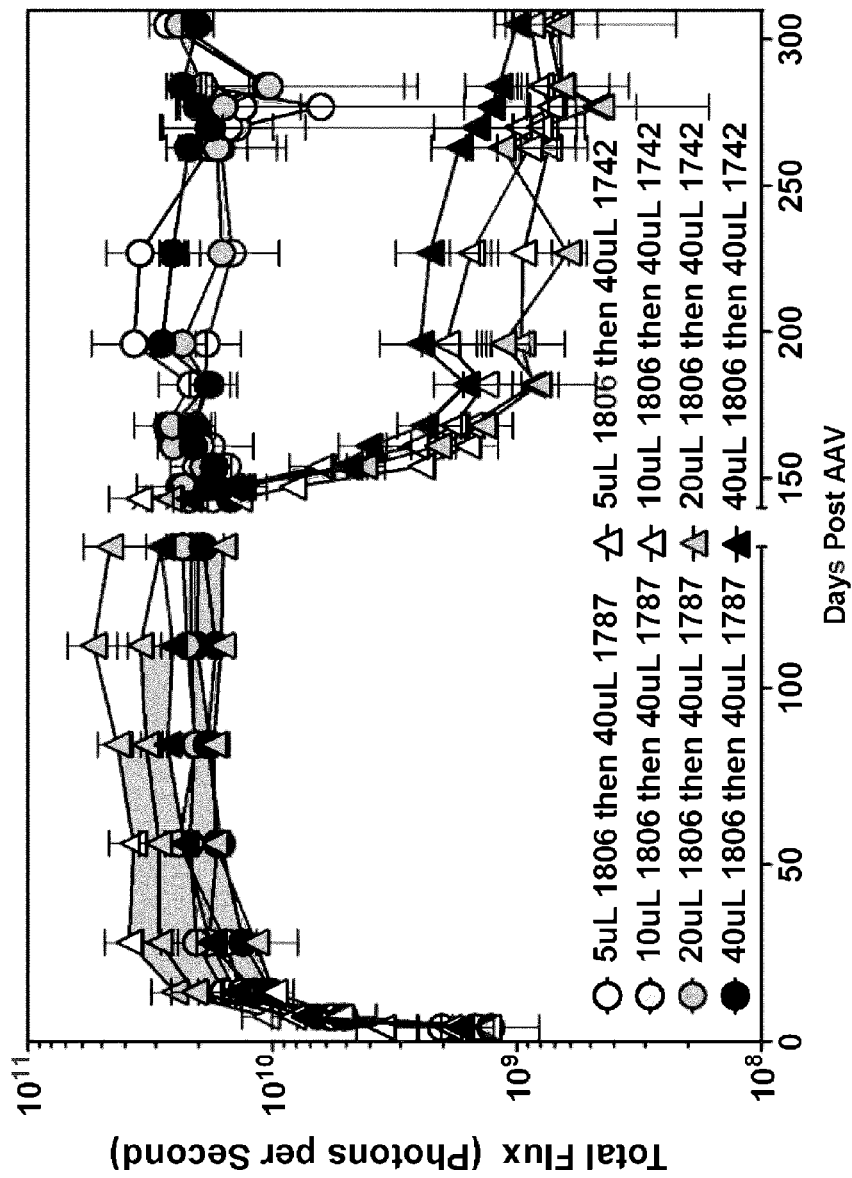
FIG. 27 is a graph illustrating luciferase activity in mice (liver) at various timepoints after injection with various quantities of vector 1806 encoding luciferase, 20 weeks later, injection with 40 uL of $5\times10^{11}$ GC of a second AAV vector encoding either ZsGreen (−Cre) or Cre (+Cre) in accordance with some embodiments herein.
Figure 28:
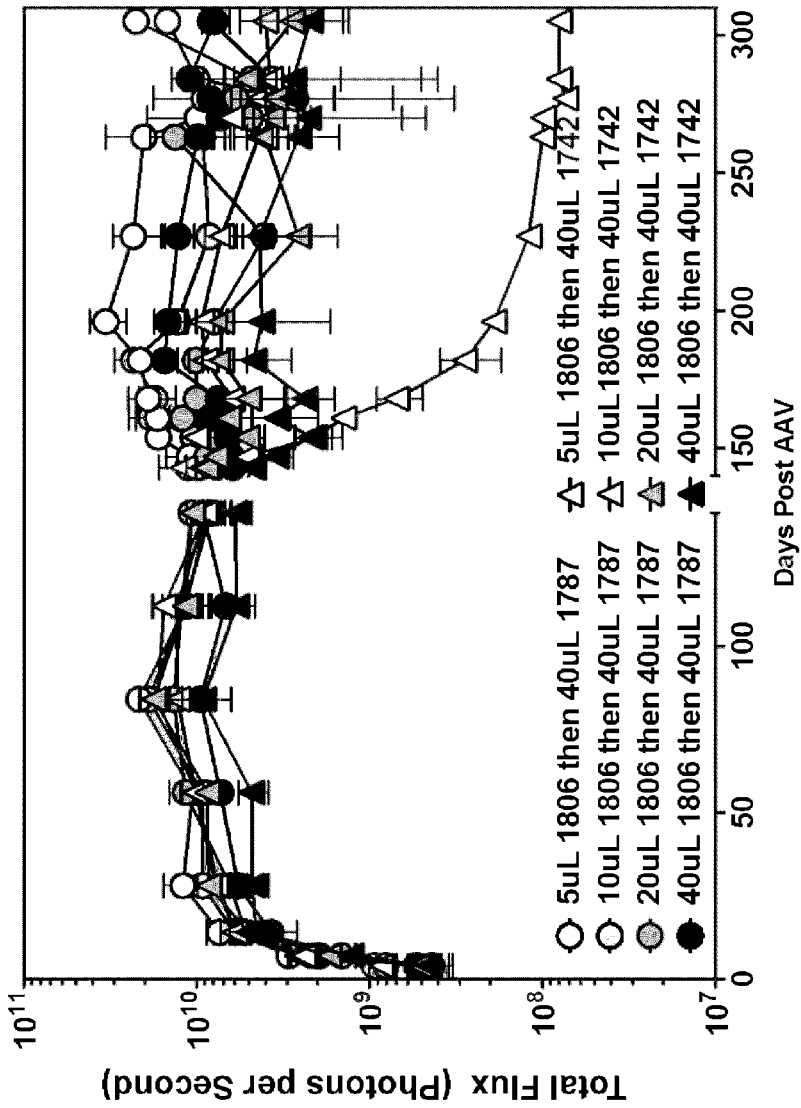
FIG. 28 is a graph illustrating luciferase activity in mice (leg) at various timepoints after injection with various quantities of vector 1806 encoding luciferase, 20 weeks later, injection with 40 uL of $5\times10^{11}$ GC of a second AAV vector encoding either ZsGreen (−Cre) or Cre (+Cre) in accordance with some embodiments herein.
Figure 29:
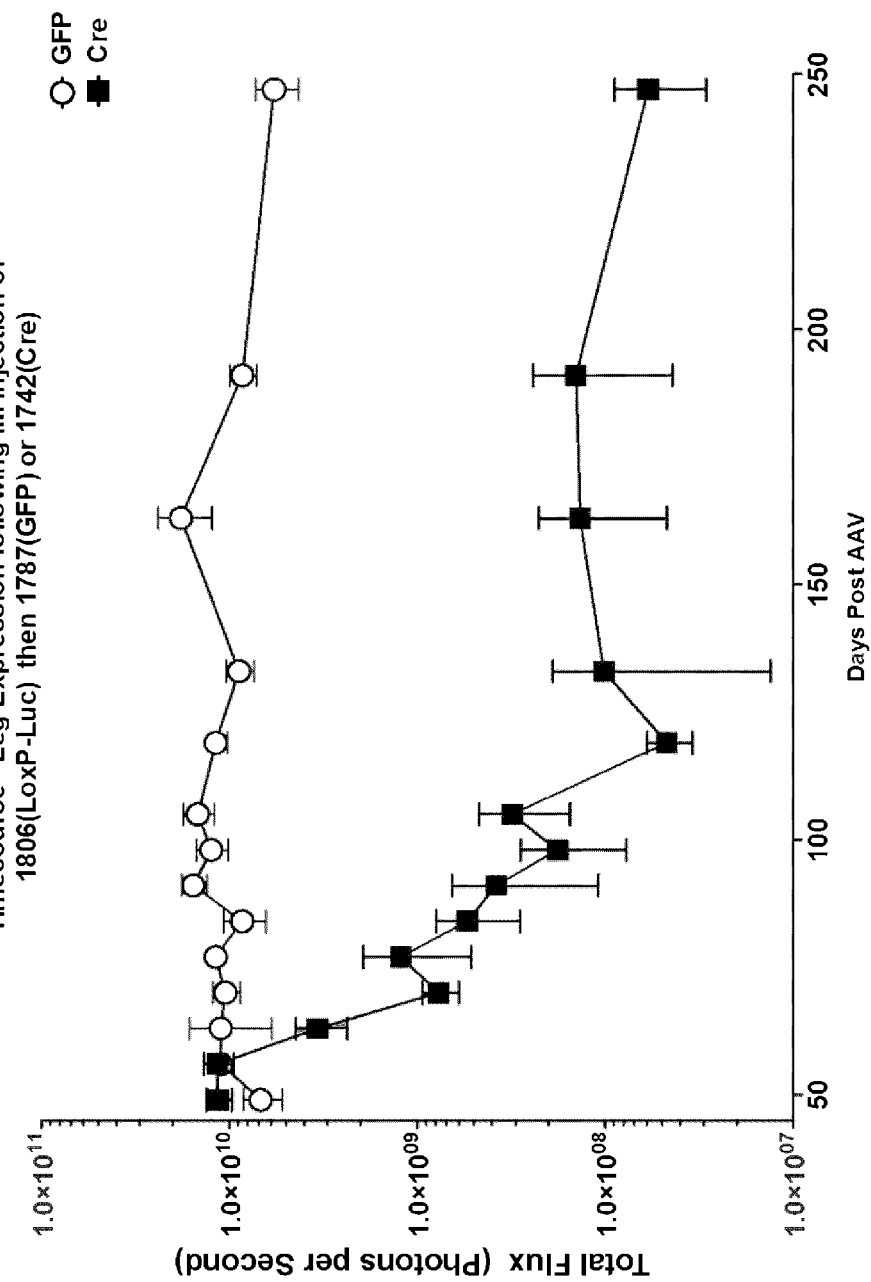
FIG. 29 is a graph illustrating luciferase activity in mice (leg) at various timepoints after intramuscular injection with AAV vector 1806 (encoding luciferase) and seven weeks later, were injected with either AAV vector 1787 (encoding GFP) or AAV vector 1742 (encoding Cre) in accordance with some embodiments herein.

LoxP AAV vectors in accordance with some embodiments herein encoding luciferase were injected into mice. Each luciferase vector was injected into four mice, of which two received a mixture of AAV vector encoding luciferase and control AAV vector 1788—AAV-CASI-ZsGreen-W-SV40 ("ZsGreen;" no Cre), and two received a mixture AAV vector encoding luciferase and Cre-encoding AAV vector 1742—AAV-CASI-nlsCre2-W-SV40 (+Cre). Mice were injected with 5 uL, 10 uL, 20 uL, or 40 uL solution containing $5 \times 10^{10}$ GC vector 1806 (Luc-LoxP). 20 weeks later, the mice were injected with 40 uL of $5 \times 10^{11}$ GC of a second AAV vector encoding either ZsGreen (−Cre) or Cre (+Cre). The vectors were provided at a ratio of $2.5 \times 10^9$ GC Luciferase to $1.25 \times 10^{11}$ GC ZsGreen or Cre Vector, which represented a 10× excess of Cre-expression vector versus Luciferase-encoding vector. The design of this experiment is schematically illustrated in FIG. 17. Luciferase expression was monitored via Xenogen imaging prior to administration of the second AAV vector (see FIG. 26), at the time that the second AAV vector was injected (i.e. 20 weeks after administration of the first, luciferase-encoding vector, see FIG. 18), and at 3, 7, 14, 21, 28, 56, and 84 days after injection (see FIGS. 19, 20, 21, 22, 23, 24, and 25, respectively). The luciferase activity along the timecourse is summarized in FIG. 26 (total body), FIG. 27 (liver), and FIG. 28 (leg).

Luciferase activity prior to administration of Cre was highest for 10 uL of vector 1806. As such, it is contemplated that total luciferase activity is not simply a function of the amount of luciferase vector administrated. After administration of Cre, whole-body luciferase activity was reduced substantially for all doses.

Example 11: In Vivo Expression of Antibody

Figure 31A:
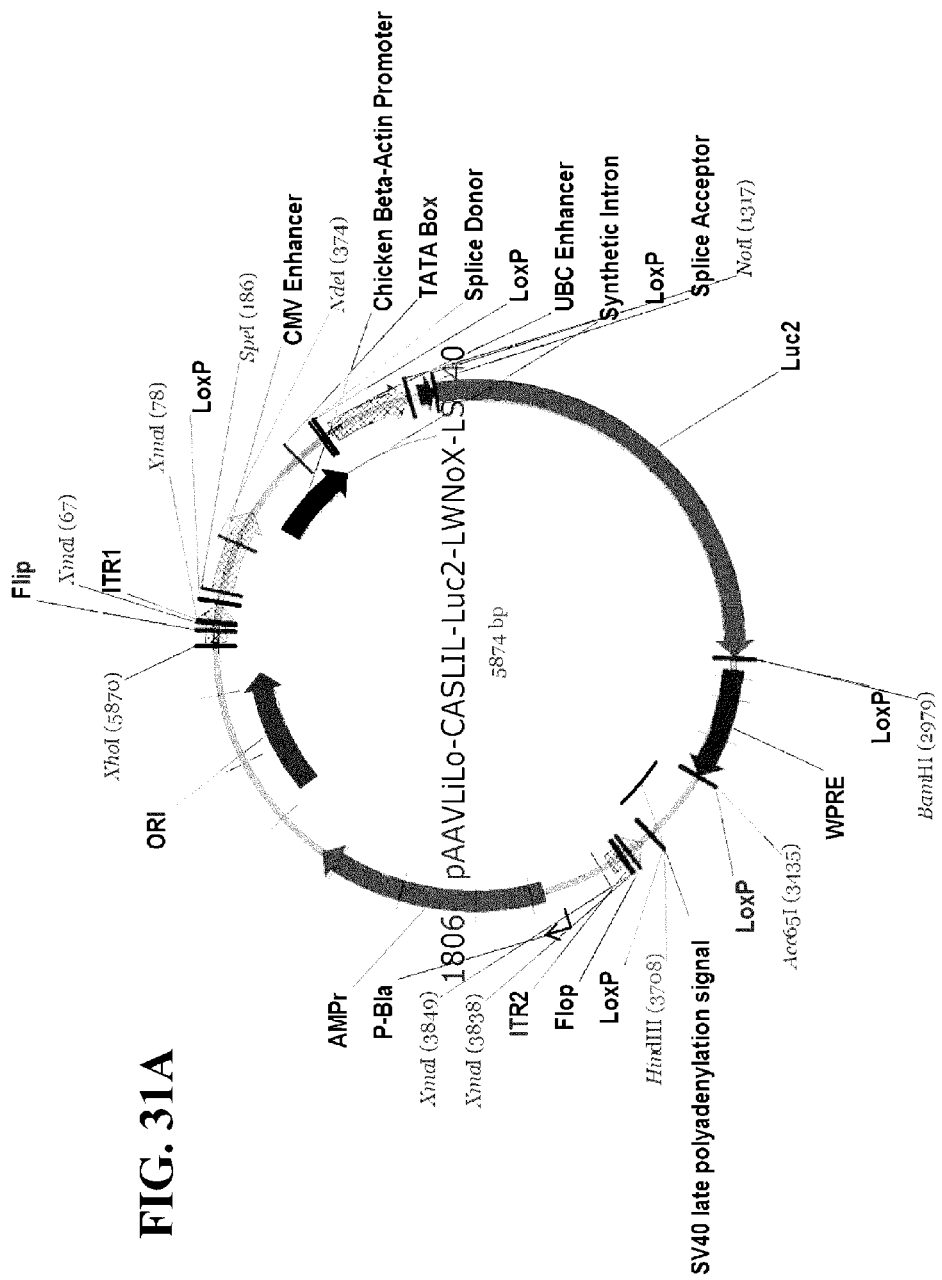
FIG. 31A is a vector map illustrating an AAV vector according to some embodiments herein. Depicted is vector pAAVLiLo-CASLIL-Luc2-LWNoX-LSV40 (vector 1806) (SEQ ID NO: 1).
Figure 31B:
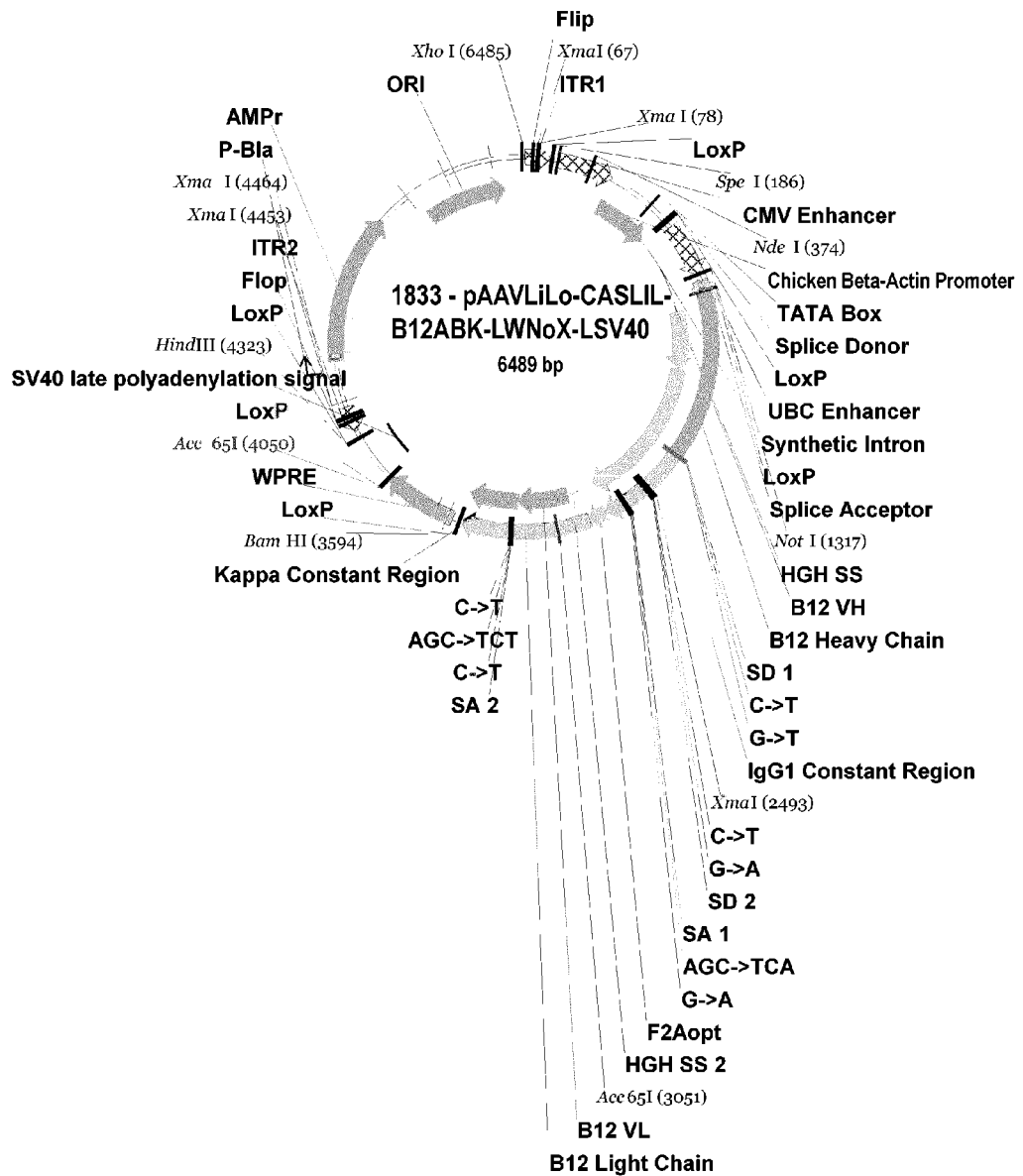
FIG. 31B is a vector map illustrating an AAV vector according to some embodiments herein. Depicted is vector pAAVLiLo-CASLIL-B12ABK-LWNoX-LSV40 (vector 1833) (SEQ ID NO: 2).
Figure 31C:
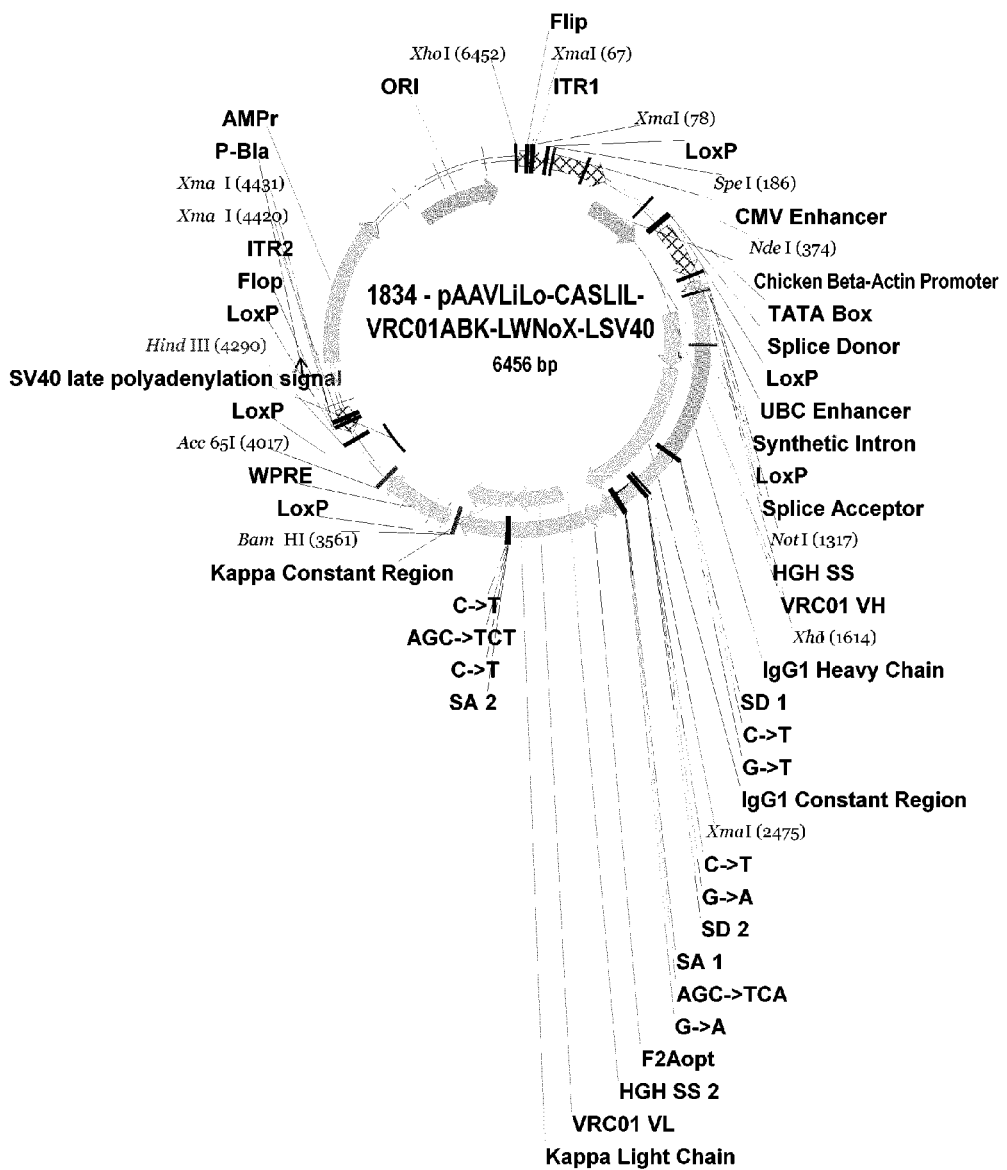
FIG. 31C is a vector map illustrating an AAV vector according to some embodiments herein. Depicted is vector pAAVLiLo-CASLIL-VRCO1ABK-LWNoX-LSV40 (vector 1834) (SEQ ID NO: 3).
Figure 31D:
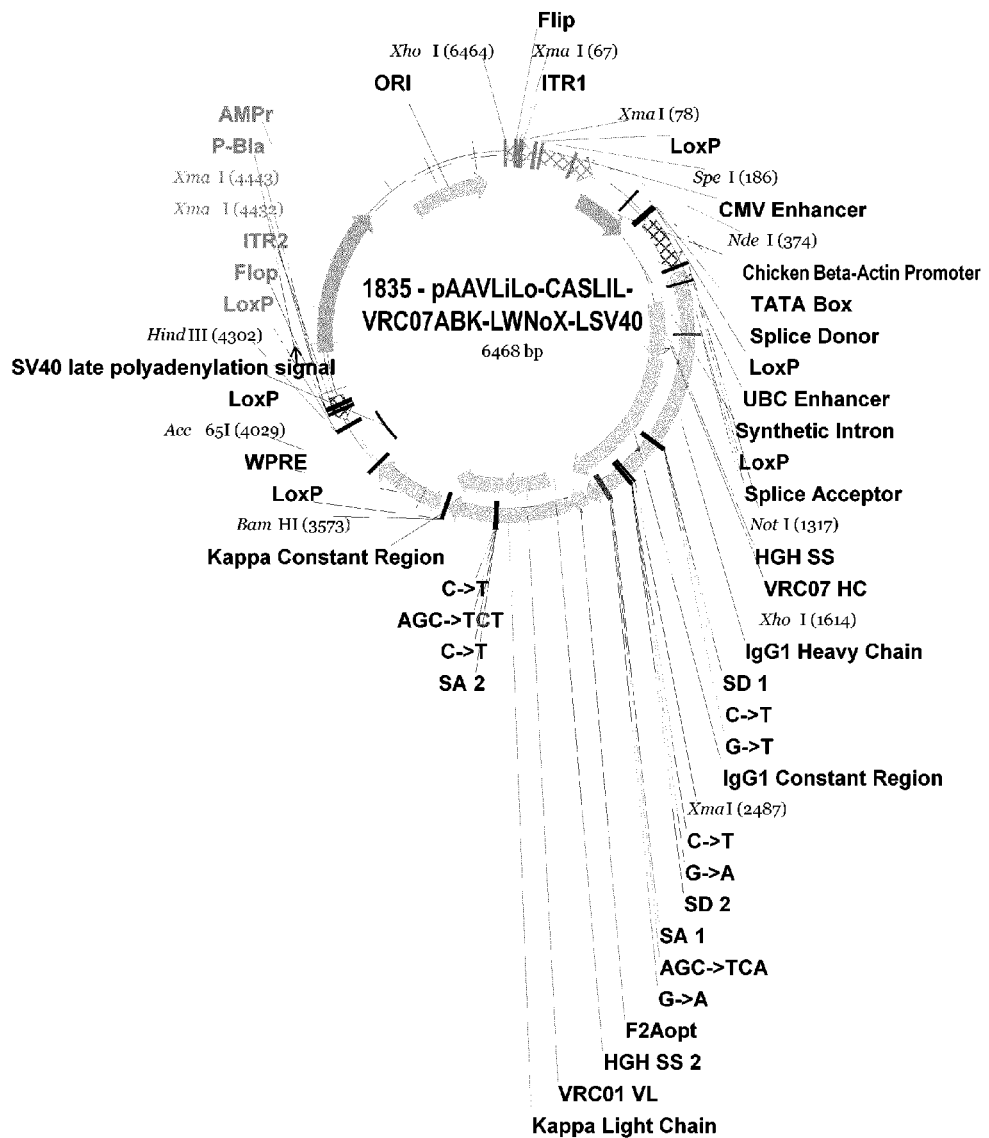
FIG. 31D is a vector map illustrating an AAV vector according to some embodiments herein. Depicted is vector pAAVLiLo-CASLIL-VRCO7ABK-LWNoX-LSV40 (1835) (SEQ ID NO: 4).

AAV vectors in accordance with some embodiments herein were used to express AC50 in mice, and subsequently exposed to Cre. Mice received intramuscular injection of either $2 \times 10^{10}$ GC of vector 1677 encoding the heavy chain and light chain of antibody AC50, but lacking loxP sites, or $2 \times 10^{10}$ GC of vector 1834 (SEQ ID NO: 3) encoding the heavy chain and light chain of antibody AC50, and containing six loxP sites (see FIG. 31C). 7 weeks later, the mice were injected intramuscularly with either $2.5 \times 10^{12}$ GC of vector 1787 (encoding GFP) or $2.5 \times 10^{12}$ GC of vector 1742 (encoding Cre). Levels of antibody expression were detected by a sandwich ELISA. Plates were coated with an Anti-Fc antibody, and a sample was added. Binding of antibody was detected using an anti-Kappa Light Chain-HRP. Although initial antibody expression levels were comparable, Antibody expression was substantially decreased for the combination of vector 1834 (LoxP sites) and vector 1742 (Cre) in comparison to the other vectors.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

While the present invention has been described in some detail for purposes of clarity and understanding, one skilled in the art will appreciate that various changes in form and detail can be made without departing from the true scope of the invention.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

What is claimed is:

1. A reversible expression system for gene products, the system comprising:
 a first non-integrating adeno-associated virus vector comprising:
  a first ITR;
  a promoter positioned 3' to the first ITR;
  a first recombinase target site positioned 3' to the first ITR and 5' to a 3' end of the promoter;
  a second recombinase target site positioned 3' to a 5' end of the promoter and 5' to the 3' end of the promoter, by which the second recombinase target site is within the promoter;
  a third recombinase target site positioned 3' to the second recombinase target site and 5' to the 3' end of the promoter, by which the third recombinase target site is within the promoter;

an insertion site positioned 3' to the promoter, such that the promoter would be operably linked to at least an inserted polynucleotide;

a fourth recombinase target site positioned 3' to the insertion site;

a post-transcriptional regulatory element positioned 3' to the fourth recombinase target site;

a fifth recombinase target site positioned 3' to the post-transcriptional regulatory element;

a polyadenylation sequence positioned 3' to the fifth recombinase target site;

a sixth recombinase target site positioned 3' to the polyadenylation sequence; and a second ITR positioned 3' to the sixth recombinase target site, wherein the first, second, third, fourth, fifth, and sixth recombinase target sites are oriented in the same direction and wherein the first, second, third, fourth, fifth, and sixth recombinase target sites each comprise a same recombinase target nucleic acid sequence; and a source of a recombinase configured to induce recombination events between two or more of the recombinase target sites, wherein the recombinase target sites are configured such that the recombination events between the two or more of the recombinase target sites remove the insertion site and, if present, the inserted polynucleotide, thereby reducing or eliminating expression of the insertion site and, if present, the inserted polynucleotide.

2. The expression system of claim 1, wherein the source of recombinase comprises a second vector comprising a promoter operably linked to a recombinase polynucleotide encoding the recombinase.

3. The expression system of claim 2, wherein the second vector comprises one of an adeno-associated virus vector, or an adenovirus vector.

4. The expression system of claim 1, wherein the source of recombinase comprises a recombinase polypeptide fused to a cell-penetration peptide.

5. The expression system of claim 1, wherein the promoter comprises a synthetic intron comprising:

a splice donor;

a transcriptional enhancer positioned 3' to the splice donor; and a splice acceptor positioned 3' to the splice donor, wherein the first recombinase target and second recombinase target flank the synthetic intron.

6. The expression system of claim 1, wherein the recombinase target sites comprise Lox sites and the recombinase comprises Cre.

7. The expression system of claim 1, wherein the recombinase target sites comprise FRT sites and the recombinase comprises FLPase.

8. The expression system of claim 1, wherein the first non-integrating adeno-associated vector further comprises a cleavage polynucleotide positioned 3' to the third recombinase target site.

9. The expression system of claim 1, wherein the post-transcriptional regulatory element comprises the polynucleotide sequence of SEQ ID NO: 27, SEQ ID NO: 28, or SEQ ID NO: 29.

10. A method of reversibly expressing at least a first gene product in a mammal, the method comprising:

administering to the mammal a first non-integrating adeno-associated virus vector comprising:

a first ITR;

a promoter positioned 3' to the first ITR;

a first recombinase target site positioned 3' to the first ITR and 5' to a 3' end of the promoter;

a second recombinase target site positioned 3' to a 5' end of the promoter and 5' to the 3' end of the promoter, by which the second recombinase target site is within the promoter;

a third recombinase target site positioned 3' to the second recombinase target site and S' to the 3' end of the promoter, by which the third recombinase target site is within the promoter;

an insertion site positioned 3' to the 5' end of the promoter, the insertion site comprising a first polynucleotide encoding a first gene product, such that the promoter is operably linked to the first polynucleotide;

a fourth recombinase target site positioned 3' to the insertion;

a post-transcriptional regulatory element positioned 3' to the fourth recombinase target site;

a fifth recombinase target site positioned 3' to the post-transcriptional regulatory element;

a polyadenylation sequence positioned 3' to the fifth recombinase target site;

a sixth recombinase target site positioned 3' to the polyadenylation sequence; and a second ITR positioned 3' to the sixth recombinase target site, wherein the first, second, third, fourth, fifth, and sixth recombinase target sites are oriented in the same direction, wherein the first, second, third, fourth, fifth, and sixth recombinase target sites each comprise a same recombinase target nucleic acid sequence, wherein, after administration of the first non-integrating adeno-associated virus vector, the first gene product is expressed in the mammal; and administering a recombinase to the mammal, wherein the recombinase induces recombination between at least two of the recombinase target sites after the first gene product is expressed, thereby reducing or eliminating expression of the insertion site and the first gene product.

11. The method of claim 10, wherein administering the recombinase comprises administering a second vector to the mammal, wherein the second vector comprises a promoter operably linked to a recombinase polynucleotide encoding the recombinase.

12. The method of claim 11, wherein expression of the recombinase polynucleotide is induced after the first gene product is expressed, thereby reducing or eliminating expression of the first gene product.

13. The method of claim 10, wherein the recombinase is administered after the first adeno-associated virus vector, thereby reducing or eliminating expression of the first gene product.

14. The method of claim 10, wherein administering the recombinase comprises contacting at least one cell of the mammal with the recombinase fused to a cell-penetration polypeptide.

15. The method of claim 10, wherein the recombinase target sites comprise Lox sites and the recombinase comprises Cre.

16. The method of claim 10, wherein the recombinase target sites comprise FRT sites and the recombinase comprises FLPase.

17. The method of claim 10, wherein the first gene product comprises at least a heavy chain or a light chain of an immunoglobulin.

18. The method of claim 10, wherein the first adeno-associated virus vector further comprises a cleavage polynucleotide positioned 3' of the first polynucleotide, and a second polynucleotide encoding a second gene product positioned 3' of the cleavage polynucleotide.

19. The method of claim 10, wherein the recombinase induces recombination events involving the first, second, third, fourth, fifth, and sixth recombinase target sites, thereby excising at least a portion of the first adeno-associated virus vector.

20. The method of claim 10, wherein expression of the first gene product is reduced at least 10-fold.

21. The method of claim 10, wherein the mammal is a human.

22. The expression system of claim 1, wherein the first recombinase target site and the second recombinase target site are in an intron.

23. The reversible expression system of claim 1, wherein the first non-integrating adeno-associated virus vector is configured to express the inserted polypeptide in a subject for a period of time.

24. The reversible expression system of claim 1, wherein the first non-integrating adeno-associated virus vector lacks a Cap gene, a Rep gene, or a Cap gene and a Rep gene.

25. The reversible expression system of claim 1, wherein the post-transcriptional regulatory element comprises a woodchuck hepatitis virus posttranscriptional regulatory element (WPRE).

* * * * *

UNITED STATES PATENT AND TRADEMARK OFFICE
CERTIFICATE OF CORRECTION

PATENT NO. : 9,943,611 B2  
APPLICATION NO. : 14/067786  
DATED : April 17, 2018  
INVENTOR(S) : Balazs et al.

Page 1 of 1

It is certified that error appears in the above-identified patent and that said Letters Patent is hereby corrected as shown below:

In the Specification

In Column 1 at Line 28, Change "CALTE092A REPLACEMENT." to --CALTE092A_REPLACEMENT.--.

In Column 3 at Line 62, After "human" insert --.--.

In Column 6 at Line 28, Change "1211" to --12H--.

In Column 31 at Line 28, Change "hematopoetic" to --hematopoietic--.

In Column 33 at Line 58, Change "hydroxpropylcellulose." to --hydroxypropylcellulose.--.

In Column 41 at Line 1-2, Change "Antibody" to --antibody--.

In the Claims

In Column 84 at Line 8, In Claim 10, change "S'" to --5'--.

In Column 84 at Line 17 (approx.), In Claim 10, change "insertion;" to --insertion site;--.

Signed and Sealed this  
Thirtieth Day of October, 2018

Andrei Iancu  
*Director of the United States Patent and Trademark Office*